United States Patent
Hiyama et al.

(10) Patent No.: US 11,779,260 B2
(45) Date of Patent: Oct. 10, 2023

(54) COGNITIVE FUNCTION EVALUATION METHOD, COGNITIVE FUNCTION EVALUATION DEVICE, AND NON-TRANSITORY COMPUTER-READABLE RECORDING MEDIUM IN WHICH COGNITIVE FUNCTION EVALUATION PROGRAM IS RECORDED

(71) Applicant: Panasonic Intellectual Property Corporation of America, Torrance, CA (US)

(72) Inventors: Takahiro Hiyama, Tokyo (JP); Yoshikuni Sato, Tokyo (JP); Takahiro Aihara, Osaka (JP); Kengo Wada, Osaka (JP); Taichi Hamatsuka, Osaka (JP); Yoshihiro Matsumura, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 305 days.

(21) Appl. No.: 16/997,482

(22) Filed: Aug. 19, 2020

(65) Prior Publication Data
US 2021/0059596 A1 Mar. 4, 2021

Related U.S. Application Data

(60) Provisional application No. 62/893,297, filed on Aug. 29, 2019.

(30) Foreign Application Priority Data

Feb. 14, 2020 (JP) ................................. 2020-023432

(51) Int. Cl.
*A61B 5/00* (2006.01)
*A61B 5/11* (2006.01)
(Continued)

(52) U.S. Cl.
CPC .......... *A61B 5/4088* (2013.01); *A61B 5/1071* (2013.01); *A61B 5/112* (2013.01); *A61B 5/117* (2013.01); *A61B 5/7275* (2013.01)

(58) Field of Classification Search
None
See application file for complete search history.

(56) References Cited

U.S. PATENT DOCUMENTS 9,149,222 B1 * 10/2015 Zets ..................... A61B 5/4023
9,526,946 B1 * 12/2016 Zets ..................... G09B 19/0038
(Continued)

FOREIGN PATENT DOCUMENTS

| JP | 2013-255786 | 12/2013 |
| WO | 2018/066422 | 4/2018 |

OTHER PUBLICATIONS

W.-H. Wang, Y.-L. Hsu, P.-C. Chung and M.-C. Pai, "Predictive Models for Evaluating Cognitive Ability in Dementia Diagnosis Applications Based on Inertia- and Gait-Related Parameters," in IEEE Sensors Journal, vol. 18, No. 8, pp. 3338-3350, Apr. 15, 15, 2018, doi: 10.1109/JSEN.2018.2809478. (Year: 2018).*

(Continued)

*Primary Examiner* — Benjamin S Melhus
(74) *Attorney, Agent, or Firm* — WENDEROTH, LIND & PONACK, L.L.P.

(57) ABSTRACT

A cognitive function evaluation method in a cognitive function evaluation device that evaluates a cognitive function based on a walking motion of a subject includes: acquiring walking data related to walking of the subject; detecting, from the walking data, at least one of an angle of an ankle joint of one foot and an angle of a knee joint of one leg of the subject; and determining a cognitive function level of the subject using at least one of the angle of the ankle joint and the angle of the knee joint.

3 Claims, 41 Drawing Sheets

(51) Int. Cl.
*A61B 5/107* (2006.01)
*A61B 5/117* (2016.01)

(56) References Cited

U.S. PATENT DOCUMENTS

| | | | | |
|---|---|---|---|---|
| 2012/0209149 A1* | 8/2012 | Yoneyama | ............ | A61B 5/7246 600/595 |
| 2013/0123665 A1* | 5/2013 | Mariani | ............... | A61B 5/6807 600/592 |
| 2014/0198962 A1* | 7/2014 | Anabuki | ............... | G06T 7/0014 382/128 |
| 2014/0276130 A1* | 9/2014 | Mirelman | ............ | A61B 5/1117 600/595 |
| 2015/0003687 A1* | 1/2015 | Utsunomiya | .......... | G06V 40/25 382/107 |
| 2017/0055880 A1* | 3/2017 | Agrawal | ................. | A43B 3/38 |
| 2017/0243354 A1* | 8/2017 | Tafazzoli | ............. | A61B 5/7275 |
| 2018/0132758 A1* | 5/2018 | Benford | ................ | A61B 5/112 |
| 2019/0150793 A1* | 5/2019 | Barth | ...................... | G06F 3/011 |
| 2019/0380623 A1* | 12/2019 | Vidal | ...................... | G01C 22/006 |
| 2020/0000373 A1* | 1/2020 | Agrawal | ............. | A61B 5/7267 |
| 2020/0008735 A1 | 1/2020 | Okada et al. | | |
| 2020/0383608 A1* | 12/2020 | Ramesh | .................. | G01S 7/415 |
| 2021/0059565 A1* | 3/2021 | Morris | ................. | A61B 5/4088 |
| 2021/0059569 A1* | 3/2021 | Hiyama | ................ | A61B 5/1127 |
| 2021/0315486 A1* | 10/2021 | Delp | ...................... | G16H 50/50 |
| 2022/0257148 A1* | 8/2022 | Aihara | .................. | A61B 5/1117 |
| 2022/0296960 A1* | 9/2022 | Fung | .................... | G06F 3/0338 |

OTHER PUBLICATIONS

H.-C. Chang, Y.-L. Hsu, S.-C. Yang, J.-C. Lin and Z.-H. Wu, "A Wearable Inertial Measurement System With Complementary Filter for Gait Analysis of Patients With Stroke or Parkinson's Disease," in IEEE Access, vol. 4, pp. 8442-8453, 2016, doi: 10.1109/ACCESS. 2016.2633304. (Year: 2016).*

Y.-L. Hsu et al., "Gait and Balance Analysis for Patients With Alzheimer's Disease Using an Inertial-Sensor-Based Wearable Instrument," in IEEE Journal of Biomedical and Health Informatics, vol. 18, No. 6, pp. 1822-1830, Nov. 2014, doi: 10.1109/JBHI.2014. 2325413. (Year: 2014).*

S. G. Kim, et al., "Characterization of the Fiber-Optic Goniometer for Measuring Knee Joint Angle", Sensor Letters, Aug. 1, 2015, vol. 13, No. 8, pp. 669-673.

* cited by examiner

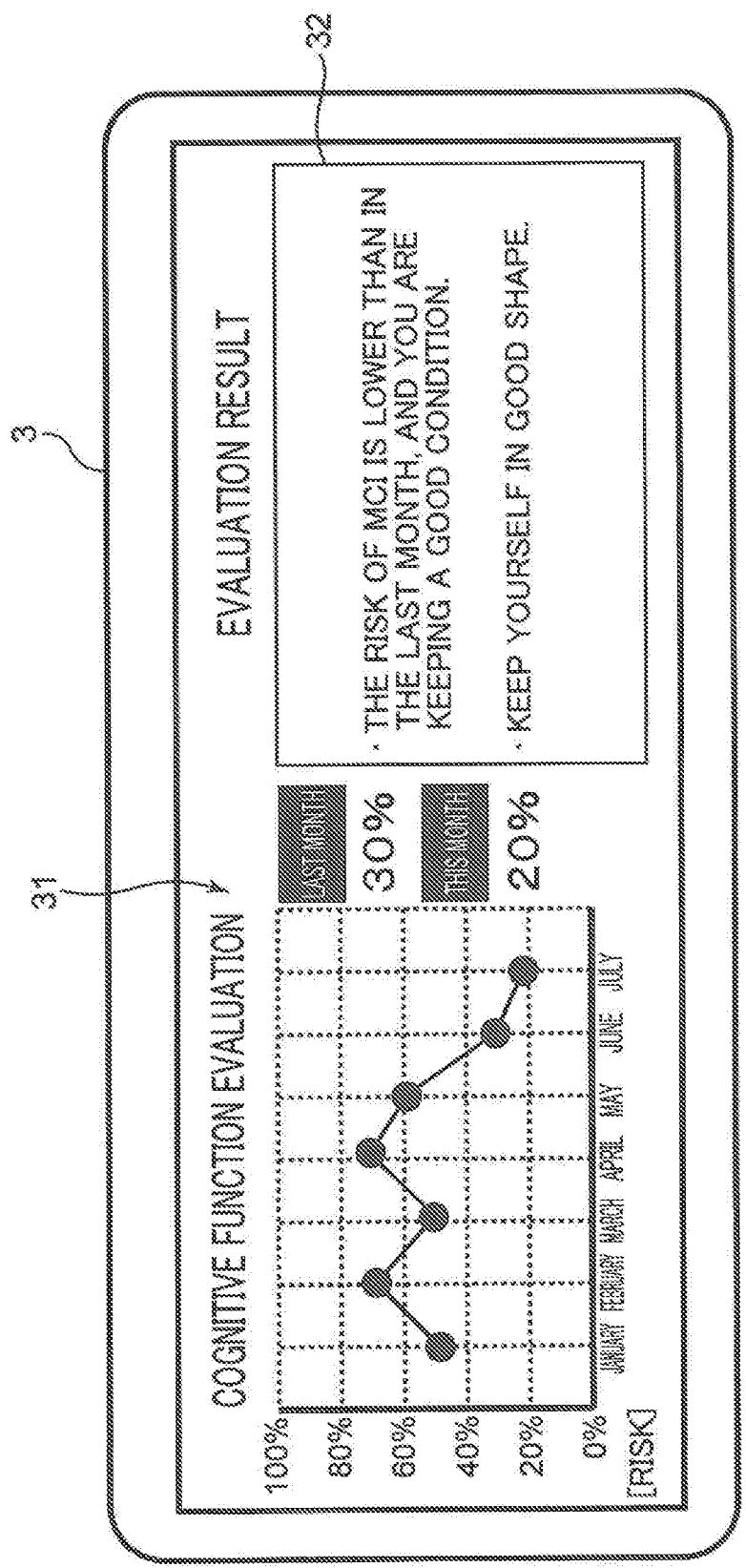

COGNITIVE FUNCTION EVALUATION METHOD, COGNITIVE FUNCTION EVALUATION DEVICE, AND NON-TRANSITORY COMPUTER-READABLE RECORDING MEDIUM IN WHICH COGNITIVE FUNCTION EVALUATION PROGRAM IS RECORDED

FIELD OF THE INVENTION

The present disclosure relates to a technology for evaluating the cognitive function based on walking motion of a subject.

BACKGROUND ART

In recent years, in order to grasp the health condition of the elderly, a technology for easily estimating a physical function has been developed.

In particular, technologies have been proposed for evaluating cognitive functions or motor functions based on parameters measured from daily walking.

For example, Japanese Patent Application Laid-Open No. 2013-255786 discloses a method for evaluating the likelihood of a senile disorder (senile disorder risk) based on walking parameters measured by walking.

A cognitive function evaluation device according to WO 2018/066422, for example, includes: storing unit storing reference data on the relationship between the periodicity of a body movement of a person walking and the cognitive function level of the person; acquiring unit that acquires body movement data on the detected body movement from body movement sensor that detects the body movement of subject walking; and calculating unit that calculates the periodicity of the body movement while walking from the acquired body movement data and checks the calculated periodicity against reference data stored in the storing unit so as to identify the cognitive function level corresponding to the calculated periodicity.

However, with the above-mentioned conventional technologies, it is difficult to easily and highly accurately evaluate the cognitive function, and further improvement has been required.

SUMMARY OF THE INVENTION

The present disclosure has been made to solve the above problems, and an object of the present disclosure is to provide a technology capable of easily and highly accurately evaluating the cognitive function.

A cognitive function evaluation method according to an aspect of the present disclosure is a cognitive function evaluation method in a cognitive function evaluation device that evaluates a cognitive function based on the walking motion of a subject, the cognitive function evaluation method including: acquiring walking data related to walking of the subject; detecting, from the walking data, at least one of an angle of an ankle joint of one foot and an angle of a knee joint of one leg of the subject; and determining a cognitive function level of the subject using at least one of the angle of the ankle joint and angle of the knee joint.

BRIEF DESCRIPTION OF THE DRAWINGS

FIG. 41 is a view showing an example of an evaluation result screen displayed in the present embodiment.

Figure 1:
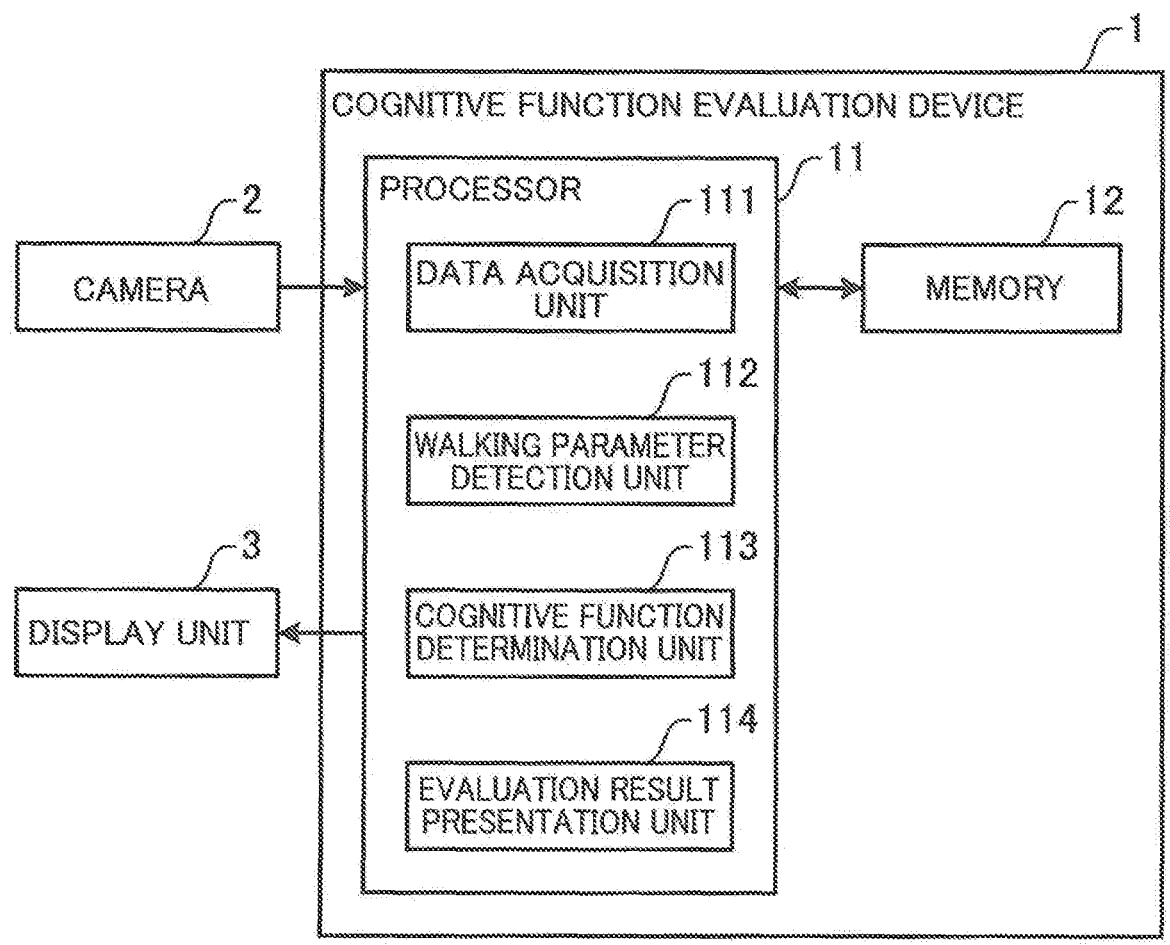
FIG. 1 is a block diagram showing a configuration of a cognitive function evaluation system in an embodiment of the present disclosure.

DESCRIPTION OF EMBODIMENTS (Findings on which the Present Disclosure is Based)

A sheet type pressure sensor or a three-dimensional motion analysis system is used for measurement of a walking parameter in Japanese Patent Application Laid-Open No. 2013-255786. The sheet type pressure sensor measures a pressure distribution at the time of walking, and measures a walking parameter from the pressure distribution. A three-dimensional motion analysis system measures a walking parameter by acquiring, from a plurality of video cameras, image information in which a marker attached on a foot is captured, and analyzing the motion from the image information. It requires a great amount of time and effort to install such a sheet type pressure sensor or a three-dimensional motion analysis system. Therefore, with Japanese Patent Application Laid-Open No. 2013-255786, it is difficult to easily evaluate the senile disorder risk.

Furthermore, walking parameters used in Japanese Patent Application Laid-Open No. 2013-255786 are two or more selected from a cadence, a stride, a walking ratio, a step, a walking interval, a walking angle, a toe angle, a stride right-and-left difference, a walking interval right-and-left difference, a walking angle right-and-left difference, and both legs support period right-and-left difference. The walking angle is an angle formed by a straight line connecting one of the right and left heels with the other heel and the travel direction. The toe angle is an angle formed by a straight line connecting the heel with the toe and the travel direction. Furthermore, in Japanese Patent Application Laid-Open No. 2013-255786, the senile disorder risk of a senile disorder selected from at least knee pain, lower back pain, incontinence of urine, dementia, and sarcopenia is evaluated. However, Japanese Patent Application Laid-Open No. 2013-255786 does not disclose evaluating a senile disorder risk using another walking parameter, and there is a possibility that the use of another walking parameter further improves the evaluation accuracy of the senile disorder risk.

The calculating unit in WO No. 2018/066422 specifies whether the subject is a normal control (NC), a mild cognitive impairment (MCI) subject, or an Alzheimer's disease (AD) subject, from an integrated value of the frequency spectrum, a step, or a time of one step. However, WO 2018/066422 does not disclose evaluating the cognitive function level using another parameter, and there is a possibility that the use of another walking parameter further improves the evaluation accuracy of the cognitive function.

In order to solve the above problems, a cognitive function evaluation method according to an aspect of the present disclosure is a cognitive function evaluation method in a cognitive function evaluation device that evaluates the cognitive function based on the walking motion of a subject, the cognitive function evaluation method including: acquiring walking data related to walking of the subject; detecting, from the walking data, at least one of an angle of an ankle joint of one foot and an angle of a knee joint of one leg of the subject; and determining a cognitive function level of the subject using at least one of the angle of the ankle joint and angle of the knee joint.

According to this configuration, at least one of the angle of the ankle joint of one foot and the angle of the knee joint of one leg of a walking subject is used as a parameter correlated with the cognitive function level of the subject. Walking motion of subjects with a cognitive function having decreased tends to be different from walking motion of subjects with a cognitive function having not decreased. In this manner, since the cognitive function level of the subject is determined using a parameter correlated with the cognitive function level of a walking subject, the cognitive function of the subject can be evaluated with high accuracy.

Furthermore, a large-scale device is unnecessary because at least one of the angle of the ankle joint of one foot and the angle of the knee joint of one leg of a walking subject can be easily detected from image data obtained by capturing an image of a walking subject, for example. Therefore, the present configuration can easily evaluate the cognitive function of the subject.

In addition, in the cognitive function evaluation method described above, in the detection, time series data of the angle of the ankle joint in a predetermined period of a swing phase of the one leg may be detected, and in the determination, the cognitive function level of the subject may be determined by using a mean value of the time series data of the angle of the ankle joint.

There is a significant difference in angle of the ankle joint in a predetermined period of the swing phase of one leg of the walking subject between subjects with a cognitive function having decreased and subjects with a cognitive function having not decreased. Therefore, according to this configuration, the cognitive function of the subject can be reliably evaluated by using a mean value of the time series data of the angle of the ankle joint in a predetermined period of the swing phase of one leg of a walking subject.

Furthermore, in the above-described cognitive function evaluation method, on the condition that a period from when one foot of the subject touches the ground to when the one foot touches the ground again is expressed as one walking cycle and the one walking cycle is expressed by 1% to 100%, the predetermined period may be a period of 81% to 100% of the one walking cycle.

According to the present configuration, the period from when one foot of the subject touches the ground to when the one foot touches the ground again is expressed as one walking cycle, and one walking cycle is expressed as 1% to 100%. At this time, the cognitive function of the subject can be reliably evaluated by using a mean value of the time series data of the angle of the ankle joint of one foot in the period of 81% to 100% of one walking cycle.

In addition, in the cognitive function evaluation method described above, the predetermined period may be a period of 85% to 88% of the one walking cycle.

According to this configuration, the cognitive function of the subject can be more reliably evaluated by using a mean value of the time series data of the angle of the ankle joint of one foot in the period of 85% to 88% of one walking cycle.

In addition, in the cognitive function evaluation method described above, in the detection, time series data of a first angle of the ankle joint in a first period of the stance phase of the one leg and time series data of a second angle of the ankle joint in a second period of the swing phase of the one leg may be detected, and in the determination, the cognitive function level of the subject may be determined by using a mean value of the time series data of the first angle of the ankle joint and a mean value of the time series data of the second angle of the ankle joint.

According to this configuration, a mean value of the time series data of the first angle of the ankle joint in the first period of the stance phase of one leg and a mean value of the time series data of the second angle of the ankle joint in the second period of the swing phase of one leg are used in combination, whereby the cognitive function can be evaluated more accurately than by using each of them in isolation.

Furthermore, in the above-described cognitive function evaluation method, on the condition that a period from when one foot of the subject touches the ground to when the one foot touches the ground again is expressed as one walking cycle and the one walking cycle is expressed by 1% to 100%, the first period may be a period of 45% to 50% of the one walking cycle, and the second period may be a period of 85% to 88% of the one walking cycle.

According to the present configuration, the period from when one foot of the subject touches the ground to when the one foot touches the ground again is expressed as one walking cycle, and one walking cycle is expressed as 1% to 100%. At this time, the cognitive function of the subject can be reliably evaluated by using a mean value of the time series data of the first angle of the ankle joint of one foot in the first period of 45% to 50% of one walking cycle and a mean value of the time series data of the second angle of the ankle joint of one foot in the second period of 85% to 88% of one walking cycle.

In addition, in the cognitive function evaluation method described above, in the detection, time series data of the angle of the knee joint in a predetermined period of the stance phase of the one leg may be detected, and in the determination, the cognitive function level of the subject may be determined by using a mean value of the time series data of the angle of the knee joint.

There is a significant difference in angle of the knee joint in a predetermined period of the stance phase of one leg between subjects with a cognitive function having decreased and subjects with a cognitive function having not decreased. Therefore, according to this configuration, the cognitive function of the subject can be reliably evaluated by using a mean value of the time series data of the angle of the knee joint in a predetermined period of the stance phase of one leg of a walking subject.

Furthermore, in the above-described cognitive function evaluation method, on the condition that a period from when one foot of the subject touches the ground to when the one foot touches the ground again is expressed as one walking cycle and the one walking cycle is expressed by 1% to 100%, the predetermined period may be a period of 41% to 50% of the one walking cycle.

According to the present configuration, the period from when one foot of the subject touches the ground to when the one foot touches the ground again is expressed as one walking cycle, and one walking cycle is expressed as 1% to 100%. At this time, the cognitive function of the subject can be reliably evaluated by using a mean value of the time series data of the angle of the knee joint of one foot in the period of 41% to 50% of one walking cycle.

In addition, in the cognitive function evaluation method described above, in the detection, time series data of the angle of the knee joint in the first period of the stance phase of the one leg and time series data of the angle of the ankle joint in the second period of the swing phase of the one leg may be detected, and in the determination, the cognitive function level of the subject may be determined by using a mean value of the time series data of the angle of the knee joint and a mean value of the time series data of the angle of the ankle joint.

According to this configuration, time series data of the angle of the knee joint in the first period of the stance phase of one leg and time series data of the angle of the ankle joint in the second period of the swing phase of one leg are detected. The cognitive function level of the subject is determined by using a mean value of the time series data of the angle of the knee joint and a mean value of the time series data of the angle of the ankle joint.

Accordingly, a mean value of the time series data of the angle of the knee joint in the first period of the stance phase of one leg and a mean value of the time series data of the angle of the ankle joint in the second period of the swing phase of one leg are used in combination, whereby the cognitive function can be evaluated more accurately than by using each of them in isolation.

Furthermore, in the above-described cognitive function evaluation method, on the condition that a period from when one foot of the subject touches the ground to when the one foot touches the ground again is expressed as one walking cycle and the one walking cycle is expressed by 1% to 100%, the first period may be a period of 41% to 50% of the one walking cycle, and the second period may be a period of 81% to 100% of the one walking cycle.

According to the present configuration, the period from when one foot of the subject touches the ground to when the one foot touches the ground again is expressed as one walking cycle, and one walking cycle is expressed as 1% to 100%. At this time, the cognitive function of the subject can be reliably evaluated by using a mean value of the time series data of the first angle of the knee joint of one foot in the first period of 41% to 50% of one walking cycle and a mean value of the time series data of the second angle of the ankle joint of one foot in the second period of 81% to 100% of one walking cycle.

In addition, the cognitive function evaluation method described above further includes detecting a vertical displacement of the waist of the subject from the walking data, in which in the determination, the cognitive function level of the subject may be determined by using at least one of the angle of the ankle joint and the angle of the knee joint, and the vertical displacement of the waist.

According to this configuration, at least one of the angle of the ankle joint and the angle of the knee joint, and the vertical displacement of the waist are used in combination, whereby the cognitive function can be evaluated more accurately than by using the vertical displacement of the waist in isolation.

In addition, the cognitive function evaluation method described above further includes recognizing a sex of the subject, in which in a case where it is recognized that the subject is male, in the detection, time series data of the angle of the ankle joint in an early stance phase of the one leg may be detected, and in the determination, the cognitive function level of the subject may be determined by using a mean value of the time series data of the angle of the ankle joint.

In the case where the subject is male, there is a significant difference in angle of the ankle joint in an early stance phase of one leg of the walking subject between subjects with a cognitive function having decreased and subjects with a cognitive function having not decreased. Therefore, according to this configuration, the cognitive function of the male subject can be reliably evaluated by using a mean value of the time series data of the angle of the ankle joint in an early stance phase of one leg of the walking subject.

In addition, in the cognitive function evaluation method described above, furthermore, the sex of the subject is recognized and in a case where it is recognized that the subject is male, in the detection, time series data of the angle of the knee joint in the swing phase of the one leg may be detected, and in the determination, the cognitive function level of the subject may be determined by using a mean value of the time series data of the angle of the knee joint.

In the case where the subject is male, there is a significant difference in angle of the knee joint in the swing phase of one leg of the walking subject between subjects with a cognitive function having decreased and subjects with a cognitive function having not decreased. Therefore, according to this configuration, the cognitive function of the male subject can be reliably evaluated by using a mean value of the time series data of the angle of the knee joint in the swing phase of one leg of the walking subject.

In addition, in the cognitive function evaluation method described above, in the determination, when the angle of the ankle joint is smaller than a threshold value or when the angle of the knee joint is smaller than a threshold value, it may be determined that the subject has mild cognitive impairment.

According to this configuration, in the case where the angle of the ankle joint is smaller than the threshold value or in the case where the angle of the knee joint is smaller than the threshold value, it is determined that the subject has mild cognitive impairment. Accordingly, by comparing the angle of the ankle joint or the angle of the knee joint with the threshold value, it is possible to easily determine whether or not the subject has mild cognitive impairment.

In addition, in the cognitive function evaluation method described above, in the determination, whether or not the subject has mild cognitive impairment may be determined by inputting at least one of the angle of the ankle joint and the angle of the knee joint that has been detected into a prediction model generated with at least one of the angle of the ankle joint and the angle of the knee joint as an input value, and with whether or not the subject has mild cognitive impairment as an output value.

According to this configuration, the prediction model is generated with at least one of the angle of the ankle joint and the angle of the knee joint as an input value, and with whether or not the subject has mild cognitive impairment as an output value. Then, whether or not the subject has mild cognitive impairment is determined by inputting, into the prediction model, at least one of the angle of the ankle joint and the angle of the knee joint that have been detected. Accordingly, it is possible to easily determine whether or not the subject has mild cognitive impairment by storing the prediction model in advance.

A cognitive function evaluation device according to another aspect of the present disclosure is a cognitive function evaluation device that evaluates cognitive function based on the walking motion of a subject, the cognitive function evaluation device including: an acquisition unit that acquires walking data related to walking of the subject; a detection unit that detects, from the walking data, at least one of an angle of an ankle joint of one foot and an angle of a knee joint of one leg of the subject; and a determination unit that determines a cognitive function level of the subject using at least one of the angle of the ankle joint and the angle of the knee joint.

According to this configuration, at least one of the angle of the ankle joint of one foot and the angle of the knee joint of one leg of a walking subject is used as a parameter correlated with the cognitive function level of the subject.

Walking motion of subjects with a cognitive function having decreased tends to be different from walking motion of subjects with a cognitive function having not decreased. In this manner, since the cognitive function level of the subject is determined using a parameter correlated with the cognitive function level of a walking subject, the cognitive function of the subject can be evaluated with high accuracy.

Furthermore, a large-scale device is unnecessary because at least one of the angle of the ankle joint of one foot and the angle of the knee joint of one leg of a walking subject can be easily detected from image data obtained by capturing an image of a walking subject, for example. Therefore, the present configuration can easily evaluate the cognitive function of the subject.

A non-transitory computer-readable recording medium in which a cognitive function evaluation program is recorded according to another aspect of the present disclosure is a non-transitory computer-readable recording medium in which the cognitive function evaluation program that evaluates the cognitive function based on walking motion of a subject is recorded, in which the non-transitory computer-readable recording medium causes a computer to function so as to acquire walking data related to walking of the subject, so as to detect, from the walking data, at least one of an angle of an ankle joint of one foot and an angle of a knee joint of one leg of the subject, and so as to determine a cognitive function level of the subject using at least one of the angle of the ankle joint and the angle of the knee joint.

According to this configuration, at least one of the angle of the ankle joint of one foot and the angle of the knee joint of one leg of a walking subject is used as a parameter correlated with the cognitive function level of the subject. Walking motion of subjects with a cognitive function having decreased tends to be different from walking motion of subjects with a cognitive function having not decreased. In this manner, since the cognitive function level of the subject is determined using a parameter correlated with the cognitive function level of a walking subject, the cognitive function of the subject can be evaluated with high accuracy.

Furthermore, a large-scale device is unnecessary because at least one of the angle of the ankle joint of one foot and the angle of the knee joint of one leg of a walking subject can be easily detected from image data obtained by capturing an image of a walking subject, for example. Therefore, the present configuration can easily evaluate the cognitive function of the subject.

An embodiment of the present disclosure will now be described with reference to the accompanying drawings. It is to be noted that the following embodiment is an example embodying the present disclosure, and does not limit the technical scope of the present disclosure.

Embodiment

A cognitive function evaluation system according to the present embodiment will be described below with reference to FIG. 1.

FIG. 1 is a block diagram showing a configuration of a cognitive function evaluation system in an embodiment of the present disclosure.

The cognitive function evaluation system shown in FIG. 1 includes a cognitive function evaluation device 1, a camera 2, and a display unit 3.

The camera 2 captures an image of a walking subject. The camera 2 outputs moving image data showing a walking subject to the cognitive function evaluation device 1. The camera 2 is connected with the cognitive function evaluation device 1 by wire or wirelessly.

The cognitive function evaluation device 1 includes a processor 11 and a memory 12.

The processor 11 is, for example, a central processing unit (CPU), and includes a data acquisition unit 111, a walking parameter detection unit 112, a cognitive function determination unit 113, and an evaluation result presentation unit 114.

The memory 12 is a storage device capable of storing various kinds of information, such as a random access memory (RAM), a hard disk drive (HDD), a solid state drive (SSD), or a flash memory.

The data acquisition unit 111 acquires walking data related to walking of the subject. The walking data is moving image data obtained by capturing an image of a walking subject, for example. The data acquisition unit 111 acquires moving image data having been output by the camera 2.

The walking parameter detection unit 112 extracts skeleton data showing the skeleton of the subject from moving image data acquired by the data acquisition unit 111. The skeleton data is represented by coordinates of a plurality of feature points indicating the joints and the like of the subject and straight lines connecting the feature points. The walking parameter detection unit 112 may use software (e.g., OpenPose or 3D-pose-baseline) that detects the coordinates of feature points of a person from two-dimensional image data.

The processing of extracting skeleton data from two-dimensional image data will now be described.

Figure 2:
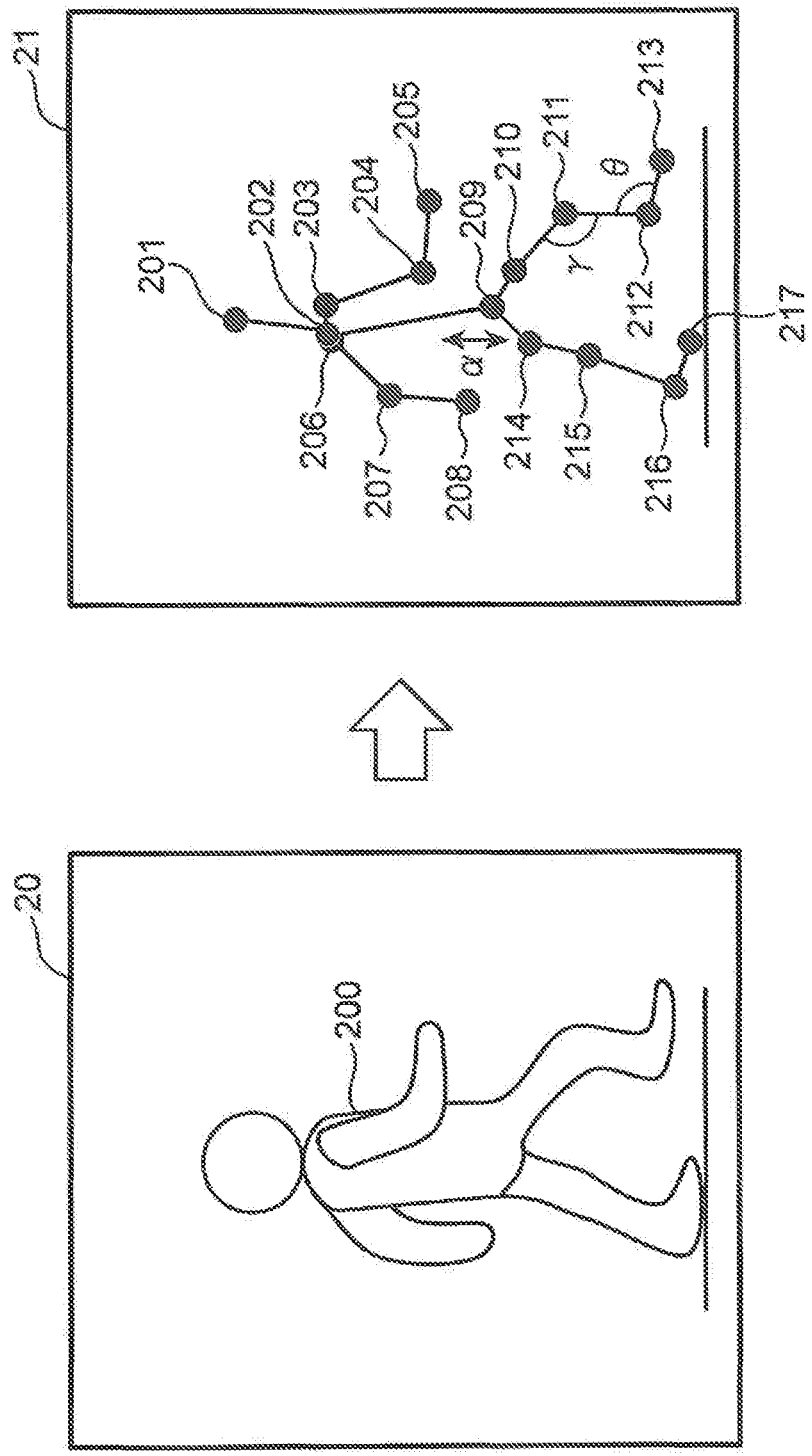
FIG. 2 is a view for explaining processing of extracting skeleton data from two-dimensional image data in the present embodiment.

FIG. 2 is a view for explaining processing of extracting skeleton data from two-dimensional image data in the present embodiment.

The walking parameter detection unit 112 extracts skeleton data 21 from two-dimensional image data 20 including an image of a walking subject 200. The skeleton data 21 includes a feature point 201 indicating the head, a feature point 202 indicating the center of both shoulders, a feature point 203 indicating the right shoulder, a feature point 204 indicating the right elbow, a feature point 205 indicating the right hand, a feature point 206 indicating the left shoulder, a feature point 207 indicating the left elbow, a feature point 208 indicating the left hand, a feature point 209 indicating the waist, a feature point 210 indicating the right hip joint, a feature point 211 indicating the right knee joint, a feature point 212 indicating the right ankle joint, a feature point 213 indicating the right toe, a feature point 214 indicating the left hip joint, a feature point 215 indicating the left knee joint, a feature point 216 indicating the left ankle joint, and a feature point 217 indicating the left toe.

The moving image data is composed of a plurality of two-dimensional image data. The walking parameter detection unit 112 extracts time series skeleton data from each of a plurality of two-dimensional image data constituting moving image data. It is to be noted that the walking parameter detection unit 112 may extract skeleton data from two-dimensional image data of all frames or may extract skeleton data from two-dimensional image data of each predetermined frame. In addition, in the present embodiment, the cognitive function level is evaluated based on the movement of mainly the lower limbs of the walking subject. Therefore, the walking parameter detection unit 112 may extract only the skeleton data of the lower limbs of the subject.

In addition, the walking parameter detection unit 112 clips skeleton data corresponding to one walking cycle of the subject from time series skeleton data extracted from moving image data. The human walking motion is a cyclic motion.

The walking cycle of the subject will now be described.

Figure 3:
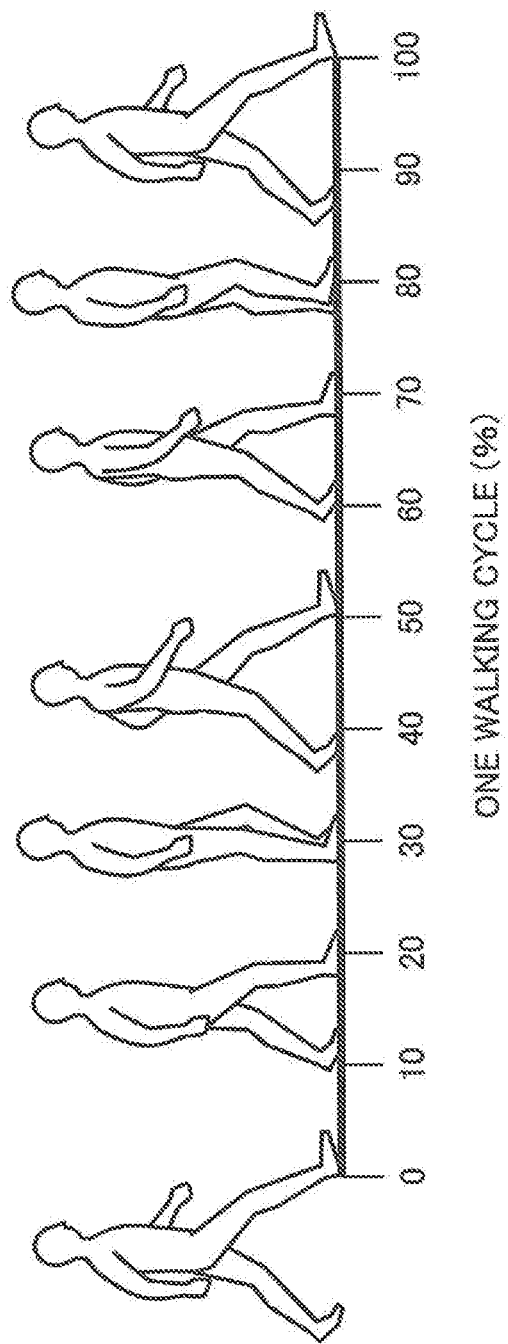
FIG. 3 is a view for explaining a walking cycle in the present embodiment.

FIG. 3 is a view for explaining a walking cycle in the present embodiment.

As shown in FIG. 3, the period from when one foot of the subject touches the ground to when the one foot touches the ground again is expressed as one walking cycle. The one walking cycle shown in FIG. 3 is a period from when the right foot of the subject touches the ground to when the right foot touches the ground again. In addition, one walking cycle is normalized to 1% to 100%. The period of 1% to 60% of one walking cycle is called a stance phase in which one foot (e.g., right foot) is on the ground, and the period of 61% to 100% of one walking cycle is called a swing phase in which one foot (e.g., right foot) is off the ground. One walking cycle includes the stance phase and the swing phase. It is to be noted that one walking cycle may be a period from when the left foot of the subject touches the ground to when the left foot touches the ground again.

The walking parameter detection unit 112 detects, from walking data, at least one of the angle of the ankle joint of one foot and the angle of the knee joint of one leg of the subject.

In the present embodiment, the walking parameter detection unit 112 detects, from walking data, the angle of the ankle joint of one foot of the subject. The walking parameter detection unit 112 detects the angle of the ankle joint of one foot of the subject from the time series skeleton data corresponding to the one walking cycle having been clipped. As shown in FIG. 2, an angle θ of the ankle joint is an angle formed in the sagittal plane by a straight line connecting the feature point 212 indicating the right ankle joint and the feature point 211 indicating the right knee joint and a straight line connecting the feature point 212 indicating the right ankle joint and the feature point 213 indicating the right toe.

In particular, the walking parameter detection unit 112 detects time series data of the angle of the ankle joint in a predetermined period of the swing phase of one leg. More specifically, the predetermined period is a period of 81% to 100% of one walking cycle. In addition, the predetermined period may be a period of 85% to 88% of one walking cycle. The walking parameter detection unit 112 calculates, as a walking parameter, a mean value of the time series data of the angle of the ankle joint in a predetermined period of the swing phase of one leg.

It is to be noted that in the present embodiment, since the one walking cycle is a period from when the right foot of the subject touches the ground to when the right foot of the subject touches the ground again, the walking parameter detection unit 112 detects the angle θ of the ankle joint of the right foot. In a case where one walking cycle is a period from when the left foot of the subject touches the ground to when the left foot touches the ground again, the walking parameter detection unit 112 may detect the angle θ of the ankle joint of the left foot.

In addition, detection of an angle of the knee joint of one leg of the subject will be described in modifications of the present embodiment.

The cognitive function determination unit 113 determines the cognitive function level of the subject using at least one of the angle of the ankle joint and the angle of the knee joint.

In the present embodiment, the cognitive function determination unit 113 determines the cognitive function level of the subject using the angle of the ankle joint. The cognitive function determination unit 113 determines whether or not the subject has mild cognitive impairment by inputting the angle of the ankle joint detected by the walking parameter detection unit 112 into the prediction model generated with the angle of the ankle joint as an input value and with whether or not the subject has mild cognitive impairment as an output value.

It is to be noted that determination of the cognitive function level of the subject using the angle of the knee joint will be described in modifications of the present embodiment.

The memory 12 stores in advance a prediction model generated with the angle of the ankle joint as an input value and with whether or not the subject has mild cognitive impairment as an output value. The prediction model is a regression model with whether or not the subject has mild cognitive impairment as an objective variable, and with the time series data of the angle of the ankle joint of one walking cycle an explanatory variable. The prediction model outputs either a value indicating that the subject has mild cognitive impairment (for example, 1) or a value indicating that the subject does not have mild cognitive impairment (for example, 0).

In particular, the cognitive function determination unit 113 determines the cognitive function level of the subject using the mean value of the time series data of the angle of the ankle joint in a predetermined period of the swing phase of one leg. More specifically, the cognitive function determination unit 113 determines the cognitive function level of the subject using the mean value of the time series data of the angle of the ankle joint of one foot in the period of 81% to 100% of one walking cycle. In addition, the cognitive function determination unit 113 may determine the cognitive function level of the subject using the mean value of the time series data of the angle of the ankle joint of one foot in the period of 85% to 88% of one walking cycle.

It is to be noted that the prediction model may be generated by machine learning. The machine learning includes, for example, supervised learning for learning the relationship between input and output by using training data in which a label (output information) is given to input information, unsupervised learning for constructing a structure of data only from an unlabeled input, semi-supervised learning for handling both the labeled and the unlabeled, and reinforcement learning for learning, on a trial-and-error basis, a behavior that maximizes reward. Specific methods of machine learning include a neural network (including deep learning using a multilayer neural network), genetic programming, a decision tree, a Bayesian network, and support vector machine (SVM). In the machine learning of the present disclosure, any of the above specific examples may be used.

In addition, the prediction model may output a value indicating the cognitive function level. The value indicating the cognitive function level is represented by 0.0 to 1.0, for example. In that case, for example, the cognitive function determination unit 113 may determine that the subject does not have mild cognitive impairment when the value indicating the cognitive function level is equal to or less than 0.5, and determine that the subject has mild cognitive impairment when the value indicating the cognitive function level is larger than 0.5.

The evaluation result presentation unit 114 presents the evaluation result of the cognitive function level determined by the cognitive function determination unit 113. The evaluation result presentation unit 114 outputs to the display unit 3 the evaluation result determined by the cognitive function determination unit 113. The evaluation result is at least one of information indicating whether or not the subject has mild cognitive impairment determined by the cognitive function determination unit 113 and an evaluation message.

The display unit 3 displays the evaluation result having been output from the evaluation result presentation unit 114. The display unit 3 is, for example, a liquid crystal display panel or a light emitting element.

It is to be noted that in order to compare the value indicating the currently determined cognitive function level with the value indicating a past cognitive function level, the display unit 3 may display a graph of transition of the value indicating the cognitive function level. It is to be noted that the value indicating the past cognitive function level is stored in the memory 12 and is read from the memory 12.

It is to be noted that the cognitive function evaluation device 1 may include the camera 2 and the display unit 3. The cognitive function evaluation device 1 may include the display unit 3. The cognitive function evaluation device 1 may be a personal computer or a server.

Next, the cognitive function evaluation processing in the present embodiment will be described with reference to FIG. 4.

Figure 4:
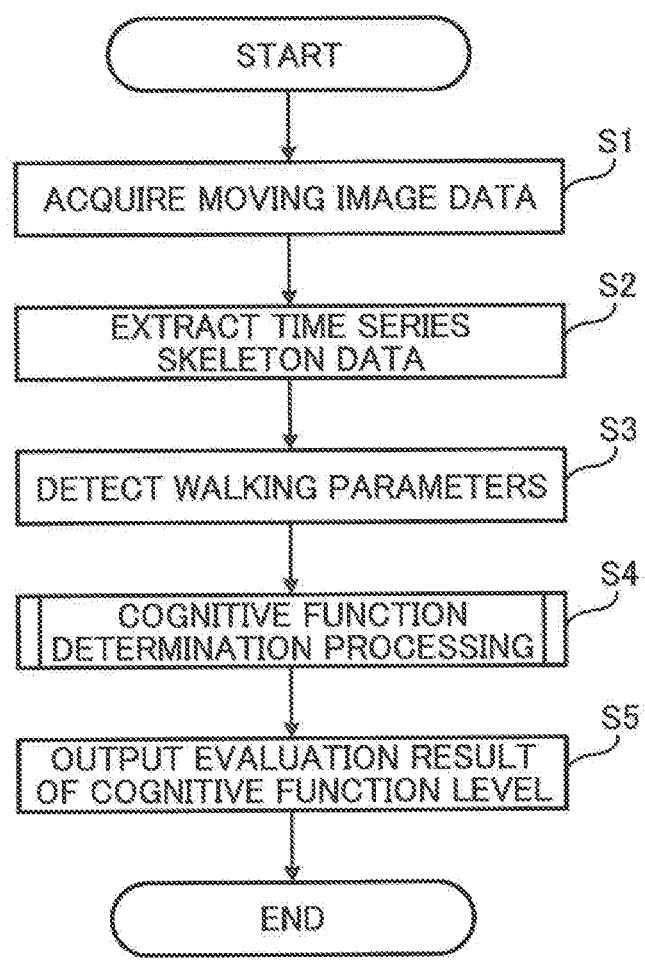
FIG. 4 is a flowchart for explaining the cognitive function evaluation processing using a walking motion of a subject in the present embodiment.

FIG. 4 is a flowchart for explaining the cognitive function evaluation processing using the walking motion of a subject in the present embodiment. The flowchart shown in FIG. 4 shows a procedure of evaluation of the cognitive function level using the cognitive function evaluation device 1.

The subject walks in front of the camera 2. The camera 2 captures an image of the walking subject. The camera 2 transmits moving image data of the walking subject to the cognitive function evaluation device 1.

First, in step S1, the data acquisition unit 111 acquires the moving image data transmitted by the camera 2.

Next, in step S2, the walking parameter detection unit 112 extracts time series skeleton data from the moving image data.

Next, in step S3, the walking parameter detection unit 112 detects a walking parameter for determining the cognitive function level from the time series skeleton data. Here, the walking parameter in the present embodiment is a mean value of the time series data of the angle of the ankle joint of one foot of the subject in a predetermined period of one walking cycle. The predetermined period is a period of 81% to 100% of one walking cycle, for example. A decision method of the walking parameter will be described later.

Next, in step S4, the cognitive function determination unit 113 executes the cognitive function determination processing for determining the cognitive function level of the subject using the walking parameter. It is to be noted that the cognitive function determination processing will be described later.

Next, in step S5, the evaluation result presentation unit 114 outputs to the display unit 3 the evaluation result of the cognitive function level determined by the cognitive function determination unit 113. The evaluation result of the cognitive function level indicates whether or not the subject has mild cognitive impairment. It is to be noted that the evaluation result presentation unit 114 may output to the display unit 3 not only the cognitive function level but also an evaluation message associated with the cognitive function level. The display unit 3 displays the evaluation result of the cognitive function level having been output from the evaluation result presentation unit 114.

The cognitive function determination processing in step S4 of FIG. 4 will now be described.

Figure 5:
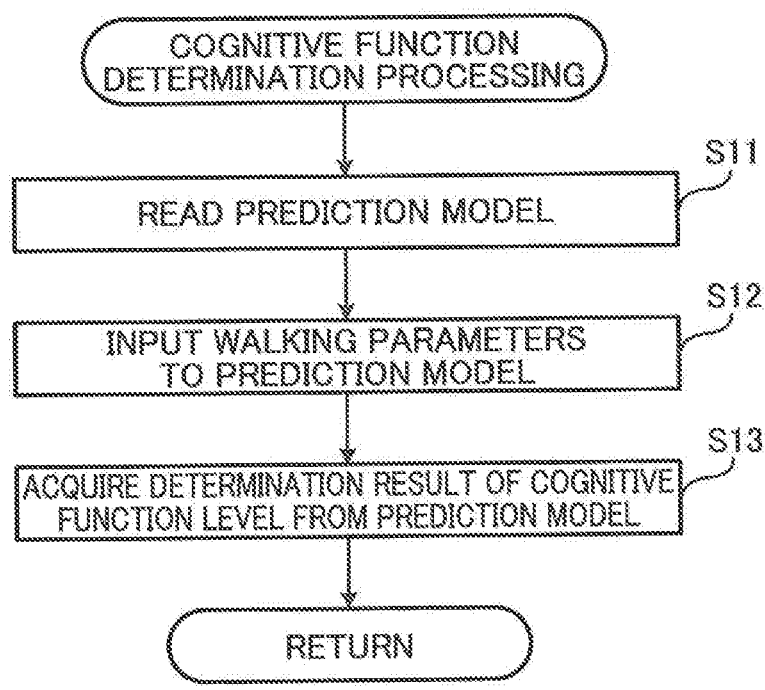
FIG. 5 is a flowchart for explaining the cognitive function determination processing in step S4 of FIG. 4.

FIG. 5 is a flowchart for explaining the cognitive function determination processing in step S4 of FIG. 4.

First, in step S11, the cognitive function determination unit 113 reads the prediction model from the memory 12.

Next, in step S12, the cognitive function determination unit 113 inputs to the prediction model the walking parameter detected by the walking parameter detection unit 112. The walking parameter in the present embodiment is a mean value of the time series data of the angle of the ankle joint of one foot of the subject in the period of 81% to 100% of one walking cycle. The cognitive function determination unit 113 inputs to the prediction model the mean value of the time series data of the angle of the ankle joint of one foot of the subject in the period of 81% to 100% of one walking cycle.

Next, in step S13, the cognitive function determination unit 113 acquires the determination result of the cognitive function level from the prediction model. The cognitive function determination unit 113 acquires whether or not the subject has mild cognitive impairment from the prediction model as a determination result.

It is to be noted that in the cognitive function determination processing of the present embodiment, by inputting a walking parameter to a prediction model generated in advance, the level of the cognitive function is determined. However, the present disclosure is not particularly limited thereto. In another example of the cognitive function determination processing of the present embodiment, the cognitive function level may be determined by comparing a threshold value stored in advance with a walking parameter.

In this case, the memory 12 stores in advance a threshold value for determining whether or not the subject has mild cognitive impairment.

In addition, the cognitive function determination unit 113 determines that the subject has mild cognitive impairment when the angle of the ankle joint is smaller than the threshold value. In the present embodiment, the cognitive function determination unit 113 determines whether or not the mean value of the time series data of the angle of the ankle joint of one foot of the subject in the period of 81% to 100% of one walking cycle is smaller than the threshold value. The cognitive function determination unit 113 determines that the subject has mild cognitive impairment when the mean value of the time series data of the angle of the ankle joint of one foot of the subject in the period of 81% to 100% of one walking cycle is smaller than the threshold value. On the other hand, the cognitive function determination unit 113 determines that the subject does not have mild cognitive impairment, i.e., the subject is a healthy subject when the mean value of the time series data of the angle of the ankle joint of one foot of the subject in the period of 81% to 100% of one walking cycle is equal to or larger than the threshold value.

Figure 6:
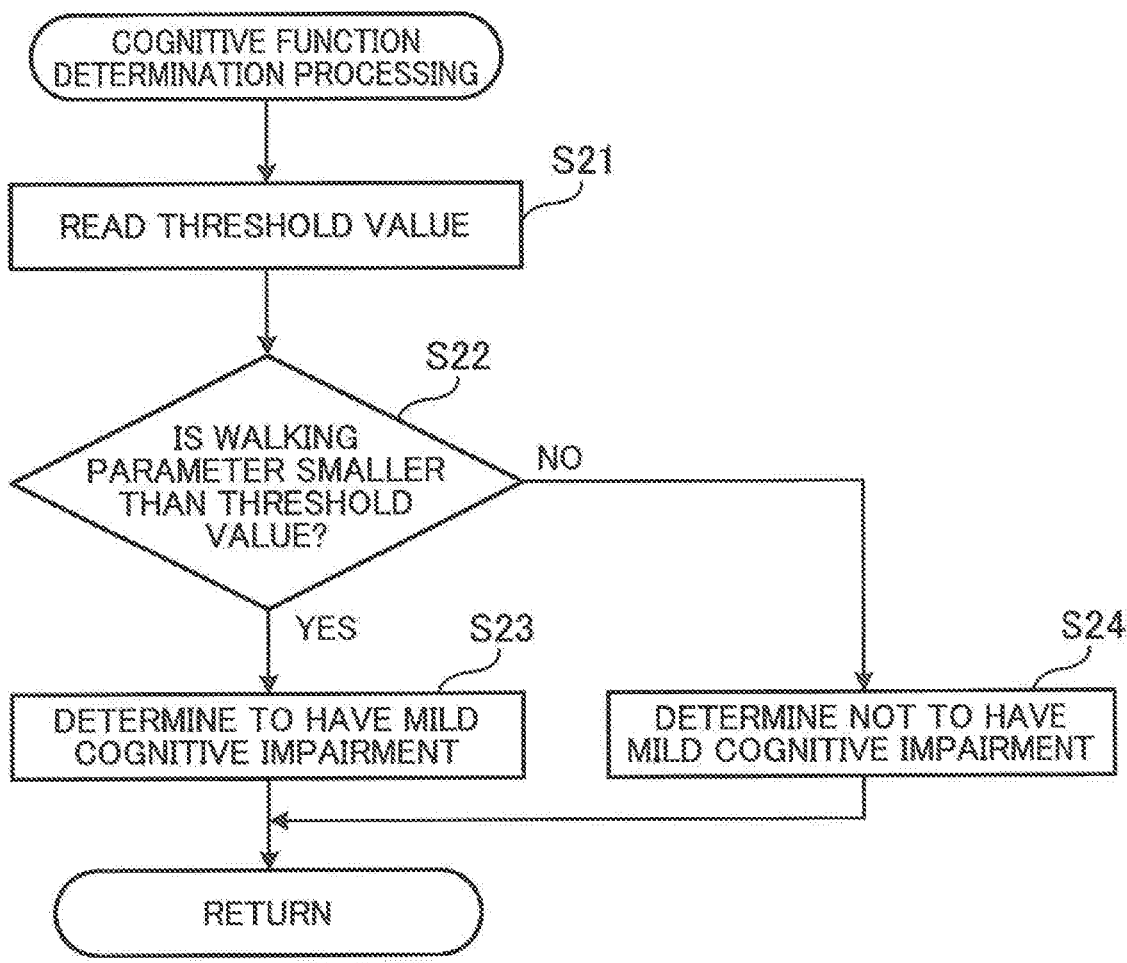
FIG. 6 is a flowchart for explaining another example of the cognitive function determination processing in step S4 of FIG. 4.

FIG. 6 is a flowchart for explaining another example of the cognitive function determination processing in step S4 of FIG. 4.

First, in step S21, the cognitive function determination unit 113 reads the threshold value from the memory 12.

Next, in step S22, the cognitive function determination unit 113 determines whether or not the walking parameter detected by the walking parameter detection unit 112 is smaller than the threshold value. The walking parameter in the present embodiment is a mean value of the time series data of the angle of the ankle joint of one foot of the subject in the period of 81% to 100% of one walking cycle. The cognitive function determination unit 113 determines whether or not the mean value of the time series data of the angle of the ankle joint of one foot of the subject in the period of 81% to 100% of one walking cycle is smaller than the threshold value.

Here, when it is determined that the walking parameter is smaller than the threshold value (YES in step S22), the cognitive function determination unit 113 determines in step S23 that the subject has mild cognitive impairment.

On the other hand, when it is determined that the walking parameter is equal to or larger than the threshold value (NO in step S22), the cognitive function determination unit 113 determines in step S24 that the subject does not have mild cognitive impairment, i.e., the subject is a healthy subject.

Thus, in the present embodiment, the angle of the ankle joint of one foot of the walking subject is a parameter correlated with the cognitive function level of the subject. Walking motion of subjects with a cognitive function having decreased tends to be different from walking motion of subjects with a cognitive function having not decreased. Therefore, the cognitive function level of the subject is determined by using a parameter correlated with the cognitive function level of the walking subject, and thus the cognitive function of the subject can be evaluated with high accuracy.

Furthermore, the angle of the ankle joint of one foot of a walking subject can be easily detected from image data obtained by capturing an image of the walking subject, for example, and hence a large-scale device is unnecessary. Therefore, the present configuration can easily evaluate the cognitive function of the subject.

It is to be noted that the cognitive function determination unit 113 may determine whether or not a difference between the maximum value and the minimum value of the angle of the ankle joint of one foot of the subject in the swing phase is smaller than the threshold value. The cognitive function determination unit 113 may determine that the subject has mild cognitive impairment when the difference between the maximum value and the minimum value of the angle of the ankle joint of one foot of the subject in the swing phase is smaller than the threshold value. On the other hand, the cognitive function determination unit 113 may determine that the subject does not have mild cognitive impairment, i.e., the subject is a healthy subject when the difference between the maximum value and the minimum value of the angle of the ankle joint of one foot of the subject in the swing phase is equal to or larger than the threshold value.

The walking parameters and the prediction models in the present embodiment are decided by experiments. Hereinafter, a decision method of a walking parameter and a prediction model in the present embodiment will be described.

The total number of subjects who participated in the experiment was 92. There were 27 male subjects and 65 female subjects. For the subjects, the Mini Mental State Examination (MMSE), which is a dementia screening examination, was conducted. Subjects with the MMSE score of 27 to 30 were determined to be healthy, and subjects with the MMSE score of 22 to 26 were determined to be suspected of having mild cognitive impairment. In this experiment, a patient with suspected mild cognitive impairment was considered as a mild cognitive impairment patient. As a result of the MMSE, 10 of the subjects had mild cognitive impairment and 82 were healthy subjects. Of the mild cognitive impairment patients, four were male and six were female. In the experiment, the subjects performed walking in front of the camera. Images of the walking subjects were captured by the camera, and the skeleton data of each subject was extracted from the moving image data. Then, time series data of the angle of one ankle joint of each subject was detected from the extracted skeleton data.

Figure 7:
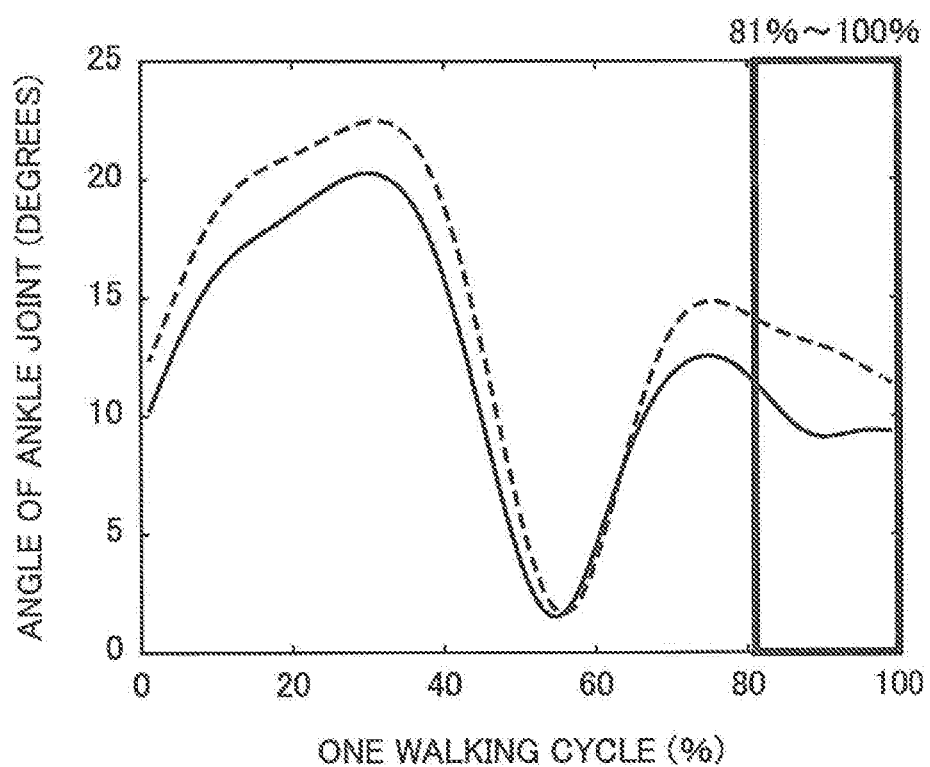
FIG. 7 is a view showing a change in the angle of one ankle joint in one walking cycle in the present embodiment.

FIG. 7 is a view showing a change in the angle of one ankle joint in one walking cycle in the present embodiment.

In FIG. 7, the vertical axis represents the angle of the ankle joint, and the horizontal axis represents one normalized walking cycle. In addition, in FIG. 7, the dashed line represents an average waveform of the angles of one ankle joint of the healthy subjects, and the solid line represents an average waveform of the angles of one ankle joint of the mild cognitive impairment patients.

In the experiment, one normalized walking cycle was divided into ten intervals, and the mean value of the angles of one ankle joint in one interval or two or more consecutive intervals was calculated for each subject. Then, a plurality of prediction models was created with whether or not the subject has mild cognitive impairment as an objective variable and with the mean value of the angles of one ankle joint in one interval or two or more consecutive intervals as an explanatory variable. The plurality of prediction models was evaluated by cross validation. Leave-one-out cross validation was adopted as the cross validation. Then, a receiver operating characteristic (ROC) curve of each of the plurality of prediction models was calculated. Furthermore, an area under curve (AUC) value of the ROC curve of each of the plurality of prediction models was calculated, and the prediction model with the highest AUC value was selected.

In the present embodiment, the prediction model created with the mean value of the angles of one ankle joint in the period of 81% to 100% of one walking cycle as the explanatory variable had the highest AUC value.

Figure 8:
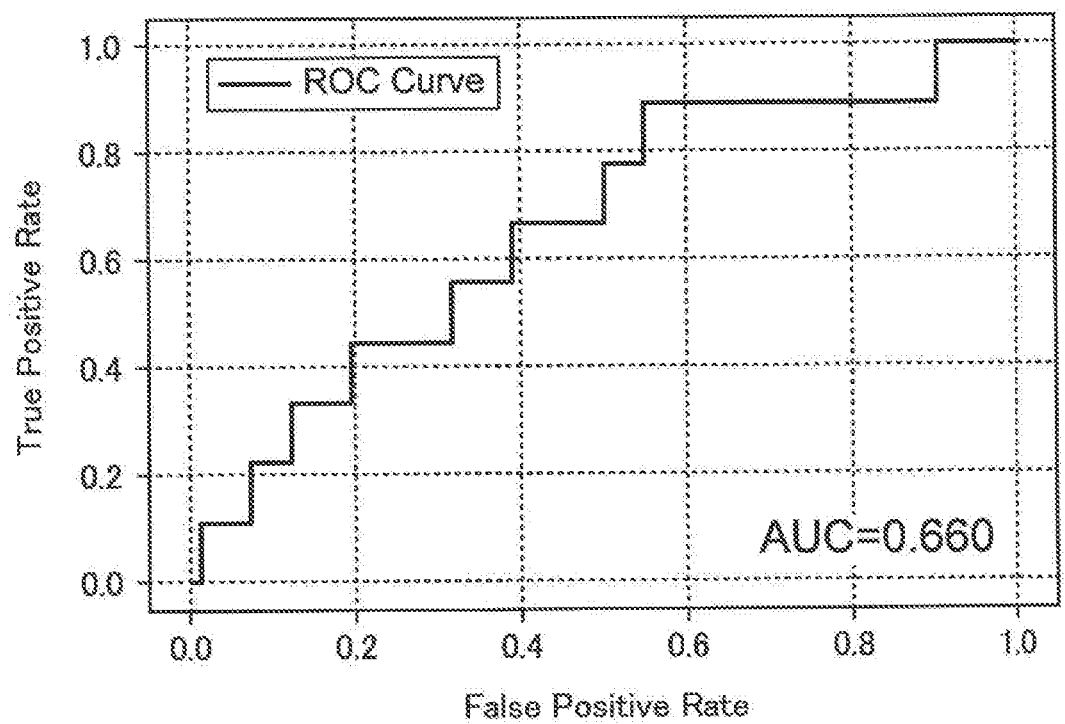
FIG. 8 is a view showing an ROC curve obtained as a result of determining a healthy subject and a mild cognitive impairment subject using a prediction model in the present embodiment.

FIG. 8 is a view showing an ROC curve obtained as a result of determining a healthy subject and a mild cognitive impairment subject using the prediction model in the present embodiment.

The prediction model in the present embodiment was created with whether or not the subject has mild cognitive impairment as an objective variable, and with the mean value of the angles of one ankle joint in the period of 81% to 100% of one walking cycle as an explanatory variable. In FIG. 8, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 8 was obtained by plotting the true positive rate and the false positive rate of the prediction model created with the mean value of the angles of the ankle joint in the period of 81% to 100% of one walking cycle as an explanatory variable. The AUC value of the ROC curve shown in FIG. 8 was 0.660. The AUC value is the area below the ROC curve. It is true that the larger the AUC value is (the more it approaches 1), the higher the performance of the prediction model is. In this case, the mean value of the angles of the ankle joint in the period of 81% to 100% of one walking cycle is determined as a walking parameter. In addition, the prediction model created with the mean value of the angles of the ankle joint in the period of 81% to 100% of one walking cycle as the explanatory variable is determined as the prediction model used by the cognitive function determination unit 113.

The memory 12 stores in advance a prediction model generated with the mean value of the time series data of the angle of the ankle joint of one foot in the period of 81% to 100% of one walking cycle as an input value, and with whether or not the subject has mild cognitive impairment as an output value. The walking parameter detection unit 112 detects time series data of the angle of the ankle joint of one foot in the period of 81% to 100% of one walking cycle. By inputting the mean value of the time series data of the angle of the ankle joint of one foot in the period of 81% to 100% of one walking cycle into the prediction model, the cognitive function determination unit 113 acquires, from the prediction model, a determination result indicating whether or not the subject has mild cognitive impairment.

In addition, in the period of 81% to 100% of one walking cycle shown in FIG. 7, the time series data of the angle of the ankle joint of one foot of mild cognitive impairment patients is smaller than the time series data of the angle of the ankle joint of one foot of healthy subjects. Therefore, a value between the average of the mean values of time series data of the angle of the ankle joint of one foot in the period of 81% to 100% of one walking cycle of the mild cognitive impairment patients and the average of the mean values of time series data of the angle of the ankle joint of one foot in the period of 81% to 100% of one walking cycle of the healthy subjects, having been experimentally obtained, may be stored in the memory 12 as the threshold value. The cognitive function determination unit 113 may determine the cognitive function level by comparing the mean value of the time series data of the angle of the ankle joint of one foot in the period of 81% to 100% of one walking cycle with the threshold value stored in advance.

It is to be noted that while in the present embodiment, the walking parameter is a mean value of the time series data of the angle of the ankle joint of one foot in the period of 81% to 100% of one walking cycle, the present disclosure is not particularly limited thereto. Various examples of the walking parameters of the present embodiment will be described below.

First, the walking parameters in the first modification of the present embodiment will be described.

The walking parameter in the first modification of the present embodiment may be a mean value of the time series data of the angle of the ankle joint of one foot in the period of 85% to 88% of one walking cycle.

Figure 9:
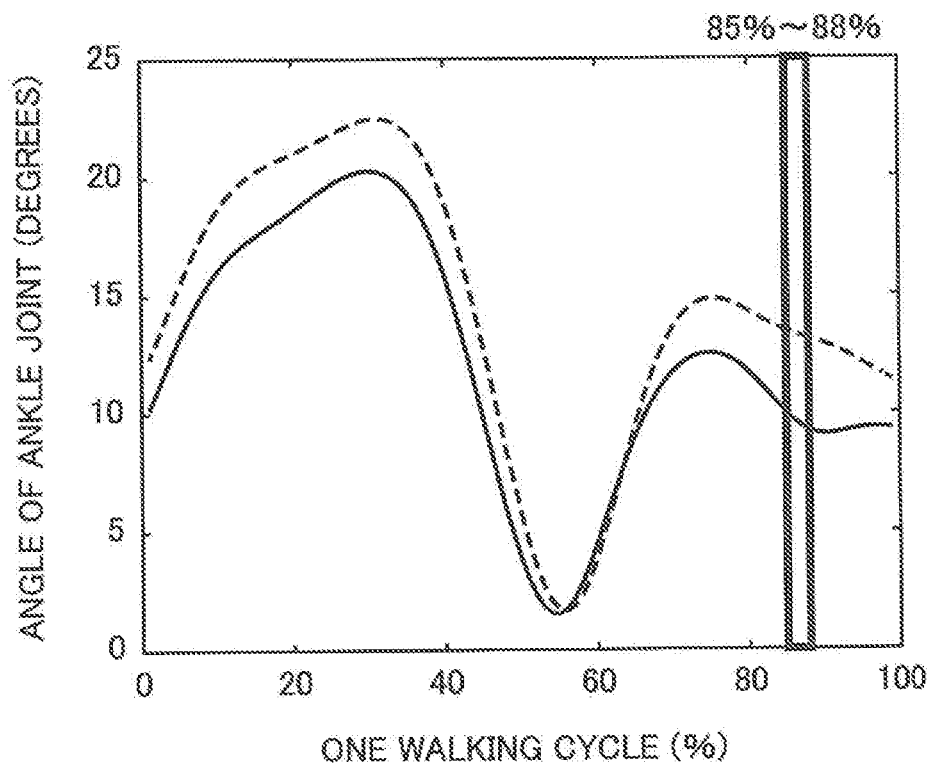
FIG. 9 is a view showing a change in the angle of one ankle joint in one walking cycle in a first modification of the present embodiment.

FIG. 9 is a view showing a change in the angle of one ankle joint in one walking cycle in the first modification of the present embodiment. In FIG. 9, the vertical axis represents the angle of the ankle joint, and the horizontal axis represents one normalized walking cycle. In addition, in FIG. 9, the dashed line represents an average waveform of the angles of one ankle joint of the healthy subjects, and the solid line represents an average waveform of the angles of one ankle joint of the mild cognitive impairment patients.

In the first modification of the present embodiment, similar to the above experiment, time series data of the angle of one ankle joint of each of the plurality of subjects was detected. In addition, a prediction model was created with whether or not the subject has mild cognitive impairment as an objective variable and with the mean value of the angles of one ankle joint in the period of 85% to 88% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 10:
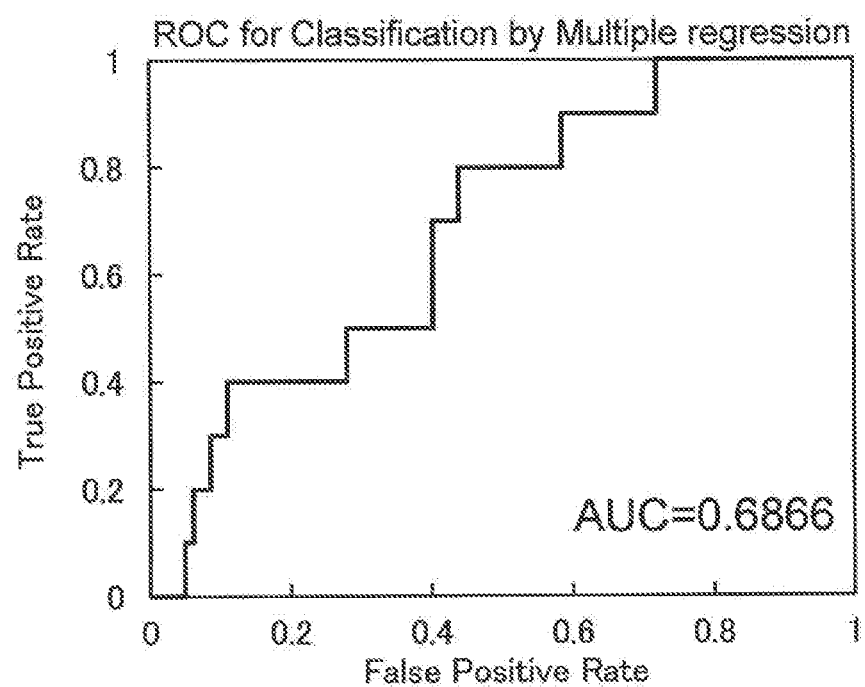
FIG. 10 is a view showing an ROC curve obtained as a result of determining a healthy subject and a mild cognitive impairment subject using a prediction model in the first modification of the present embodiment.

FIG. 10 is a view showing an ROC curve obtained as a result of determining a healthy subject and a mild cognitive impairment subject using a prediction model in the first modification of the present embodiment.

The prediction model in the first modification of the present embodiment was created with whether or not the subject has mild cognitive impairment as an objective variable, and with the mean value of the angles of one ankle joint in the period of 85% to 88% of one walking cycle as an explanatory variable. In FIG. 10, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 10 was obtained by plotting the true positive rate and the false positive rate of the prediction model created with the mean value of the angles of the ankle joint in the period of 85% to 88% of one walking cycle as an explanatory variable. The AUC value of the ROC curve shown in FIG. 10 was 0.6866. In this case, the mean value of the angles of the ankle joint in the period of 85% to 88% of one walking cycle is determined as a walking parameter. In addition, the prediction model created with the mean value of the angles of the ankle joint in the period of 85% to 88% of one walking cycle as the explanatory variable is determined as the prediction model used by the cognitive function determination unit 113.

The memory 12 stores in advance a prediction model generated with the mean value of the time series data of the angle of the ankle joint of one foot in the period of 85% to 88% of one walking cycle as an input value, and with whether or not the subject has mild cognitive impairment as an output value.

The walking parameter detection unit 112 detects time series data of the angle of the ankle joint of one foot in the period of 85% to 88% of one walking cycle. In addition, the walking parameter detection unit 112 calculates the mean value of the time series data of the angle of the ankle joint of one foot in the period of 85% to 88% of one walking cycle.

The cognitive function determination unit 113 determines the cognitive function level of the subject by using the mean value of the time series data of the angle of the ankle joint of one foot in the period of 85% to 88% of one walking cycle. By inputting the mean value of the time series data of the angle of the ankle joint of one foot in the period of 85% to 88% of one walking cycle into the prediction model, the cognitive function determination unit 113 acquires, from the prediction model, a determination result indicating whether or not the subject has mild cognitive impairment.

Figure 11:
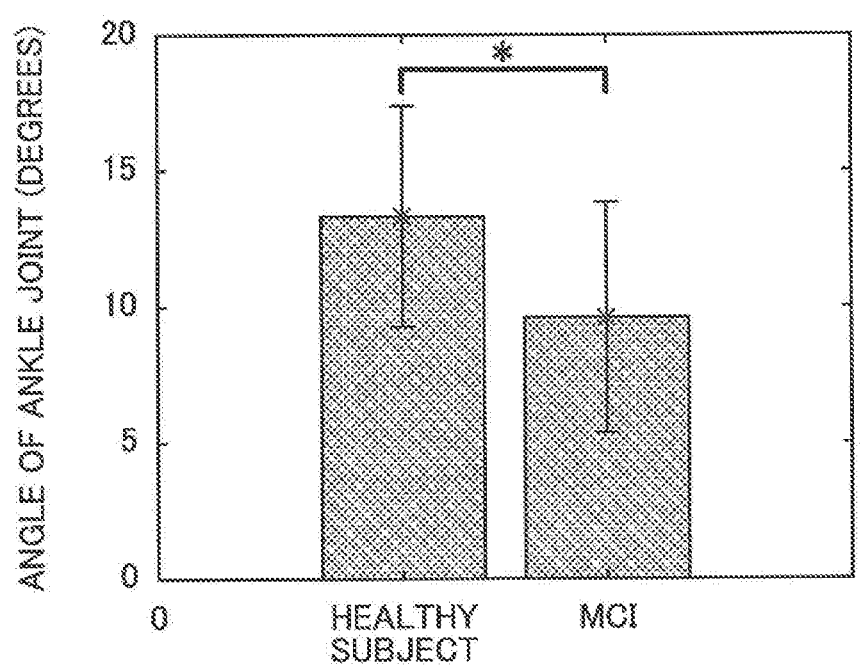
FIG. 11 is a view showing an average of mean values of time series data of the angle of one ankle joint of healthy subjects in the period of 85% to 88% of one walking cycle and an average of mean values of time series data of the angle of one ankle joint of mild cognitive impairment (MCI) patients in the period of 85% to 88% of one walking cycle in the first modification of the present embodiment.

FIG. 11 is a view showing an average of mean values of time series data of the angle of one ankle joint of healthy subjects in the period of 85% to 88% of one walking cycle and an average of mean values of time series data of the angle of one ankle joint of mild cognitive impairment (MCI) patients in the period of 85% to 88% of one walking cycle in the first modification of the present embodiment.

As shown in FIG. 11, an average of the mean values of time series data of the angle of one ankle joint of the healthy subjects in the period of 85% to 88% of one walking cycle was 13.2 degrees, and an average of the mean values of time series data of the angle of one ankle joint of the mild cognitive impairment (MCI) patients in the period of 85% to 88% of one walking cycle was 9.5 degrees.

Thus, in the period of 85% to 88% of one walking cycle, the average of the mean values of time series data of the angle of the ankle joint of one foot of the mild cognitive impairment patients is smaller than the average of the mean values of time series data of the angle of the ankle joint of one foot of the healthy subjects. Therefore, a value between the average of the mean values of time series data of the angle of the ankle joint of one foot in the period of 85% to 88% of one walking cycle of the mild cognitive impairment patients and the average of the mean values of time series data of the angle of the ankle joint of one foot in the period of 85% to 88% of one walking cycle of the healthy subjects, having been experimentally obtained, may be stored in the memory 12 as the threshold value. The cognitive function determination unit 113 may determine the cognitive function level by comparing the mean value of the time series data of the angle of one ankle joint of the subject in the period of 85% to 88% of one walking cycle with the threshold value stored in advance.

Subsequently, the walking parameters in the second modification of the present embodiment will be described.

The walking parameter in the second modification of the present embodiment may be a mean value of the time series data of the angle of the knee joint of one leg in the period of 41% to 50% of one walking cycle.

Figure 12:
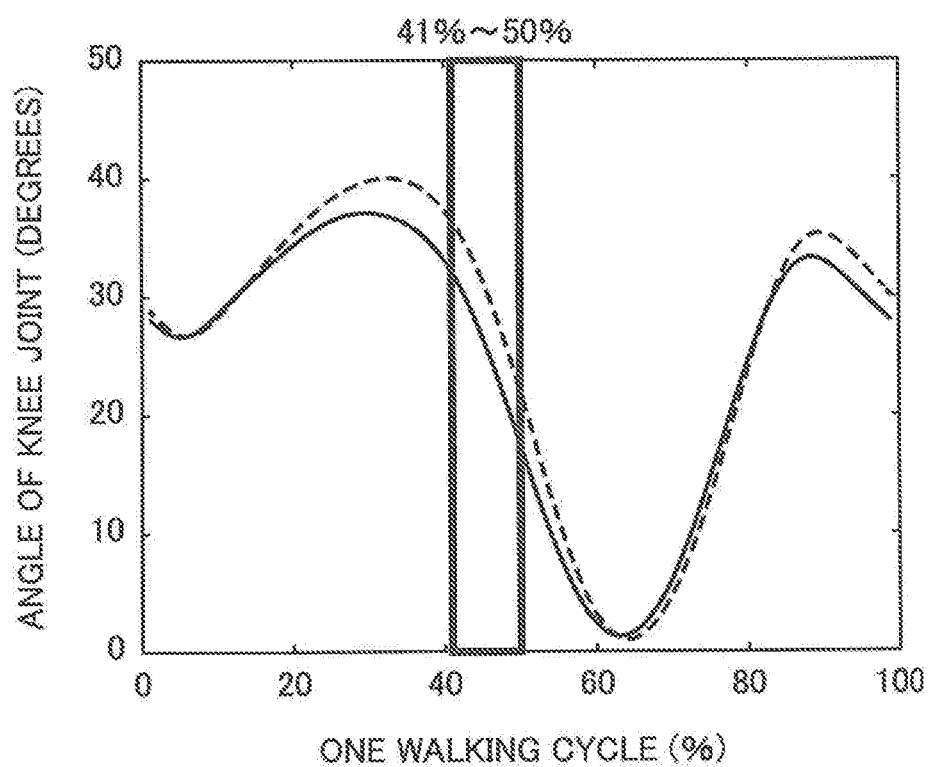
FIG. 12 is a view showing a change in the angle of one knee joint in one walking cycle in a second modification of the present embodiment.

FIG. 12 is a view showing a change in the angle of one knee joint in one walking cycle in the second modification of the present embodiment. In FIG. 12, the vertical axis represents the angle of the knee joint, and the horizontal axis represents one normalized walking cycle. In addition, in FIG. 12, the dashed line represents an average waveform of the angles of one knee joint of the healthy subjects, and the solid line represents an average waveform of the angles of one knee joint of the mild cognitive impairment patients.

In the second modification of the present embodiment, similar to the above experiment, time series data of the angle of one knee joint of each of the plurality of subjects were detected from the skeleton data of a plurality of subjects including a healthy subject and a mild cognitive impairment patient. As shown in FIG. 2, an angle γ of the knee joint is an angle formed in the sagittal plane by a straight line connecting the feature point 211 indicating the right knee joint and the feature point 210 indicating the right hip joint and a straight line connecting the feature point 211 indicating the right knee joint and the feature point 212 indicating the right ankle joint.

In the experiment, one normalized walking cycle was divided into ten intervals, and the mean value of the angles of one knee joint in one interval or two or more consecutive intervals was calculated for each subject. Then, a plurality of prediction models was created with whether or not the subject has mild cognitive impairment as an objective variable and with the mean value of the angles of one knee joint in one interval or two or more consecutive intervals as an explanatory variable. The plurality of prediction models was evaluated by cross validation. Leave-one-out cross validation was adopted as the cross validation. Then, the ROC curve of each of the plurality of prediction models was calculated. Furthermore, the AUC value of the ROC curve of each of the plurality of prediction models was calculated, and the prediction model with the highest AUC value was selected.

In the second modification of the present embodiment, the prediction model created with the mean value of the angles of one knee joint in the period of 41% to 50% of one walking cycle as the explanatory variable had the highest AUC value.

Figure 13:
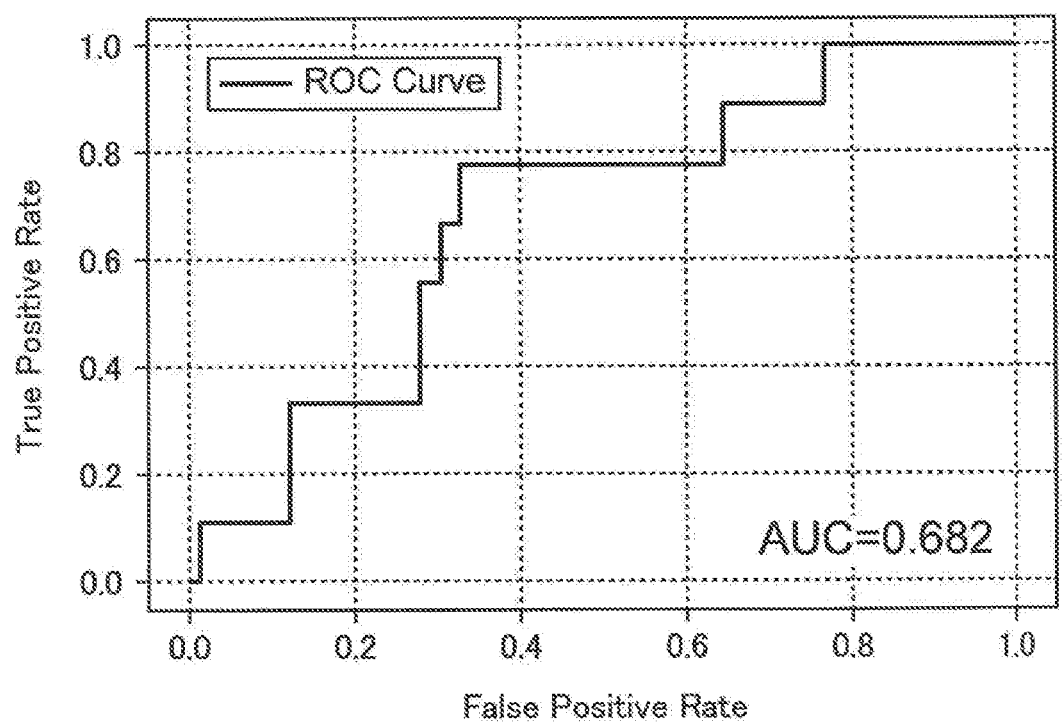
FIG. 13 is a view showing an ROC curve obtained as a result of determining a healthy subject and a mild cognitive impairment subject using a prediction model in the second modification of the present embodiment.

FIG. 13 is a view showing an ROC curve obtained as a result of determining a healthy subject and a mild cognitive impairment subject using a prediction model in the second modification of the present embodiment.

The prediction model in the second modification of the present embodiment was created with whether or not the subject has mild cognitive impairment as an objective variable, and with the mean value of the angles of one knee joint in the period of 41% to 50% of one walking cycle as an explanatory variable. In FIG. 13, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 13 was obtained by plotting the true positive rate and the false positive rate of the prediction model created with the mean value of the angles of the knee joint in the period of 41% to 50% of one walking cycle as an explanatory variable. The AUC value of the ROC curve shown in FIG. 13 was 0.682. In this case, the mean value of the angles of the knee joint in the period of 41% to 50% of one walking cycle is determined as a walking parameter. In addition, the prediction model created with the mean value of the angles of the knee joint in the period of 41% to 50% of one walking cycle as the explanatory variable is determined as the prediction model used by the cognitive function determination unit 113.

The walking parameter detection unit 112 detects, from walking data, the angle of the knee joint of one leg of the subject. The walking parameter detection unit 112 detects the angle of the knee joint of one leg of the subject from the time series skeleton data corresponding to the one walking cycle having been clipped. In particular, the walking parameter detection unit 112 detects time series data of the angle of the knee joint in a predetermined period of the stance phase of one leg. More specifically, the predetermined period is a period of 41% to 50% of one walking cycle. The walking parameter detection unit 112 detects time series data of the angle of the knee joint of one leg in the period of 41% to 50% of one walking cycle. In addition, the walking parameter detection unit 112 calculates the mean value of the time series data of the angle of the knee joint of one leg in the period of 41% to 50% of one walking cycle.

It is to be noted that in the second modification of the present embodiment, since the one walking cycle is a period from when the right foot of the subject touches the ground to when the right foot of the subject touches the ground again, the walking parameter detection unit 112 detects the angle γ of the knee joint of the right leg. In a case where one walking cycle is a period from when the left foot of the subject touches the ground to when the left foot touches the ground again, the walking parameter detection unit 112 may detect the angle γ of the knee joint of the left leg.

The cognitive function determination unit 113 determines the cognitive function level of the subject using the angle of the knee joint. The cognitive function determination unit 113 determines whether or not the subject has mild cognitive impairment by inputting the angle of the knee joint detected by the walking parameter detection unit 112 into the prediction model generated with the angle of the knee joint as an input value and with whether or not the subject has mild cognitive impairment as an output value.

The memory 12 stores in advance a prediction model generated with the angle of the knee joint as an input value and with whether or not the subject has mild cognitive impairment as an output value. The prediction model is a regression model with whether or not the subject has mild cognitive impairment as an objective variable, and with the time series data of the angle of the knee joint of one walking cycle an explanatory variable. In particular, the memory 12 stores in advance a prediction model generated with the mean value of the time series data of the angle of the knee joint of one leg in the period of 41% to 50% of one walking cycle as an input value, and with whether or not the subject has mild cognitive impairment as an output value.

In addition, the cognitive function determination unit 113 determines the cognitive function level of the subject using the mean value of the time series data of the angle of the knee joint in a predetermined period of the stance phase of one leg. More specifically, the cognitive function determination unit 113 determines the cognitive function level of the subject using the mean value of the time series data of the angle of the knee joint of one leg in the period of 41% to 50% of one walking cycle. By inputting the mean value of the time series data of the angle of the knee joint of one leg in the period of 41% to 50% of one walking cycle into the prediction model, the cognitive function determination unit 113 acquires, from the prediction model, a determination result indicating whether or not the subject has mild cognitive impairment.

In addition, in the period of 41% to 50% of one walking cycle shown in FIG. 12, the average waveform of the angles of the knee joint of one leg of the mild cognitive impairment patients is smaller than the average waveform of the angles of the knee joint of one leg of the healthy subjects. Therefore, a value between the average of the mean values of time series data of the angle of the knee joint of one leg in the period of 41% to 50% of one walking cycle of the mild cognitive impairment patients and the average of the mean values of time series data of the angle of the knee joint of one leg in the period of 41% to 50% of one walking cycle of the healthy subjects, having been experimentally obtained, may be stored in the memory 12 as the threshold value. The cognitive function determination unit 113 may determine the cognitive function level by comparing the mean value of the time series data of the angle of the knee joint of one leg of the subject in the period of 41% to 50% of one walking cycle with the threshold value stored in advance.

Subsequently, the walking parameters in the third modification of the present embodiment will be described.

The walking parameter in the third modification of the present embodiment may be a mean value of the time series data of the angle of the knee joint of one leg in the period of 45% to 49% of one walking cycle.

Figure 14:
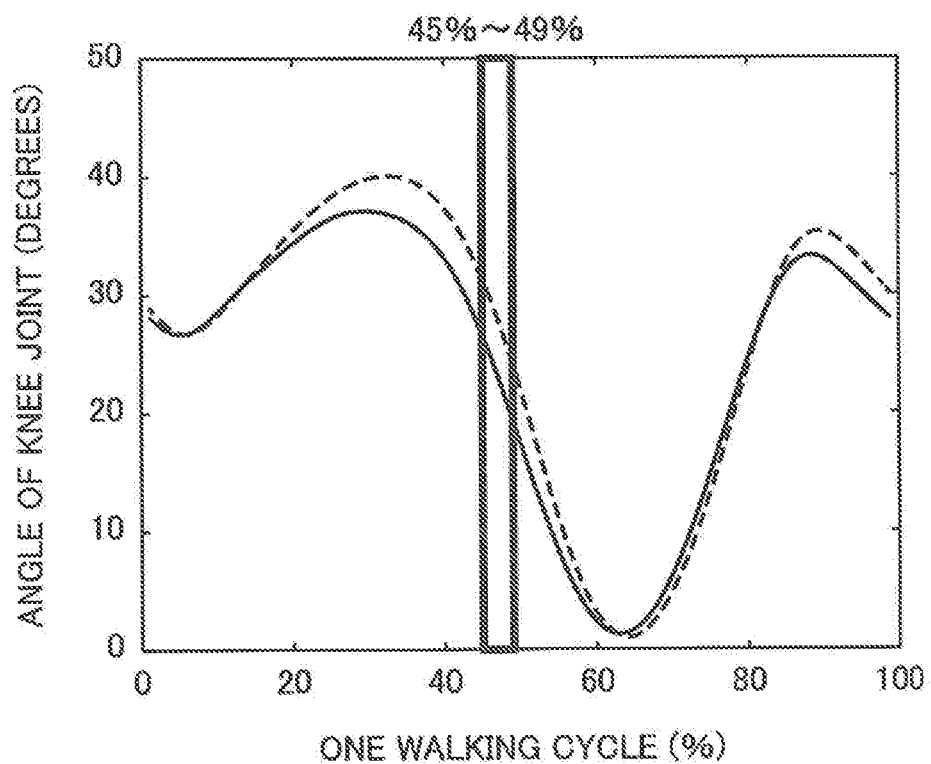
FIG. 14 is a view showing a change in the angle of one knee joint in one walking cycle in a third modification of the present embodiment.

FIG. 14 is a view showing a change in the angle of one knee joint in one walking cycle in the third modification of the present embodiment. In FIG. 14, the vertical axis represents the angle of the knee joint, and the horizontal axis represents one normalized walking cycle. In addition, in FIG. 14, the dashed line represents an average waveform of the angles of one knee joint of the healthy subjects, and the solid line represents an average waveform of the angles of one knee joint of the mild cognitive impairment patients.

In the third modification of the present embodiment, similar to the above experiment, time series data of the angle of one knee joint of each of the plurality of subjects was detected. In addition, a prediction model was created with whether or not the subject has mild cognitive impairment as an objective variable and with the mean value of the angles of one knee joint in the period of 45% to 49% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of each of the prediction models was calculated.

Figure 15:
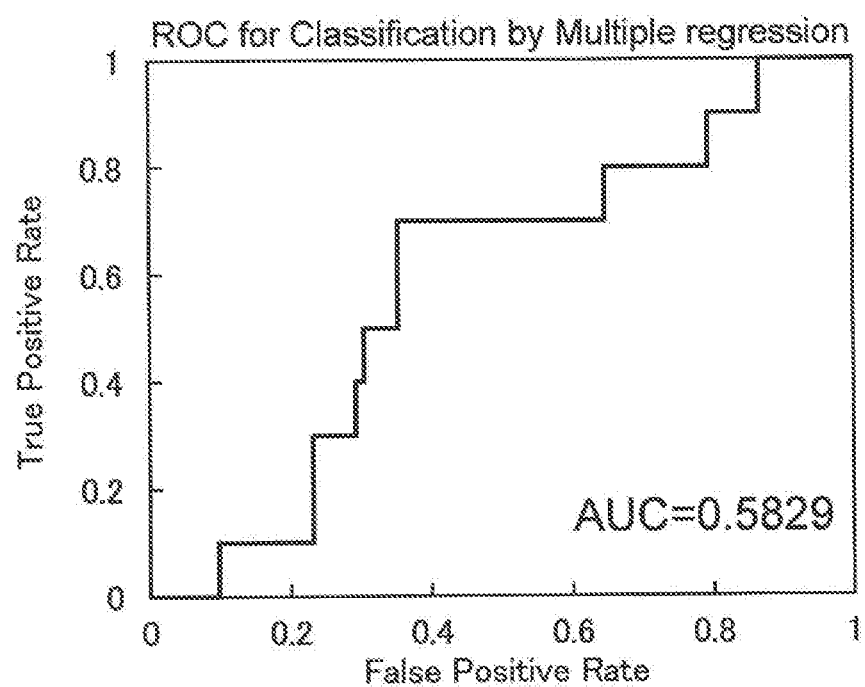
FIG. 15 is a view showing an ROC curve obtained as a result of determining a healthy subject and a mild cognitive impairment subject using a prediction model in the third modification of the present embodiment.

FIG. 15 is a view showing an ROC curve obtained as a result of determining a healthy subject and a mild cognitive impairment subject using a prediction model in the third modification of the present embodiment.

The prediction model in the third modification of the present embodiment was created with whether or not the subject has mild cognitive impairment as an objective variable, and with the mean value of the angles of one knee joint in the period of 45% to 49% of one walking cycle as an explanatory variable. In FIG. 15, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 15 was obtained by plotting the true positive rate and the false positive rate of the prediction model created with the mean value of the angles of the knee joint in the period of 45% to 49% of one walking cycle as an explanatory variable. The AUC value of the ROC curve shown in FIG. 15 was 0.5829. In this case, the mean value of the angles of the knee joint in the period of 45% to 49% of one walking cycle is determined as a walking parameter. In addition, the prediction model created with the mean value of the angles of the knee joint in the period of 45% to 49% of one walking cycle as the explanatory variable is determined as the prediction model used by the cognitive function determination unit 113.

The memory 12 stores in advance a prediction model generated with the mean value of the time series data of the angle of the knee joint of one leg in the period of 45% to 49% of one walking cycle as an input value, and with whether or not the subject has mild cognitive impairment as an output value.

The walking parameter detection unit 112 detects time series data of the angle of the knee joint of one leg in the period of 45% to 49% of one walking cycle. In addition, the walking parameter detection unit 112 calculates the mean value of the time series data of the angle of the knee joint of one leg in the period of 45% to 49% of one walking cycle.

The cognitive function determination unit 113 determines the cognitive function level of the subject by using the mean value of the time series data of the angle of the knee joint of one leg in the period of 45% to 49% of one walking cycle. By inputting the mean value of the time series data of the angle of the knee joint of one leg in the period of 45% to 49% of one walking cycle into the prediction model, the cognitive function determination unit 113 acquires, from the prediction model, a determination result indicating whether or not the subject has mild cognitive impairment.

Figure 16:
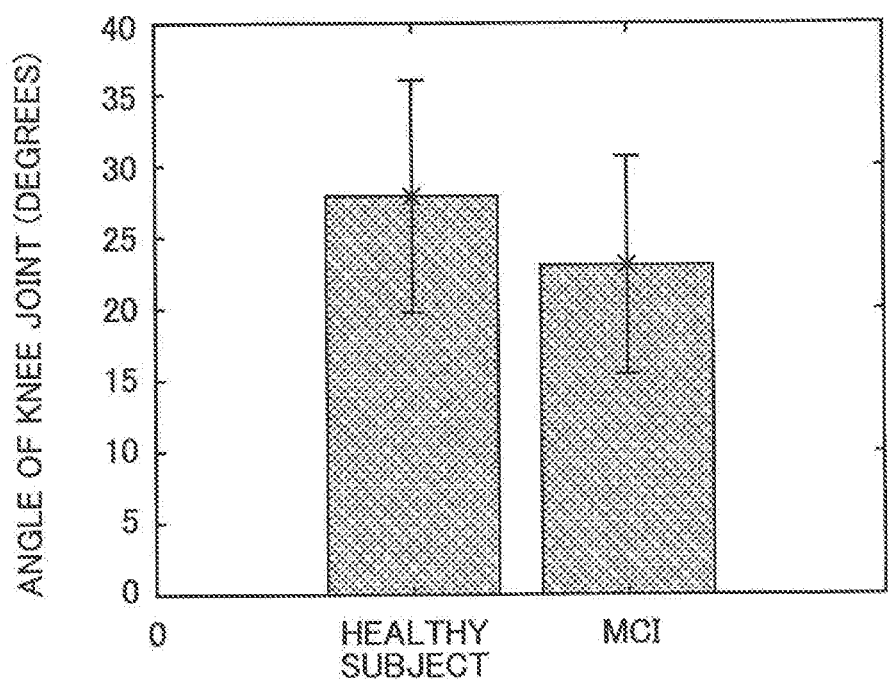
FIG. 16 is a view showing an average of mean values of time series data of the angle of one knee joint of healthy subjects in the period of 45% to 49% of one walking cycle and an average of mean values of time series data of the angle of one knee joint of mild cognitive impairment (MCI) patients in the period of 45% to 49% of one walking cycle in the third modification of the present embodiment.

FIG. 16 is a view showing an average of mean values of time series data of the angle of one knee joint of healthy subjects in the period of 45% to 49% of one walking cycle and an average of mean values of time series data of the angle of one knee joint of mild cognitive impairment (MCI) patients in the period of 45% to 49% of one walking cycle in the third modification of the present embodiment.

As shown in FIG. 16, the average of the mean values of time series data of the angle of one knee joint of the healthy subjects in the period of 45% to 49% of one walking cycle was 27.9 degrees, and the average of the mean values of time series data of the angle of one knee joint of the mild cognitive impairment (MCI) patients in the period of 45% to 49% of one walking cycle was 23.1 degrees.

Thus, in the period of 45% to 49% of one walking cycle, the average of the mean values of time series data of the angle of the knee joint of one leg of the mild cognitive impairment patients is smaller than the average of the mean values of time series data of the angle of the knee joint of one leg of the healthy subjects. Therefore, a value between the average of the mean values of time series data of the angle of the knee joint of one leg in the period of 45% to 49% of one walking cycle of the mild cognitive impairment patients and the average of the mean values of time series data of the angle of the knee joint of one leg in the period of 45% to 49% of one walking cycle of the healthy subjects, having been experimentally obtained, may be stored in the memory 12 as the threshold value. The cognitive function determination unit 113 may determine the cognitive function level by comparing the mean value of the time series data of the angle of the knee joint of one leg of the subject in the period of 45% to 49% of one walking cycle with the threshold value stored in advance.

Subsequently, the walking parameters in the fourth modification of the present embodiment will be described.

The walking parameter in the fourth modification of the present embodiment may be a mean value of time series data of the vertical displacement of the waist in the period of 21% to 30% of one walking cycle.

Figure 17:
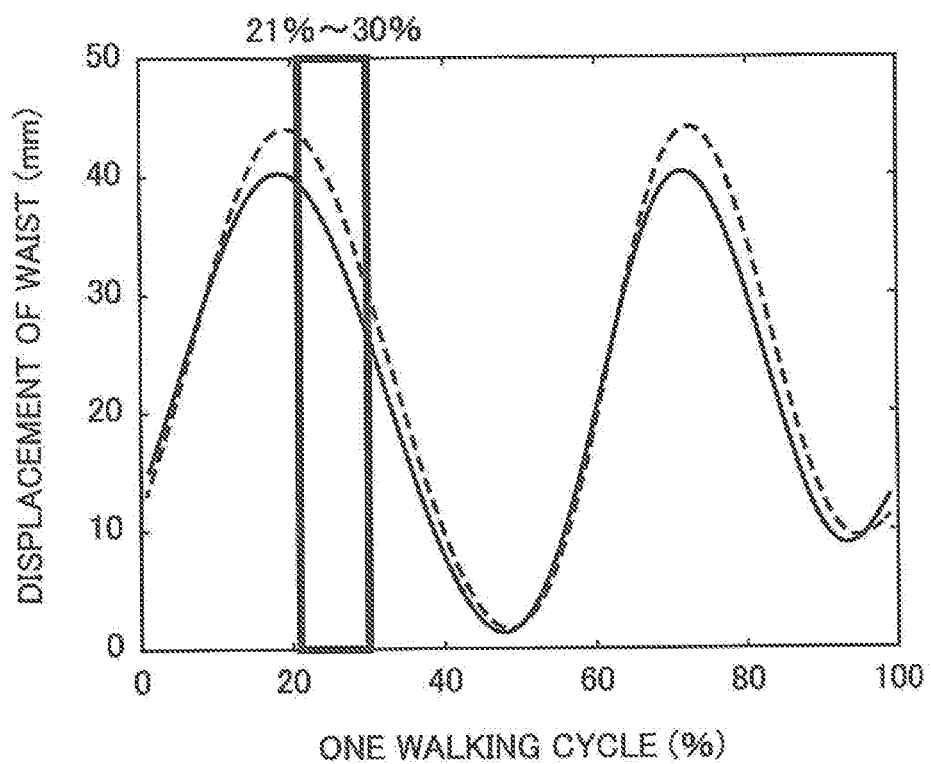
FIG. 17 is a view showing a vertical displacement of a waist in one walking cycle in a fourth modification of the present embodiment.

FIG. 17 is a view showing a vertical displacement of a waist in one walking cycle in the fourth modification of the present embodiment. In FIG. 17, the vertical axis represents the vertical displacement of the waist, and the horizontal axis represents one normalized walking cycle. In addition, in FIG. 17, the dashed line represents an average waveform of the vertical displacement of the waist of the healthy subjects, and the solid line represents an average waveform of the vertical displacement of the waist of the mild cognitive impairment patients.

In the fourth modification of the present embodiment, similar to the above experiment, time series data of the vertical displacement of the waist of each of the plurality of subjects was detected from the skeleton data of the plurality of subjects including the healthy subjects and the mild cognitive impairment patients. As shown in FIG. 2, a vertical displacement a of the waist is the vertical displacement of the feature point 209 indicating the waist.

In the experiment, one normalized walking cycle was divided into ten intervals, and the mean value of the vertical displacements of the waist in one interval or two or more consecutive intervals was calculated for each subject. Then, a plurality of prediction models was created with whether or not the subject has mild cognitive impairment as an objective variable and with the mean value of the vertical displacements of the waist in one interval or two or more consecutive intervals as an explanatory variable. The plurality of prediction models was evaluated by cross validation. Leave-one-out cross validation was adopted as the cross validation. Then, the ROC curve of each of the plurality of prediction models was calculated. Furthermore, the AUC value of the ROC curve of each of the plurality of prediction models was calculated, and the prediction model with the highest AUC value was selected.

In the fourth modification of the present embodiment, the prediction model created with the mean value of the vertical displacements of the waist in the period of 21% to 30% of one walking cycle as the explanatory variable had the highest AUC value.

Figure 18:
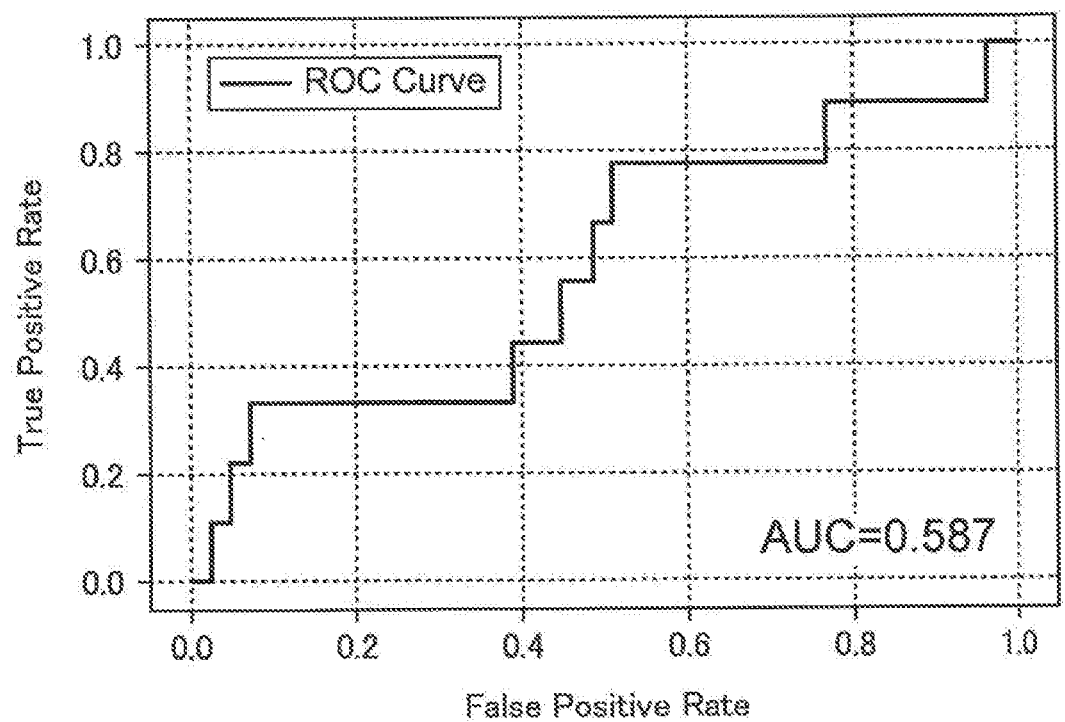
FIG. 18 is a view showing an ROC curve obtained as a result of determining a healthy subject and a mild cognitive impairment subject using a prediction model in the fourth modification of the present embodiment.

FIG. 18 is a view showing an ROC curve obtained as a result of determining a healthy subject and a mild cognitive impairment subject using a prediction model in the fourth modification of the present embodiment.

The prediction model in the fourth modification of the present embodiment was created with whether or not the subject has mild cognitive impairment as an objective variable, and with the mean value of the vertical displacements of the waist in the period of 21% to 30% of one walking cycle an explanatory variable. In FIG. 18, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 18 was obtained by plotting the true positive rate and the false positive rate of the prediction model created with the mean value of the vertical displacements of the waist in the period of 21% to 30% of one walking cycle as an explanatory variable. The AUC value of the ROC curve shown in FIG. 18 was 0.587. In this case, the mean value of the vertical displacements of the waist in the period of 21% to 30% of one walking cycle is determined as a walking parameter. In addition, the prediction model created with the mean value of the vertical displacements of the waist in the period of 21% to 30% of one walking cycle as the explanatory variable is determined as the prediction model used by the cognitive function determination unit 113.

The walking parameter detection unit 112 detects, from walking data, the vertical displacement of the waist of the subject. The walking parameter detection unit 112 detects the vertical displacement of the waist of the subject from the time series skeleton data corresponding to the one walking cycle having been clipped. In particular, the walking parameter detection unit 112 detects time series data of the vertical displacement of the waist in a predetermined period of the stance phase of one leg. More specifically, the predetermined period is a period of 21% to 30% of one walking cycle. The walking parameter detection unit 112 detects time series data of the vertical displacement of the waist in the period of 21% to 30% of one walking cycle. In addition, the walking parameter detection unit 112 calculates the mean value of time series data of the vertical displacement of the waist in the period of 21% to 30% of one walking cycle.

It is to be noted that in the fourth modification of the present embodiment, since the one walking cycle is a period from when the right foot of the subject touches the ground to when the right foot of the subject touches the ground again, the walking parameter detection unit 112 detects the vertical displacement a of the waist in the stance phase of the right leg. In a case where one walking cycle is a period from when the left foot of the subject touches the ground to when the left foot touches the ground again, the walking parameter detection unit 112 may detect the vertical displacement a of the waist in the stance phase of the left leg.

The cognitive function determination unit 113 determines the cognitive function level of the subject using the vertical displacement of the waist. The cognitive function determination unit 113 determines whether or not the subject has mild cognitive impairment by inputting the vertical displacement of the waist detected by the walking parameter detection unit 112 into the prediction model generated with the vertical displacement of the waist as an input value and with whether or not the subject has mild cognitive impairment as an output value.

The memory 12 stores in advance a prediction model generated with the vertical displacement of the waist as an input value and with whether or not the subject has mild cognitive impairment as an output value. The prediction model is a regression model with whether or not the subject has mild cognitive impairment as an objective variable, and with the time series data of the vertical displacement of the waist in the period of 21% to 30% of one walking cycle an explanatory variable. In particular, the memory 12 stores in advance a prediction model generated with the mean value of time series data of the vertical displacement of the waist in the period of 21% to 30% of one walking cycle as an input value, and with whether or not the subject has mild cognitive impairment as an output value.

In addition, the cognitive function determination unit 113 determines the cognitive function level of the subject using the mean value of time series data of the vertical displacement of the waist in a predetermined period of the stance phase of one leg. More specifically, the cognitive function determination unit 113 determines the cognitive function level of the subject using the mean value of time series data of the vertical displacement of the waist in the period of 21% to 30% of one walking cycle. By inputting the mean value of time series data of the vertical displacement of the waist in the period of 21% to 30% of one walking cycle into the prediction model, the cognitive function determination unit 113 acquires, from the prediction model, a determination result indicating whether or not the subject has mild cognitive impairment.

In addition, in the period of 21% to 30% of one walking cycle shown in FIG. 17, the average waveform of the vertical displacements of the waist of the mild cognitive impairment patients is larger than the average waveform of the vertical displacements of the waist of the healthy subjects. Therefore, a value between the average of the mean values of time series data of the vertical displacement of the waist in the period of 21% to 30% of one walking cycle of the mild cognitive impairment patients and the average of the mean values of time series data of the vertical displacement of the waist in the period of 21% to 30% of one walking cycle of the healthy subjects, having been experimentally obtained, may be stored in the memory 12 as a threshold value. The cognitive function determination unit 113 may determine the cognitive function level by comparing the mean value of time series data of the vertical displacement of the waist of the subject in the period of 21% to 30% of one walking cycle with the threshold value stored in advance.

Subsequently, the walking parameters in the fifth modification of the present embodiment will be described.

The walking parameter in the fifth modification of the present embodiment may be a mean value of the time series data of the first angle of the ankle joint in the first period of the stance phase of one leg and a mean value of the time series data of the second angle of the ankle joint in the second period of the swing phase of one leg.

Figure 19:
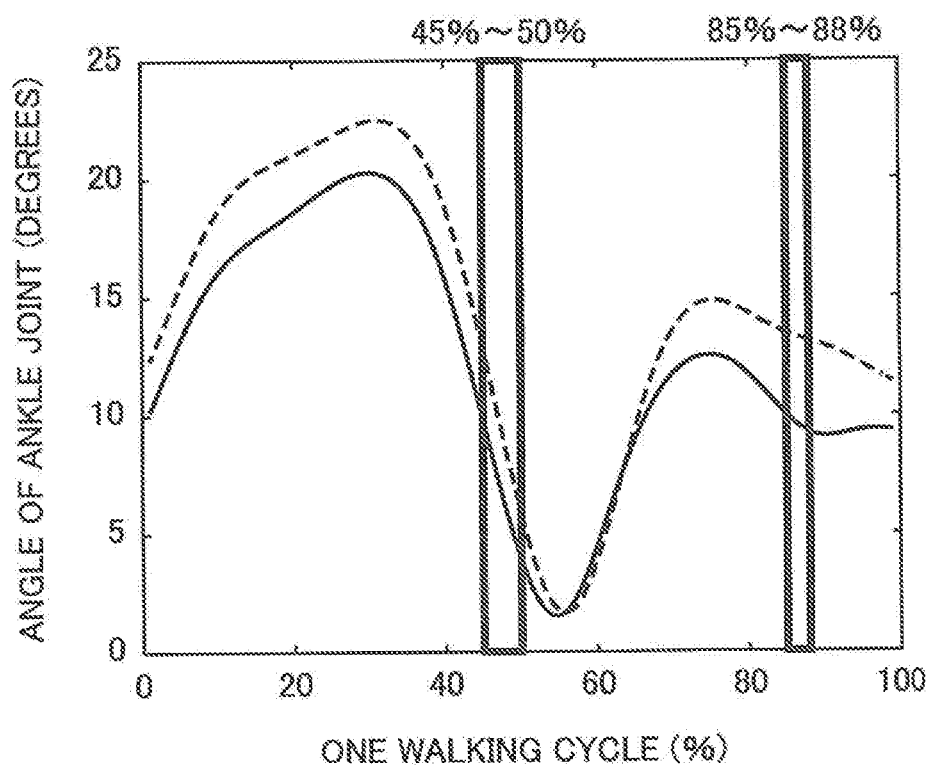
FIG. 19 is a view showing a change in the angle of one ankle joint in one walking cycle in a fifth modification of the present embodiment.

FIG. 19 is a view showing a change in the angle of one ankle joint in one walking cycle in the fifth modification of the present embodiment. In FIG. 19, the vertical axis represents the angle of the ankle joint, and the horizontal axis represents one normalized walking cycle. In addition, in FIG. 19, the dashed line represents an average waveform of the angles of one ankle joint of the healthy subjects, and the solid line represents an average waveform of the angles of one ankle joint of the mild cognitive impairment patients.

In the fifth modification of the present embodiment, similar to the above experiment, time series data of the angle of one ankle joint of each of the plurality of subjects was detected. In addition, a prediction model was created with whether or not the subject has mild cognitive impairment as an objective variable and with the mean value of the angles of one ankle joint in the period of 45% to 50% of one walking cycle and the mean value of the angles of one ankle joint in the period of 85% to 88% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 20:
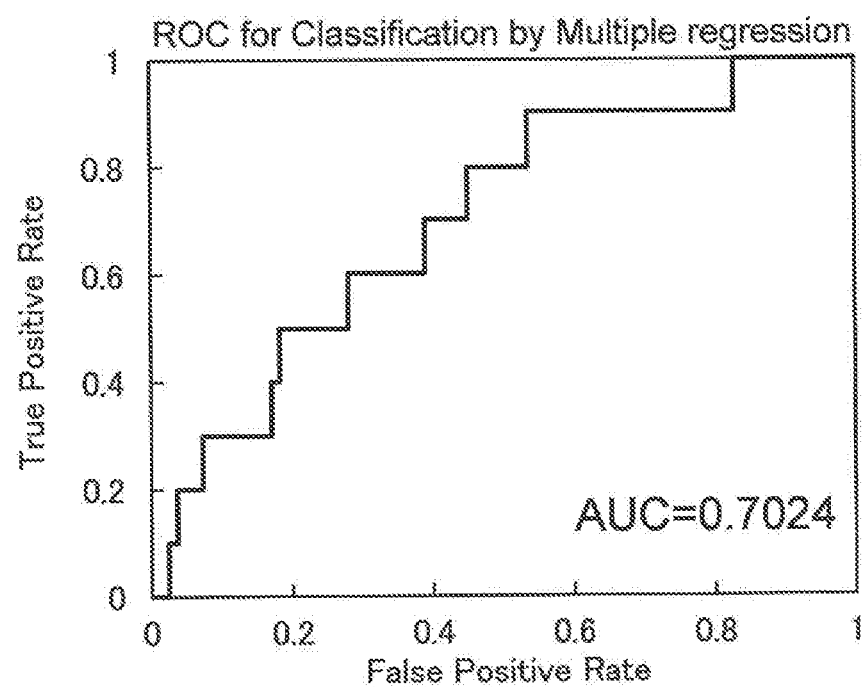
FIG. 20 is a view showing an ROC curve obtained as a result of determining a healthy subject and a mild cognitive impairment subject using a prediction model in the fifth modification of the present embodiment.

FIG. 20 is a view showing an ROC curve obtained as a result of determining a healthy subject and a mild cognitive impairment subject using a prediction model in the fifth modification of the present embodiment.

The prediction model in the fifth modification of the present embodiment was created with whether or not the subject has mild cognitive impairment as an objective variable, and with the mean value of the angles of one ankle joint in the period of 45% to 50% of one walking cycle and the mean value of the angles of one ankle joint in the period of 85% to 88% of one walking cycle as explanatory variables. In FIG. 20, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 20 was obtained by plotting the true positive rate and the false positive rate of the prediction model created with the mean value of the angles of one ankle joint in the period of 45% to 50% of one walking cycle and the mean value of the angles of one ankle joint in the period of 85% to 88% of one walking cycle as explanatory variables. The AUC value of the ROC curve shown in FIG. 20 was 0.7024. In this case, the mean value of the angles of one ankle joint in the period of 45% to 50% of one walking cycle and the mean value of the angles of one ankle joint in the period of 85% to 88% of one walking cycle are determined as walking parameters. In addition, the prediction model created with the mean value of the angles of one ankle joint in the period of 45% to 50% of one walking cycle and the mean value of the angles of one ankle joint in the period of 85% to 88% of one walking cycle as the explanatory variables is determined as the prediction model used by the cognitive function determination unit 113.

The walking parameter detection unit 112 detects time series data of the first angle of the ankle joint in the first period of the stance phase of one leg and time series data of the second angle of the ankle joint in the second period of the swing phase of one leg. The first period is a period of 45% to 50% of one walking cycle, and the second period is a period of 85% to 88% of one walking cycle. The walking parameter detection unit 112 detects time series data of the angle of one ankle joint in the period of 45% to 50% of one walking cycle and time series data of the angle of one ankle joint in the period of 85% to 88% of one walking cycle. In addition, the walking parameter detection unit 112 calculates the mean value of the time series data of the angle of one ankle joint in the period of 45% to 50% of one walking cycle and the mean value of the time series data of the angle of one ankle joint in the period of 85% to 88% of one walking cycle.

The cognitive function determination unit 113 determines the cognitive function level of the subject using the mean value of the time series data of the first angle of the ankle joint and the mean value of the time series data of the second angle.

The memory 12 stores in advance a prediction model generated with the mean value of the time series data of the first angle of the ankle joint in the first period of the stance phase of one leg and the mean value of the time series data of the second angle of the ankle joint in the second period of the swing phase of one leg as input values, and with whether or not the subject has mild cognitive impairment as an output value. The memory 12 stores in advance a prediction model generated with the mean value of the angles of one ankle joint in the period of 45% to 50% of one walking cycle and the mean value of the angles of one ankle joint in the period of 85% to 88% of one walking cycle as input values, and with whether or not the subject has mild cognitive impairment as an output value.

The cognitive function determination unit 113 determines the cognitive function level of the subject using the mean value of the time series data of the angle of one ankle joint in the period of 45% to 50% of one walking cycle and the mean value of the time series data of the angle of one ankle joint in the period of 85% to 88% of one walking cycle. By inputting the mean value of the time series data of the angle of one ankle joint in the period of 45% to 50% of one walking cycle and the mean value of the time series data of the angle of one ankle joint in the period of 85% to 88% of one walking cycle into the prediction model, the cognitive function determination unit 113 acquires, from the prediction model, a determination result indicating whether or not the subject has mild cognitive impairment.

Thus, the AUC value of the prediction model created using the mean value of the angles of the ankle joint in one period in isolation was 0.660, and the AUC value of the prediction model created using the mean value of the angles of the ankle joint in two periods was 0.7024. Accordingly, it is possible to determine the cognitive function level more accurately in the prediction model created using the mean value of the angles of the ankle joint in two periods than in the prediction model created using the mean value of the angles of the ankle joint in one period in isolation.

Subsequently, the walking parameters in the sixth modification of the present embodiment will be described.

The walking parameter in the sixth modification of the present embodiment may be a mean value of the time series data of the angle of the knee joint in the first period of the stance phase of one leg and a mean value of the time series data of the angle of the ankle joint in the second period of the swing phase of one leg.

In the sixth modification of the present embodiment, similar to the above experiment, time series data of the angle of one knee joint of each of the plurality of subjects and time series data of the angle of one ankle joint of each of the plurality of subjects were detected. In addition, a prediction model was created with whether or not the subject has mild cognitive impairment as an objective variable and with the mean value of the angles of one knee joint in the period of 41% to 50% of one walking cycle and the mean value of the angles of one ankle joint in the period of 81% to 100% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 21:
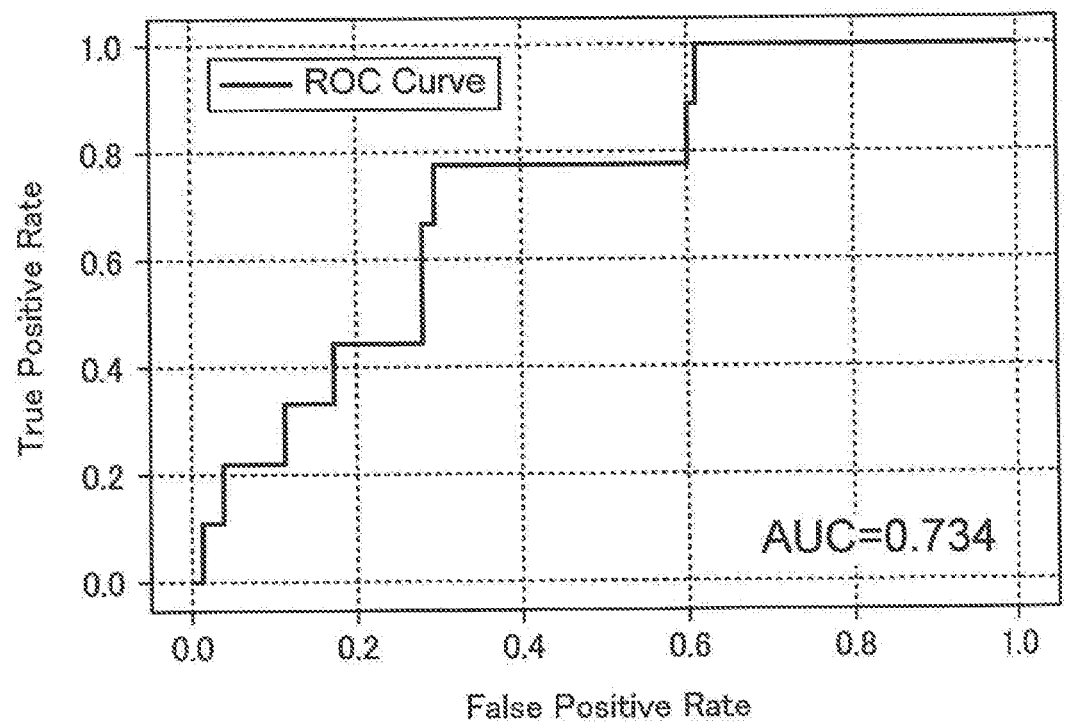
FIG. 21 is a view showing an ROC curve obtained as a result of determining a healthy subject and a mild cognitive impairment subject using a prediction model in a sixth modification of the present embodiment.

FIG. 21 is a view showing an ROC curve obtained as a result of determining a healthy subject and a mild cognitive impairment subject using a prediction model in the sixth modification of the present embodiment.

The prediction model in the sixth modification of the present embodiment was created with whether or not the subject has mild cognitive impairment as an objective variable, and with the mean value of the angles of one knee joint in the period of 41% to 50% of one walking cycle and the mean value of the angles of one ankle joint in the period of 81% to 100% of one walking cycle as explanatory variables. In FIG. 21, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 21 was obtained by plotting the true positive rate and the false positive rate of the prediction model created with the mean value of the angles of one knee joint in the period of 41% to 50% of one walking cycle and the mean value of the angles of one ankle joint in the period of 81% to 100% of one walking cycle as explanatory variables. The AUC value of the ROC curve shown in FIG. 21 was 0.734. In this case, the mean value of the angles of one knee joint in the period of 41% to 50% of one walking cycle and the mean value of the angles of one ankle joint in the period of 81% to 100% of one walking cycle are determined as walking parameters. In addition, the prediction model created with the mean value of the angles of one knee joint in the period of 41% to 50% of one walking cycle and the mean value of the angles of one ankle joint in the period of 81% to 100% of one walking cycle as the explanatory variables is determined as the prediction model used by the cognitive function determination unit 113.

The walking parameter detection unit 112 detects time series data of the angle of the knee joint in the first period of the stance phase of one leg and time series data of the angle of the ankle joint in the second period of the swing phase of one leg. The first period is a period of 41% to 50% of one walking cycle, and the second period is a period of 81% to 100% of one walking cycle. The walking parameter detection unit 112 detects time series data of the angle of one knee joint in the period of 41% to 50% of one walking cycle and time series data of the angle of one ankle joint in the period of 81% to 100% of one walking cycle. In addition, the walking parameter detection unit 112 calculates the mean value of the time series data of the angle of one knee joint in the period of 41% to 50% of one walking cycle and the mean value of the time series data of the angle of one ankle joint in the period of 81% to 100% of one walking cycle.

The cognitive function determination unit 113 determines the cognitive function level of the subject using the mean value of the time series data of the angle of the knee joint and the mean value of the time series data of the angle of the ankle joint.

The memory 12 stores in advance a prediction model generated with the mean value of the time series data of the angle of the knee joint in the first period of the stance phase of one leg and the mean value of the time series data of the angle of the ankle joint in the second period of the swing phase of one leg as input values, and with whether or not the subject has mild cognitive impairment as an output value. The memory 12 stores in advance a prediction model generated with the mean value of the angles of one knee joint in the period of 41% to 50% of one walking cycle and the mean value of the angles of one ankle joint in the period of 81% to 100% of one walking cycle as input values, and with whether or not the subject has mild cognitive impairment as an output value.

The cognitive function determination unit 113 determines the cognitive function level of the subject using the mean value of the time series data of the angle of one knee joint in the period of 41% to 50% of one walking cycle and the mean value of the time series data of the angle of one ankle joint in the period of 81% to 100% of one walking cycle. By inputting the mean value of the time series data of the angle of one knee joint in the period of 41% to 50% of one walking cycle and the mean value of the time series data of the angle of one ankle joint in the period of 81% to 100% of one walking cycle into the prediction model, the cognitive function determination unit 113 acquires, from the prediction model, a determination result indicating whether or not the subject has mild cognitive impairment.

Thus, the AUC value of the prediction model created using the angle of the ankle joint and the angle of the knee joint in isolation were 0.660 and 0.682, respectively, and the AUC value of the prediction model created using the angle of the ankle joint and the angle of the knee joint was 0.734. Accordingly, it is possible to determine the cognitive function level more accurately in the prediction model created using the angle of the ankle joint and the angle of the knee joint than in the prediction model created using each of the angle of the ankle joint and the angle of the knee joint in isolation.

Subsequently, the walking parameter in the seventh modification of the present embodiment will be described.

The walking parameter in the seventh modification of the present embodiment may be a mean value of time series data of the vertical displacement of the waist in the first period of the stance phase of one leg and a mean value of the time series data of the angle of the ankle joint in the second period of the swing phase of one leg.

In the seventh modification of the present embodiment, similar to the above experiment, time series data of the vertical displacement of the waist of each of the plurality of subjects and time series data of the angle of one ankle joint of each of the plurality of subjects were detected. In addition, a prediction model was created with whether or not the subject has mild cognitive impairment as an objective variable and with the mean value of the vertical displacements of the waist in the period of 21% to 30% of one walking cycle and the mean value of the angles of one ankle joint in the period of 81% to 100% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 22:
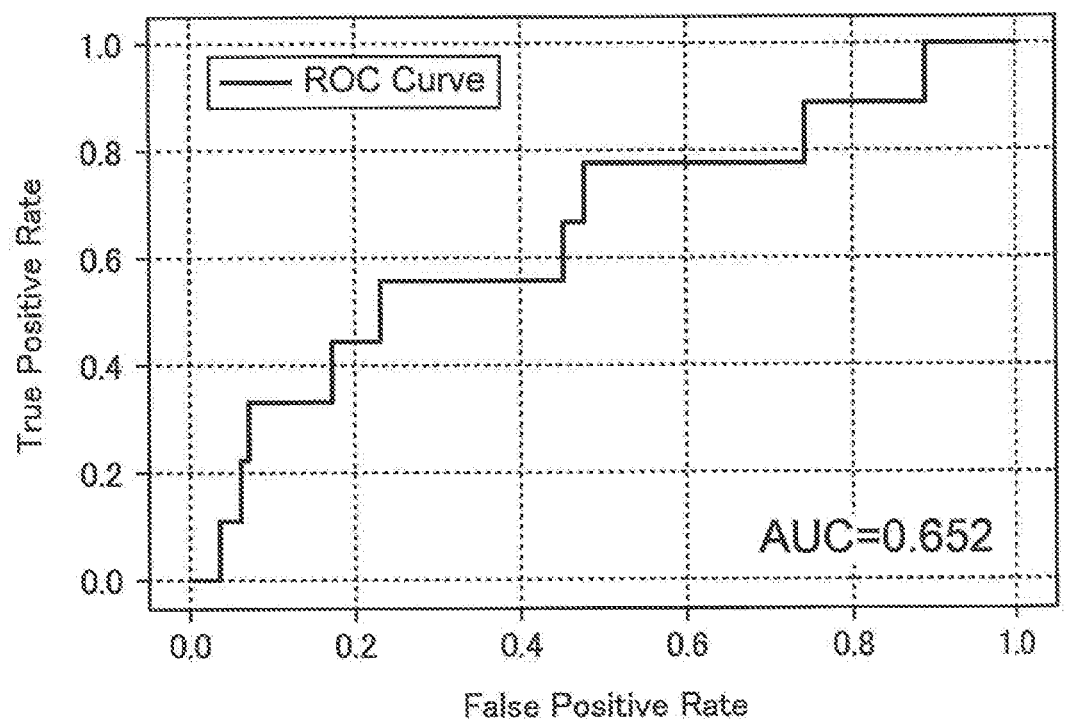
FIG. 22 is a view showing an ROC curve obtained as a result of determining a healthy subject and a mild cognitive impairment subject using a prediction model in a seventh modification of the present embodiment.

FIG. 22 is a view showing an ROC curve obtained as a result of determining a healthy subject and a mild cognitive impairment subject using a prediction model in the seventh modification of the present embodiment.

The prediction model in the seventh modification of the present embodiment was created with whether or not the subject has mild cognitive impairment as an objective variable, and with the mean value of the vertical displacements of the waist in the period of 21% to 30% of one walking cycle and the mean value of the angles of one ankle joint in the period of 81% to 100% of one walking cycle as explanatory variables. In FIG. 22, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 22 was obtained by plotting the true positive rate and the false positive rate of the prediction model created with the mean value of the vertical displacements of the waist in the period of 21% to 30% of one walking cycle and the mean value of the angles of one ankle joint in the period of 81% to 100% of one walking cycle as explanatory variables. The AUC value of the ROC curve shown in FIG. 22 was 0.652. In this case, the mean value of the vertical displacements of the waist in the period of 21% to 30% of one walking cycle and the mean value of the angles of one ankle joint in the period of 81% to 100% of one walking cycle are determined as walking parameters. In addition, the prediction model created with the mean value of the vertical displacements of the waist in the period of 21% to 30% of one walking cycle and the mean value of the angles of one ankle joint in the period of 81% to 100% of one walking cycle as the explanatory variables is determined as the prediction model used by the cognitive function determination unit 113.

The walking parameter detection unit 112 detects time series data of the vertical displacement of the waist in the first period of the stance phase of one leg and time series data of the angle of the ankle joint in the second period of the swing phase of one leg. The first period is a period of 21% to 30% of one walking cycle, and the second period is a period of 81% to 100% of one walking cycle. The walking parameter detection unit 112 detects time series data of the vertical displacement of the waist in the period of 21% to 30% of one walking cycle and time series data of the angle of one ankle joint in the period of 81% to 100% of one walking cycle. In addition, the walking parameter detection unit 112 calculates the mean value of time series data of the vertical displacement of the waist in the period of 21% to 30% of one walking cycle and the mean value of the time series data of the angle of one ankle joint in the period of 81% to 100% of one walking cycle.

The cognitive function determination unit 113 determines the cognitive function level of the subject using the mean value of time series data of the vertical displacement of the waist and the mean value of the time series data of the angle of the ankle joint.

The memory 12 stores in advance a prediction model generated with the mean value of time series data of the vertical displacement of the waist in the first period of the stance phase of one leg and the mean value of the time series data of the angle of the ankle joint in the second period of the swing phase of one leg as input values, and with whether or not the subject has mild cognitive impairment as an output value. The memory 12 stores in advance a prediction model generated with the mean value of the vertical displacements of the waist in the period of 21% to 30% of one walking cycle and the mean value of the angles of one ankle joint in the period of 81% to 100% of one walking cycle as input values, and with whether or not the subject has mild cognitive impairment as an output value.

The cognitive function determination unit 113 determines the cognitive function level of the subject using the mean value of time series data of the vertical displacement of the waist in the period of 21% to 30% of one walking cycle and the mean value of the time series data of the angle of one ankle joint in the period of 81% to 100% of one walking cycle. By inputting the mean value of time series data of the vertical displacement of the waist in the period of 21% to 30% of one walking cycle and the mean value of the time series data of the angle of one ankle joint in the period of 81% to 100% of one walking cycle into the prediction model, the cognitive function determination unit 113 acquires, from the prediction model, a determination result indicating whether or not the subject has mild cognitive impairment.

Thus, the AUC value of the prediction model created using the vertical displacement of the waist in isolation was 0.587, and the AUC value of the prediction model created using the angle of the ankle joint and the vertical displacement of the waist was 0.652. Accordingly, it is possible to determine the cognitive function level more accurately in the prediction model created using the angle of the ankle joint and the vertical displacement of the waist than in the prediction model created using the vertical displacement of the waist in isolation.

Subsequently, the walking parameters in the eighth modification of the present embodiment will be described.

The walking parameter in the eighth modification of the present embodiment may be a mean value of time series data of the vertical displacement of the waist in the first period of the stance phase of one leg and a mean value of the time series data of the angle of the knee joint in the second period of the stance phase of one leg.

In the eighth modification of the present embodiment, similar to the above experiment, time series data of the vertical displacement of the waist of each of the plurality of subjects and time series data of the angle of one knee joint of each of the plurality of subjects were detected. In addition, a prediction model was created with whether or not the subject has mild cognitive impairment as an objective variable and with the mean value of the vertical displacements of the waist in the period of 21% to 30% of one walking cycle and the mean value of the angles of one knee joint in the period of 41% to 50% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 23:
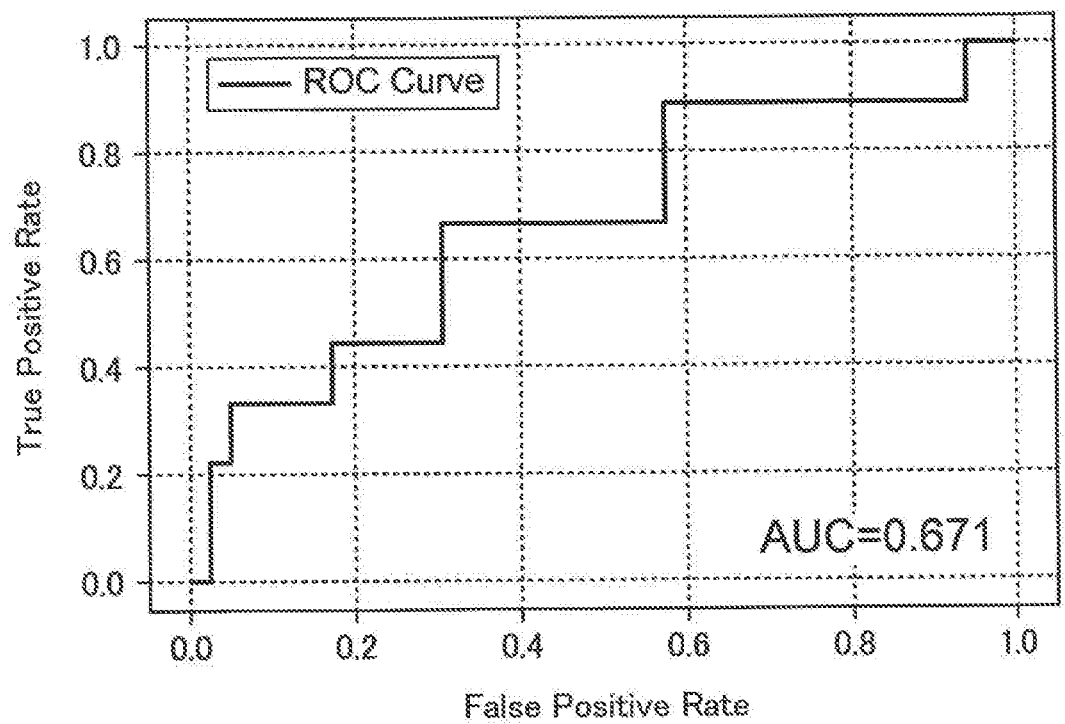
FIG. 23 is a view showing an ROC curve obtained as a result of determining a healthy subject and a mild cognitive impairment subject using a prediction model in an eighth modification of the present embodiment.

FIG. 23 is a view showing an ROC curve obtained as a result of determining a healthy subject and a mild cognitive impairment subject using a prediction model in the eighth modification of the present embodiment.

The prediction model in the eighth modification of the present embodiment was created with whether or not the subject has mild cognitive impairment as an objective variable, and with the mean value of the vertical displacements of the waist in the period of 21% to 30% of one walking cycle and the mean value of the angles of one knee joint in the period of 41% to 50% of one walking cycle as explanatory variables. In FIG. 23, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 23 was obtained by plotting the true positive rate and the false positive rate of the prediction model created with the mean value of the vertical displacements of the waist in the period of 21% to 30% of one walking cycle and the mean value of the angles of one knee joint in the period of 41% to 50% of one walking cycle as explanatory variables. The AUC value of the ROC curve shown in FIG. 23 was 0.671. In this case, the mean value of the vertical displacements of the waist in the period of 21% to 30% of one walking cycle and the mean value of the angles of one knee joint in the period of 41% to 50% of one walking cycle are determined as walking parameters. In addition, the prediction model created with the mean value of the vertical displacements of the waist in the period of 21% to 30% of one walking cycle and the mean value of the angles of one knee joint in the period of 41% to 50% of one walking cycle as the explanatory variables is determined as the prediction model used by the cognitive function determination unit 113.

The walking parameter detection unit 112 detects time series data of the vertical displacement of the waist in the first period of the stance phase of one leg and time series data of the angle of the knee joint in the second period of the stance phase of one leg. The first period is a period of 21% to 30% of one walking cycle, and the second period is a period of 41% to 50% of one walking cycle. The walking parameter detection unit 112 detects time series data of the vertical displacement of the waist in the period of 21% to 30% of one walking cycle and time series data of the angle of one knee joint in the period of 41% to 50% of one walking cycle. In addition, the walking parameter detection unit 112 calculates the mean value of time series data of the vertical displacement of the waist in the period of 21% to 30% of one walking cycle and the mean value of the time series data of the angle of one knee joint in the period of 41% to 50% of one walking cycle.

The cognitive function determination unit 113 determines the cognitive function level of the subject using the mean value of time series data of the vertical displacement of the waist and the mean value of the time series data of the angle of the knee joint.

The memory 12 stores in advance a prediction model generated with the mean value of time series data of the vertical displacement of the waist in the first period of the stance phase of one leg and the mean value of the time series data of the angle of the knee joint in the second period of the stance phase of one leg as input values, and with whether or not the subject has mild cognitive impairment as an output value. The memory 12 stores in advance a prediction model generated with the mean value of the vertical displacements of the waist in the period of 21% to 30% of one walking cycle and the mean value of the angles of one knee joint in the period of 41% to 50% of one walking cycle as input values, and with whether or not the subject has mild cognitive impairment as an output value.

The cognitive function determination unit 113 determines the cognitive function level of the subject using the mean value of time series data of the vertical displacement of the waist in the period of 21% to 30% of one walking cycle and the mean value of the time series data of the angle of one knee joint in the period of 41% to 50% of one walking cycle. By inputting the mean value of time series data of the vertical displacement of the waist in the period of 21% to 30% of one walking cycle and the mean value of the time series data of the angle of one knee joint in the period of 41% to 50% of one walking cycle into the prediction model, the cognitive function determination unit 113 acquires, from the prediction model, a determination result indicating whether or not the subject has mild cognitive impairment.

Thus, the AUC value of the prediction model created using the vertical displacement of the waist in isolation was 0.587, and the AUC value of the prediction model created using the angle of the knee joint and the vertical displacement of the waist was 0.671. Accordingly, it is possible to determine the cognitive function level more accurately in the prediction model created using the angle of the knee joint and the vertical displacement of the waist than in the prediction model created using the vertical displacement of the waist in isolation.

Subsequently, the walking parameters in the ninth modification of the present embodiment will be described.

The walking parameter in the ninth modification of the present embodiment may be a mean value of time series data of the vertical displacement of the waist in the first period of the stance phase of one leg, a mean value of the time series data of the angle of the knee joint in the second period of the stance phase of one leg, and a mean value of the time series data of the angle of the ankle joint in the third period of the swing phase of one leg.

In the ninth modification of the present embodiment, similar to the above experiment, time series data of the vertical displacement of the waist of each of the plurality of subjects, time series data of the angle of one knee joint of each of the plurality of subjects, and time series data of the angle of one ankle joint of each of the plurality of subjects were detected. In addition, a prediction model was created with whether or not the subject has mild cognitive impairment as an objective variable and with the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 24:
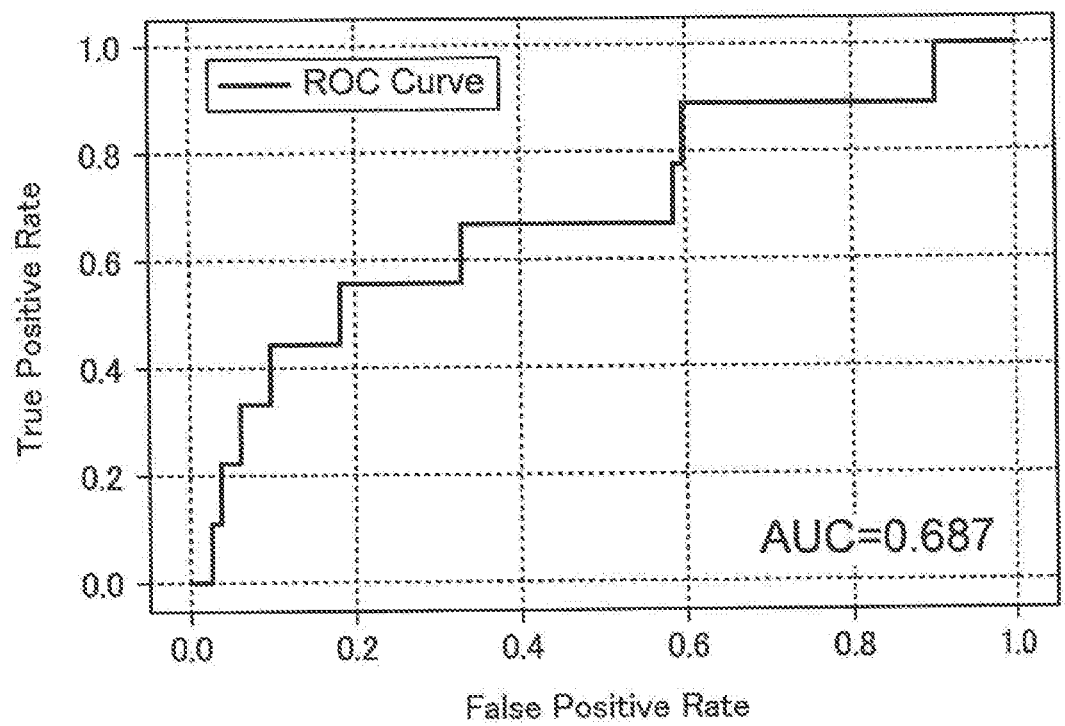
FIG. 24 is a view showing an ROC curve obtained as a result of determining a healthy subject and a mild cognitive impairment subject using a prediction model in a ninth modification of the present embodiment.

FIG. 24 is a view showing an ROC curve obtained as a result of determining a healthy subject and a mild cognitive impairment subject using a prediction model in the ninth modification of the present embodiment.

The prediction model in the ninth modification of the present embodiment was created with whether or not the subject has mild cognitive impairment as an objective variable, and with the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle as explanatory variables. In FIG. 24, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 24 was obtained by plotting the true positive rate and the false positive rate of the prediction model created with the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle as explanatory variables. The AUC value of the ROC curve shown in FIG. 24 was 0.687. In this case, the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle are determined as walking parameters. In addition, the prediction model created with the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle as the explanatory variables is determined as the prediction model used by the cognitive function determination unit 113.

The walking parameter detection unit 112 detects time series data of the vertical displacement of the waist in the first period of the stance phase of one leg, time series data of the angle of the knee joint in the second period of the stance phase of one leg, and time series data of the angle of the ankle joint in the third period of the swing phase of one leg. The first period is a period of 21% to 30% of one walking cycle, the second period is a period of 41% to 50% of one walking cycle, and the third period is a period of 81% to 100% of one walking cycle. The walking parameter detection unit 112 detects time series data of the vertical displacement of the waist in the period of 21% to 30% of one walking cycle, time series data of the angle of one knee joint in the period of 41% to 50% of one walking cycle, and time series data of the angle of one ankle joint in the period of 81% to 100% of one walking cycle.

In addition, the walking parameter detection unit 112 calculates the mean value of time series data of the vertical displacement of the waist in the period of 21% to 30% of one walking cycle, the mean value of the time series data of the angle of one knee joint in the period of 41% to 50% of one walking cycle, and the mean value of the time series data of the angle of one ankle joint in the period of 81% to 100% of one walking cycle.

The cognitive function determination unit 113 determines the cognitive function level of the subject using the mean value of time series data of the vertical displacement of the waist, the mean value of the time series data of the angle of the knee joint, and the mean value of the time series data of the angle of the ankle joint.

The memory 12 stores in advance a prediction model generated with the mean value of time series data of the vertical displacement of the waist in the first period of the stance phase of one leg, the mean value of the time series data of the angle of the knee joint in the second period of the stance phase of one leg, and the mean value of the time series data of the angle of the ankle joint in the third period of the swing phase of one leg as input values, and with whether or not the subject has mild cognitive impairment as an output value. The memory 12 stores in advance a prediction model generated with the mean value of the vertical displacements of the waist in the period of 21% to 30% of one walking cycle, the mean value of the angles of one knee joint in the period of 41% to 50% of one walking cycle, and the mean value of the angles of one ankle joint in the period of 81% to 100% of one walking cycle as input values, and with whether or not the subject has mild cognitive impairment as an output value.

The cognitive function determination unit 113 determines the cognitive function level of the subject using the mean value of time series data of the vertical displacement of the waist in the period of 21% to 30% of one walking cycle, the mean value of the time series data of the angle of one knee joint in the period of 41% to 50% of one walking cycle, and the mean value of the time series data of the angle of one ankle joint in the period of 81% to 100% of one walking cycle. By inputting the mean value of time series data of the vertical displacement of the waist in the period of 21% to 30% of one walking cycle, the mean value of the time series data of the angle of one knee joint in the period of 41% to 50% of one walking cycle, and the mean value of the time series data of the angle of one ankle joint in the period of 81% to 100% of one walking cycle into the prediction model, the cognitive function determination unit 113 acquires, from the prediction model, a determination result indicating whether or not the subject has mild cognitive impairment.

Thus, the AUC value of the prediction model created using the angle of the ankle joint, the angle of the knee joint, and the vertical displacement of the waist in isolation were 0.660, 0.682, and 0.587, respectively, and the AUC value of the prediction model created using the angle of the ankle joint, the angle of the knee joint, and the vertical displacement of the waist was 0.687. Accordingly, it is possible to determine the cognitive function level more accurately in the prediction model created using the angle of the ankle joint, the angle of the knee joint, and the vertical displacement of the waist than in the prediction model created using each of the angle of the ankle joint, the angle of the knee joint, and the vertical displacement of the waist in isolation.

Subsequently, the walking parameters in the tenth modification of the present embodiment will be described.

In the tenth modification of the present embodiment, in the case where the subject is male, the walking parameter may be a mean value of the time series data of the angle of the ankle joint in the early stance phase of one leg.

Figure 25:
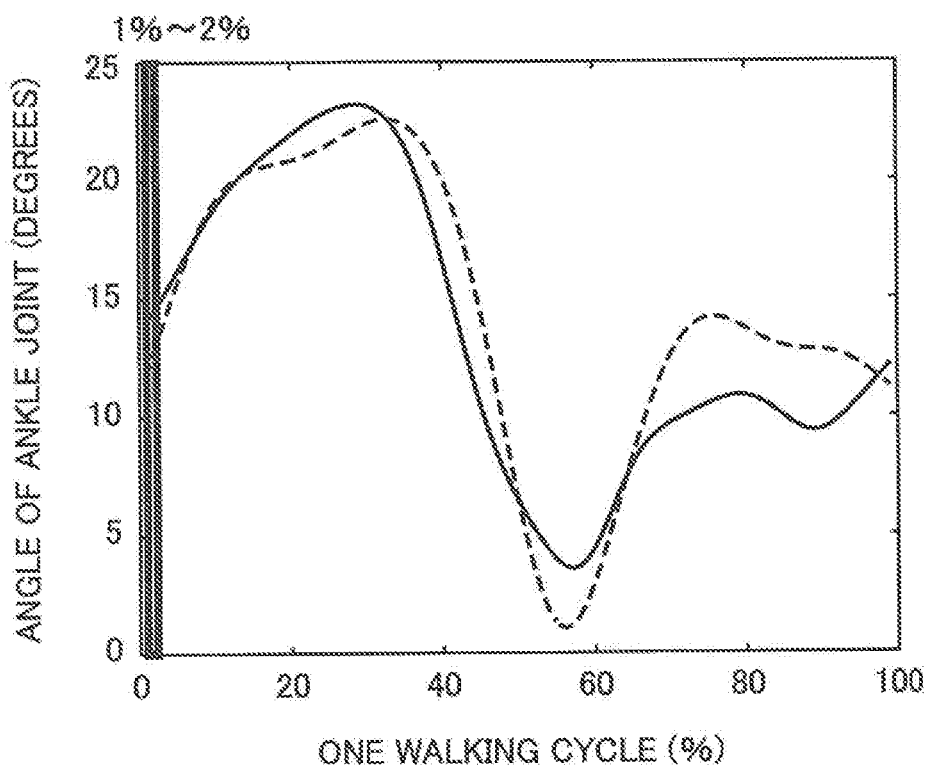
FIG. 25 is a view showing a change in the angle of one ankle joint of a male subject in one walking cycle in a tenth modification of the present embodiment.

FIG. 25 is a view showing a change in the angle of one ankle joint of a male subject in one walking cycle in the tenth modification of the present embodiment. In FIG. 25, the vertical axis represents the angle of the ankle joint, and the horizontal axis represents one normalized walking cycle. In addition, in FIG. 25, the dashed line represents an average waveform of the angles of one ankle joint of the male healthy subjects, and the solid line represents an average waveform of the angles of one ankle joint of the male mild cognitive impairment patients.

In the tenth modification of the present embodiment, unlike the above experiment, time series data of the angle of one ankle joint of each of the male subjects was detected. The average waveform of the angles of one ankle joint of the male subjects indicates that the angle of the ankle joint of the mild cognitive impairment patients is larger than the angle of the ankle joint of the healthy subjects in the period of 1% to 2% of one walking cycle, which is the early stance phase. Therefore, a prediction model was created with whether or not the subject has mild cognitive impairment as an objective variable and with the mean value of the angles of one ankle joint in the period of 1% to 2% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 26:
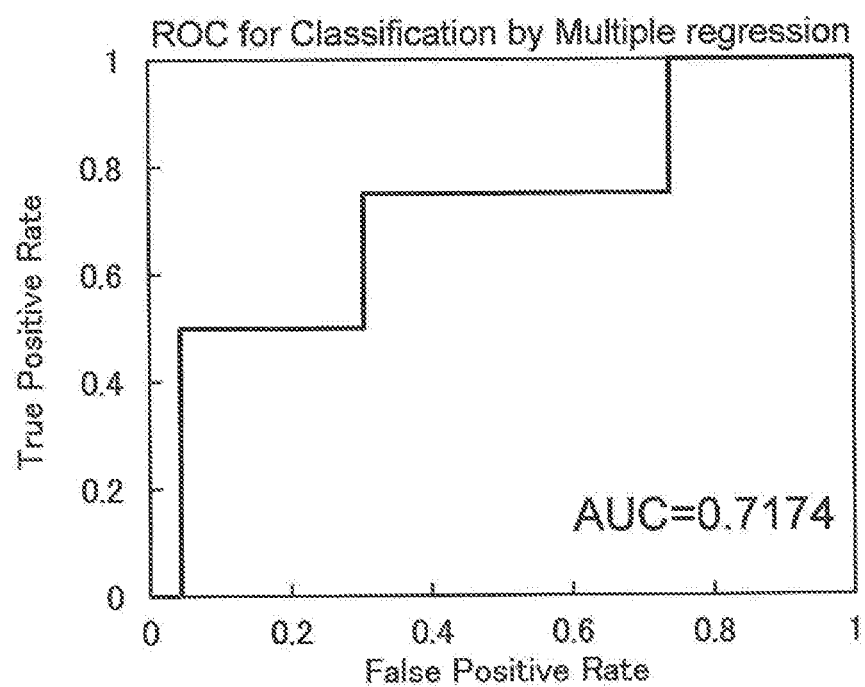
FIG. 26 is a view showing an ROC curve obtained as a result of determining a healthy subject and a mild cognitive impairment subject using a prediction model in the tenth modification of the present embodiment.

FIG. 26 is a view showing an ROC curve obtained as a result of determining a healthy subject and a mild cognitive impairment subject using a prediction model in the tenth modification of the present embodiment.

The prediction model in the tenth modification of the present embodiment was created with whether or not the subject has mild cognitive impairment as an objective variable, and with the mean value of the angles of one ankle joint of the male subject in the period of 1% to 2% of one walking cycle as an explanatory variable. In FIG. 26, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 26 was obtained by plotting the true positive rate and the false positive rate of the prediction model created with the mean value of the angles of one ankle joint of the male subject in the period of 1% to 2% of one walking cycle as an explanatory variable. The AUC value of the ROC curve shown in FIG. 26 was 0.7174. When the subject is a male, the mean value of the angles of the ankle joint in the period of 1% to 2% of one walking cycle is determined as a walking parameter. In addition, the prediction model created with the mean value of the angles of one ankle joint of the male subject in the period of 1% to 2% of one walking cycle as the explanatory variable is determined as the prediction model used by the cognitive function determination unit 113.

The processor 11 of the cognitive function evaluation device 1 in the tenth modification of the present embodiment further includes a sex recognition unit that recognizes the sex of the subject. The sex recognition unit detects the feature amount of at least one of the face and the body from an image of the subject included in moving image data. Then, the sex recognition unit recognizes whether the subject is male or female from the detected feature amount. It is to be noted that the memory 12 may store in advance user information in which the face image and the sex of the subject are associated with each other. In this case, the sex recognition unit may recognize whether the subject included in the moving image data is male or female by using the user information stored in the memory 12.

The memory 12 stores in advance a prediction model generated with the mean value of the time series data of the angle of the ankle joint of one foot of the male subject in the period of 1% to 2% of one walking cycle as an input value, and with whether or not the subject has mild cognitive impairment as an output value.

When the sex recognition unit recognizes that the subject is male, the walking parameter detection unit 112 detects time series data of the angle of the ankle joint in the early stance phase of one leg. When the sex recognition unit recognizes that the subject is male, the walking parameter detection unit 112 detects time series data of the angle of the ankle joint of one foot in the period of 1% to 2% of one walking cycle. In addition, the walking parameter detection unit 112 calculates the mean value of the time series data of the angle of one ankle joint in the period of 1% to 2% of one walking cycle.

The cognitive function determination unit 113 determines the cognitive function level of the male subject by using the mean value of the time series data of the angle of the ankle joint of one foot in the period of 1% to 2% of one walking cycle. By inputting the mean value of the time series data of the angle of the ankle joint of one foot in the period of 1% to 2% of one walking cycle into the prediction model, the cognitive function determination unit 113 acquires, from the prediction model, a determination result indicating whether or not the male subject has mild cognitive impairment.

In addition, in the case where the subject is male, in the early stance phase (period of 1% to 2% of one walking cycle), the average waveform of the angles of the ankle joint of one foot of the mild cognitive impairment patients is higher than the average waveform of the angles of the ankle joint of one foot of the healthy subjects. Therefore, a value between the average of the mean values of time series data of the angle of the ankle joint of one foot in the period of 1% to 2% of one walking cycle of the male mild cognitive impairment patients and the mean values of time series data of the angle of the ankle joint of one foot in the period of 1% to 2% of one walking cycle of the male healthy subjects, having been experimentally obtained, may be stored in the memory 12 as the threshold value. The cognitive function determination unit 113 may determine the cognitive function level by comparing the mean value of the time series data of the angle of the ankle joint of one foot of the subject in the period of 1% to 2% of one walking cycle with the threshold value stored in advance.

Thus, in the case where the subject is male, it is possible to determine the cognitive function level with higher accuracy by using time series data of the angle of the ankle joint of one foot of the early stance phase (period of 1% to 2% of one walking cycle).

Subsequently, the walking parameters in the eleventh modification of the present embodiment will be described.

In the eleventh modification of the present embodiment, in the case where the subject is male, the walking parameter may be a mean value of the time series data of the first angle of the ankle joint in the first period of the stance phase of one leg and a mean value of the time series data of the second angle of the ankle joint in the second period of the swing phase of one leg.

Figure 27:
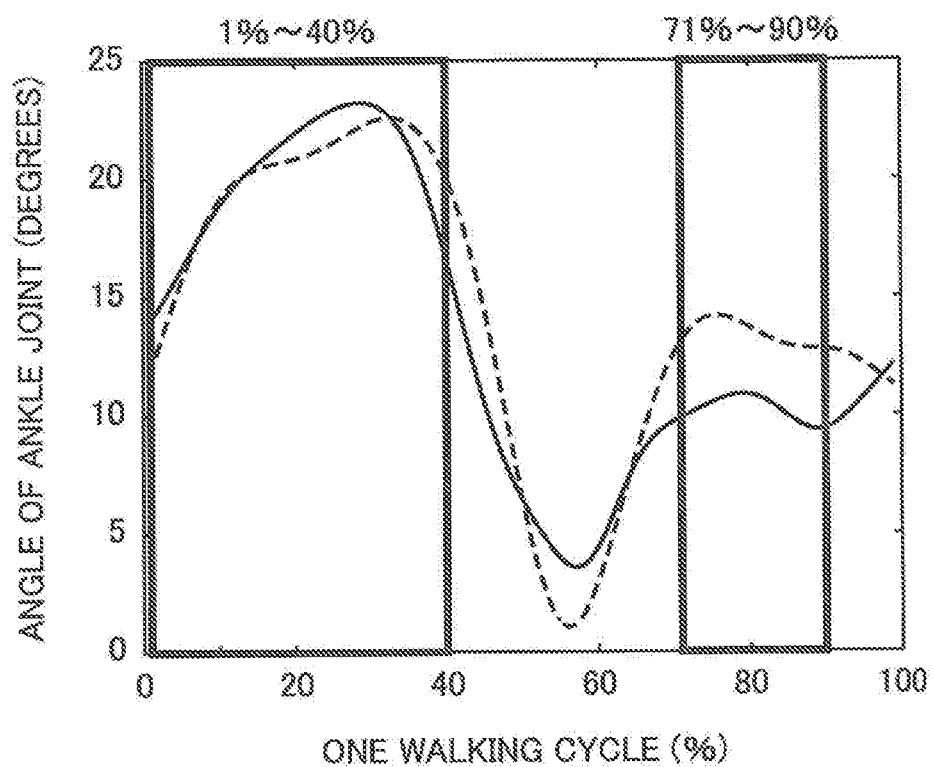
FIG. 27 is a view showing a change in the angle of one ankle joint of a male subject in one walking cycle in an eleventh modification of the present embodiment.

FIG. 27 is a view showing a change in the angle of one ankle joint of a male subject in one walking cycle in the eleventh modification of the present embodiment. In FIG. 27, the vertical axis represents the angle of the ankle joint, and the horizontal axis represents one normalized walking cycle. In addition, in FIG. 27, the dashed line represents an average waveform of the angles of one ankle joint of the male healthy subjects, and the solid line represents an average waveform of the angles of one ankle joint of the male mild cognitive impairment patients.

In the eleventh modification of the present embodiment, unlike the above experiment, time series data of the angle of one ankle joint of each of the male subjects was detected. In addition, a prediction model was created with whether or not the subject has mild cognitive impairment as an objective variable and with the mean value of the angles of one ankle joint in the period of 1% to 40% of one walking cycle and the mean value of the angles of one ankle joint in the period of 71% to 90% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 28:
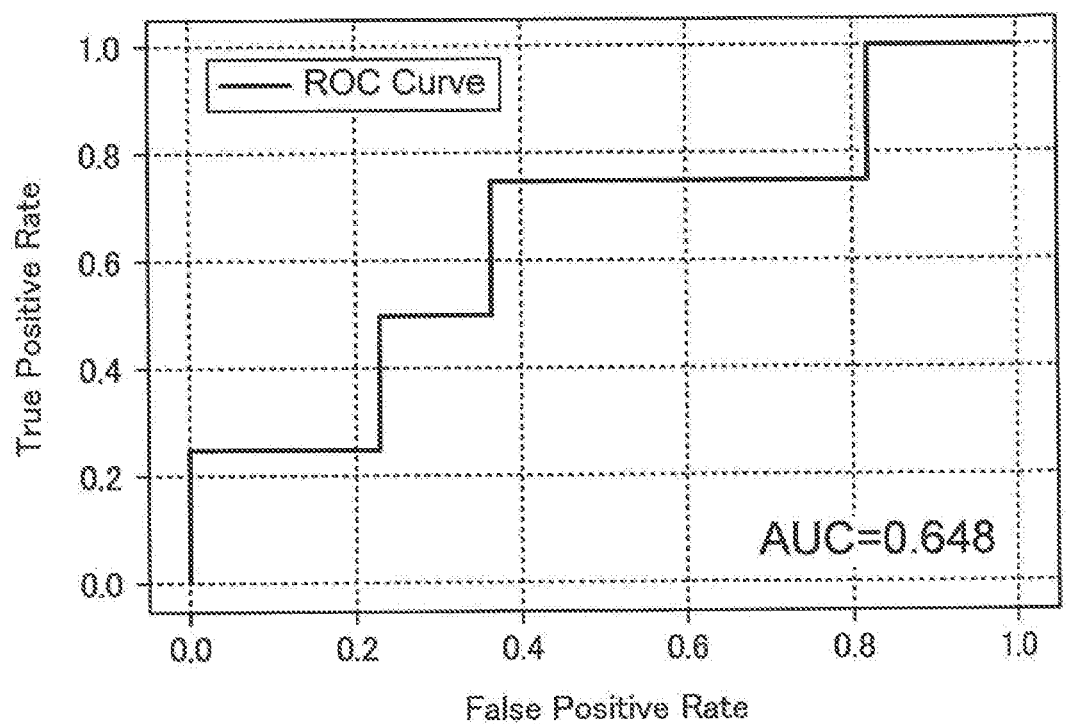
FIG. 28 is a view showing an ROC curve obtained as a result of determining a healthy subject and a mild cognitive impairment subject using a prediction model in the eleventh modification of the present embodiment.

FIG. 28 is a view showing an ROC curve obtained as a result of determining a healthy subject and a mild cognitive impairment subject using a prediction model in the eleventh modification of the present embodiment.

The prediction model in the eleventh modification of the present embodiment was created with whether or not the subject has mild cognitive impairment as an objective variable, and with the mean value of the angles of one ankle joint of the male subject in the period of 1% to 40% of one walking cycle and the mean value of the angles of one ankle joint of the male subject in the period of 71% to 90% of one walking cycle as explanatory variables. In FIG. 28, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 28 was obtained by plotting the true positive rate and the false positive rate of the prediction model created with the mean value of the angles of one ankle joint of the male subject in the period of 1% to 40% of one walking cycle and the mean value of the angles of one ankle joint of the male subject in the period of 71% to 90% of one walking cycle as explanatory variables. The AUC value of the ROC curve shown in FIG. 28 was 0.648. In the case where the subject is male, the mean value of the angles of the ankle joint in the period of 1% to 40% of one walking cycle and the mean value of the angles of the ankle joint in the period of 71% to 90% of one walking cycle are determined as walking parameters. In addition, the prediction model created with the mean value of the angles of one ankle joint of the male subject in the period of 1% to 40% of one walking cycle and the mean value of the angles of one ankle joint of the male subject in the period of 71% to 90% of one walking cycle as the explanatory variables is determined as the prediction model used by the cognitive function determination unit 113.

The processor 11 of the cognitive function evaluation device 1 in the eleventh modification of the present embodiment further includes the sex recognition unit that recognizes the sex of the subject.

When the sex recognition unit recognizes that the subject is male, the walking parameter detection unit 112 detects time series data of the first angle of the ankle joint in the first period of the stance phase of one leg and time series data of the second angle of the ankle joint in the second period of the swing phase of one leg. The first period is a period of 1% to 40% of one walking cycle, and the second period is a period of 71% to 90% of one walking cycle. When the sex recognition unit recognizes that the subject is male, the walking parameter detection unit 112 detects time series data of the angle of one ankle joint in the period of 1% to 40% of one walking cycle and time series data of the angle of one ankle joint in the period of 71% to 90% of one walking cycle. In addition, the walking parameter detection unit 112 calculates the mean value of the time series data of the angle of one ankle joint in the period of 1% to 40% of one walking cycle and the mean value of the time series data of the angle of one ankle joint in the period of 71% to 90% of one walking cycle.

The cognitive function determination unit 113 determines the cognitive function level of the male subject by using the mean value of the time series data of the first angle of the ankle joint and the mean value of the time series data of the second angle.

The memory 12 stores in advance a prediction model generated with the mean value of the time series data of the first angle of the ankle joint of the male subject in the first period of the stance phase of one leg and the mean value of the time series data of the second angle of the ankle joint of the male subject in the second period of the swing phase of one leg as input values, and with whether or not the subject has mild cognitive impairment as an output value. The memory 12 stores in advance a prediction model generated with the mean value of the angles of one ankle joint of the male subject in the period of 1% to 40% of one walking cycle and the mean value of the angles of one ankle joint of the male subject in the period of 71% to 90% of one walking cycle as input values, and with whether or not the subject has mild cognitive impairment as an output value.

The cognitive function determination unit 113 determines the cognitive function level of the male subject by using the mean value of the time series data of the angle of one ankle joint in the period of 1% to 40% of one walking cycle and the mean value of the time series data of the angle of one ankle joint in the period of 71% to 90% of one walking cycle. By inputting the mean value of the time series data of the angle of one ankle joint in the period of 1% to 40% of one walking cycle and the mean value of the time series data of the angle of one ankle joint in the period of 71% to 90% of one walking cycle into the prediction model, the cognitive function determination unit 113 acquires, from the prediction model, a determination result indicating whether or not the male subject has mild cognitive impairment.

Thus, in the case where the subject is male, it is possible to determine the cognitive function level with higher accuracy by using time series data of the angle of the ankle joint of one foot of the stance phase (period of 1% to 40% of one walking cycle) and the swing phase (period of 71% to 90% of one walking cycle).

Subsequently, the walking parameters in the twelfth modification of the present embodiment will be described.

In the twelfth modification of the present embodiment, in the case where the subject is male, the walking parameter may be a mean value of the time series data of the angle of the knee joint in the swing phase of one leg.

Figure 29:
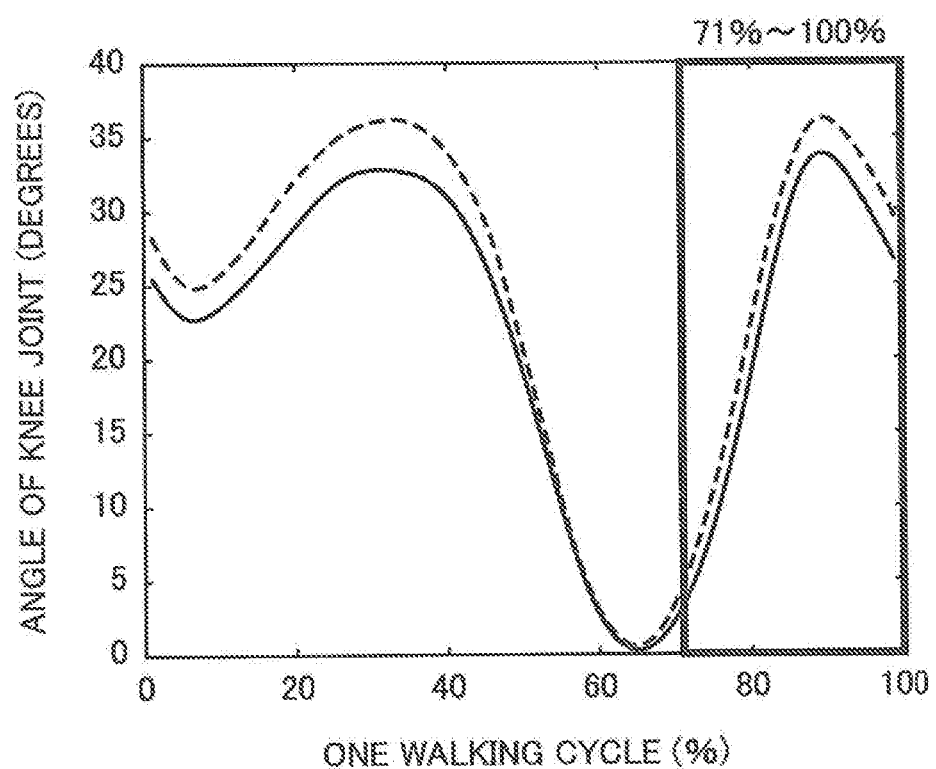
FIG. 29 is a view showing a change in the angle of one knee joint of a male subject in one walking cycle in a twelfth modification of the present embodiment.

FIG. 29 is a view showing a change in the angle of one knee joint of a male subject in one walking cycle in the twelfth modification of the present embodiment. In FIG. 29, the vertical axis represents the angle of the knee joint, and the horizontal axis represents one normalized walking cycle. In addition, in FIG. 29, the dashed line represents an average waveform of the angles of one knee joint of the male healthy subjects, and the solid line represents an average waveform of the angles of one knee joint of the male mild cognitive impairment patients.

In the twelfth modification of the present embodiment, unlike the above experiment, time series data of the angle of one knee joint of each of the male subjects was detected. In addition, a prediction model was created with whether or not the subject has mild cognitive impairment as an objective variable, and with the mean value of the angles of one knee joint in the period of 71% to 100% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 30:
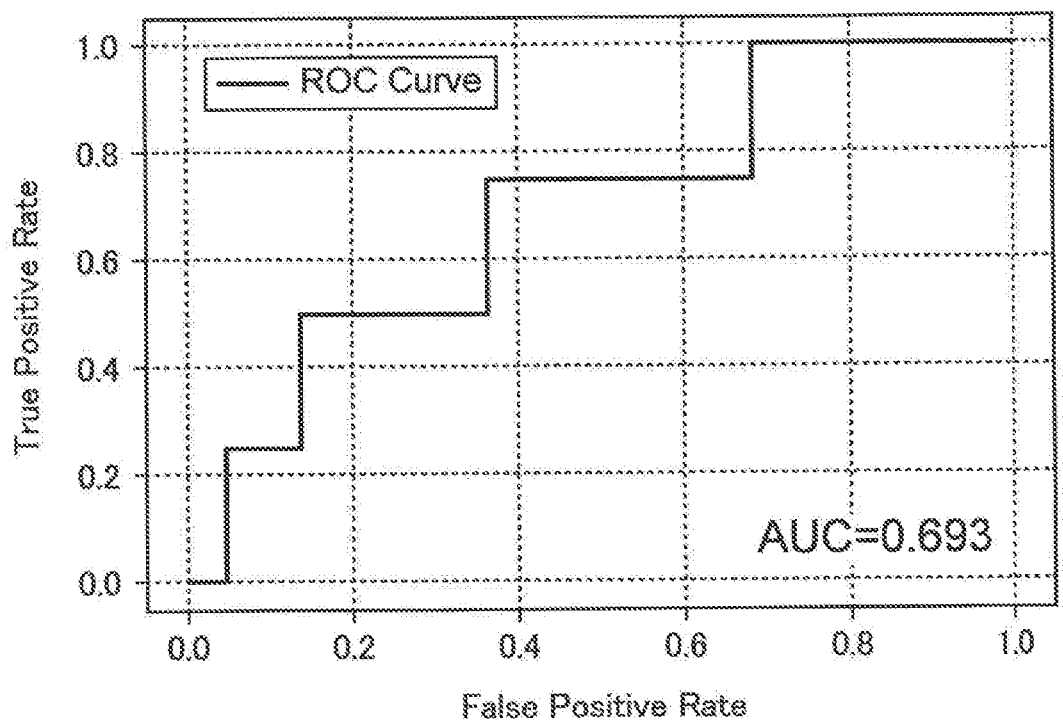
FIG. 30 is a view showing an ROC curve obtained as a result of determining a healthy subject and a mild cognitive impairment subject using a prediction model in the twelfth modification of the present embodiment.

FIG. 30 is a view showing an ROC curve obtained as a result of determining a healthy subject and a mild cognitive impairment subject using a prediction model in the twelfth modification of the present embodiment.

The prediction model in the twelfth modification of the present embodiment was created with whether or not the subject has mild cognitive impairment as an objective variable, and with the mean value of the angles of one knee joint of the male subject in the period of 71% to 100% of one walking cycle as an explanatory variable. In FIG. 30, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 30 was obtained by plotting the true positive rate and the false positive rate of the prediction model created with the mean value of the angles of one knee joint of the male subject in the period of 71% to 100% of one walking cycle as an explanatory variable. The AUC value of the ROC curve shown in FIG. 30 was 0.693. the subject is a male, the mean value of the angles of the knee joint in the period of 71% to 100% of one walking cycle is determined as a walking parameter. In addition, the prediction model created with the mean value of the angles of one knee joint of the male subject in the period of 71% to 100% of one walking cycle as the explanatory variable is determined as the prediction model used by the cognitive function determination unit 113.

The processor 11 of the cognitive function evaluation device 1 in the twelfth modification of the present embodiment further includes the sex recognition unit that recognizes the sex of the subject.

The memory 12 stores in advance a prediction model generated with the mean value of the time series data of the angle of the knee joint of one leg of the male subject in the period of 71% to 100% of one walking cycle as an input value, and with whether or not the subject has mild cognitive impairment as an output value.

When the sex recognition unit recognizes that the subject is male, the walking parameter detection unit 112 detects time series data of the angle of the knee joint in the swing phase of one leg. When the sex recognition unit recognizes that the subject is male, the walking parameter detection unit 112 detects time series data of the angle of the knee joint of one leg in the period of 71% to 100% of one walking cycle. In addition, the walking parameter detection unit 112 calculates the mean value of the time series data of the angle of the knee joint of one leg in the period of 71% to 100% of one walking cycle.

The cognitive function determination unit 113 determines the cognitive function level of the subject by using the mean value of the time series data of the angle of the knee joint. The cognitive function determination unit 113 determines the cognitive function level of the male subject by using the mean value of the time series data of the angle of the knee joint of one leg in the period of 71% to 100% of one walking cycle. By inputting the mean value of the time series data of the angle of the knee joint of one leg in the period of 71% to 100% of one walking cycle into the prediction model, the cognitive function determination unit 113 acquires, from the prediction model, a determination result indicating whether or not the male subject has mild cognitive impairment.

In addition, in the case where the subject is male, in the swing phase (period of 71% to 100% of one walking cycle), the average waveform of the angles of the knee joint of one leg of the mild cognitive impairment patients is smaller than the average waveform of the angles of the knee joint of one leg of the healthy subjects. Therefore, a value between the average of the mean values of time series data of the angle of the knee joint of one leg in the period of 71% to 100% of one walking cycle of the male mild cognitive impairment patients and the average of the mean values of time series data of the angle of the knee joint of one leg in the period of 71% to 100% of one walking cycle of the male healthy subjects, having been experimentally obtained, may be stored in the memory 12 as the threshold value. The cognitive function determination unit 113 may determine the cognitive function level by comparing the mean value of the time series data of the angle of the knee joint of one leg of the subject in the period of 71% to 100% of one walking cycle with the threshold value stored in advance.

Thus, in the case where the subject is male, it is possible to determine the cognitive function level with higher accuracy by using time series data of the angle of the knee joint of one leg of the swing phase (period of 71% to 100% of one walking cycle).

Subsequently, the walking parameters in the thirteenth modification of the present embodiment will be described.

In the thirteenth modification of the present embodiment, in the case where the subject is male, the walking parameter may be a mean value of the time series data of the first vertical displacement of the waist in the first period of one walking cycle, a mean value of the time series data of the second vertical displacement of the waist in the second period of one walking cycle, and a mean value of the time series data of the third vertical displacement of the waist in the third period of one walking cycle.

Figure 31:
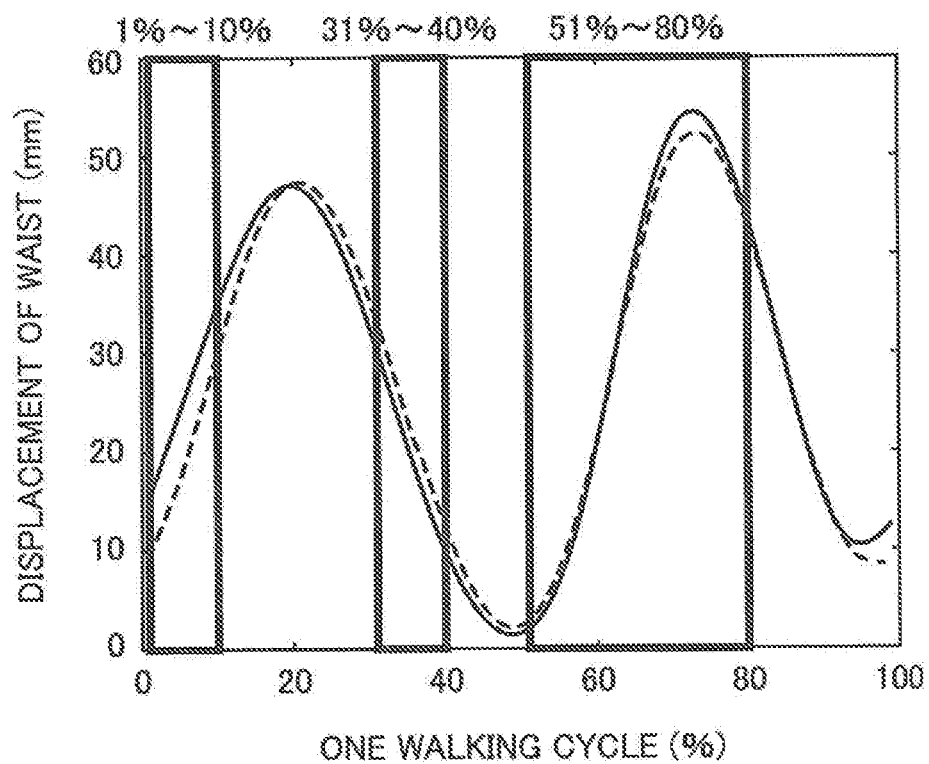
FIG. 31 is a view showing a vertical displacement of a waist of a male subject in one walking cycle in a thirteenth modification of the present embodiment.

FIG. 31 is a view showing a vertical displacement of a waist of a male subject in one walking cycle in the thirteenth modification of the present embodiment. In FIG. 31, the vertical axis represents the vertical displacement of the waist, and the horizontal axis represents one normalized walking cycle. In addition, in FIG. 31, the dashed line represents an average waveform of the vertical displacement of the waist of the male healthy subjects, and the solid line represents an average waveform of the vertical displacement of the waist of the male mild cognitive impairment patients.

In the thirteenth modification of the present embodiment, unlike the above experiment, time series data of the vertical displacement of the waist of each of the male subjects was detected. In addition, a prediction model was created with whether or not the subject has mild cognitive impairment as an objective variable and with the mean value of the first vertical displacements of the waist in the first period of 1% to 10% of one walking cycle, the mean value of the second vertical displacements of the waist in the second period of 31% to 40% of one walking cycle, and the mean value of the third vertical displacements of the waist in the third period of 51% to 80% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 32:
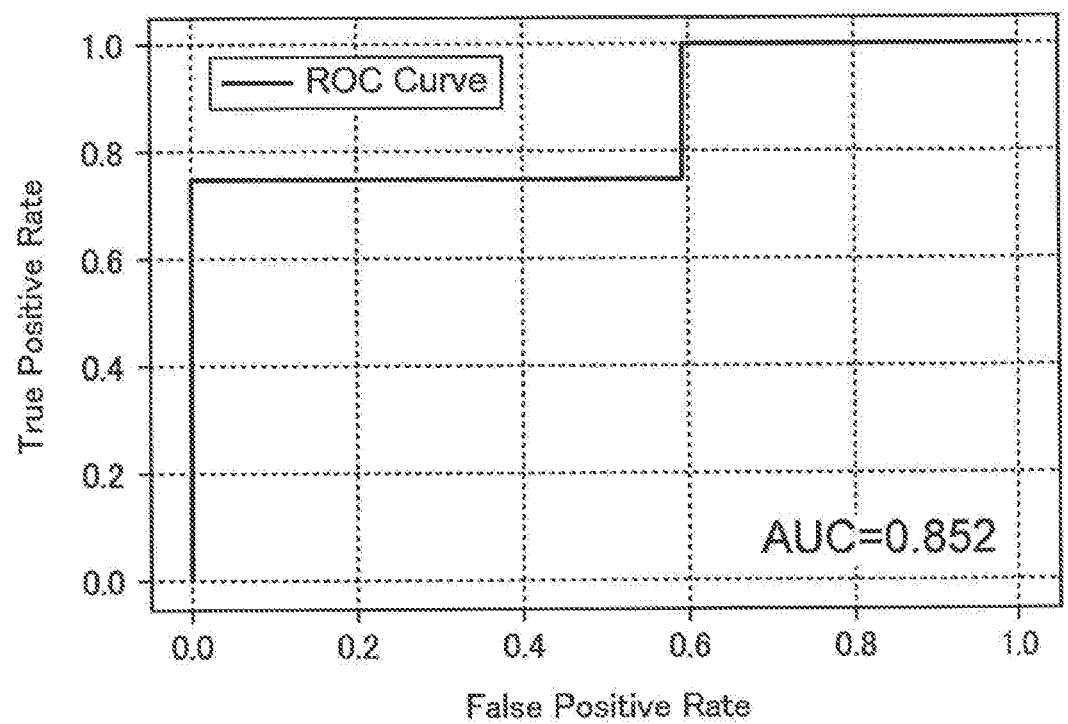
FIG. 32 is a view showing an ROC curve obtained as a result of determining a healthy subject and a mild cognitive impairment subject using a prediction model in the thirteenth modification of the present embodiment.

FIG. 32 is a view showing an ROC curve obtained as a result of determining a healthy subject and a mild cognitive impairment subject using a prediction model in the thirteenth modification of the present embodiment.

The prediction model in the thirteenth modification of the present embodiment was created with whether or not the subject has mild cognitive impairment as an objective variable, and with the mean value of the first vertical displacements of the waist of the male subject in the first period of 1% to 10% of one walking cycle, the mean value of the second vertical displacements of the waist of the male subject in the second period of 31% to 40% of one walking cycle, and the mean value of the third vertical displacements of the waist of the male subject in the third period of 51% to 80% of one walking cycle as explanatory variables. In FIG. 32, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 32 was obtained by plotting the true positive rate and the false positive rate of the prediction model created with the mean value of the first vertical displacements of the waist of the male subject in the first period of 1% to 10% of one walking cycle, the mean value of the second vertical displacements of the waist of the male subject in the second period of 31% to 40% of one walking cycle, and the mean value of the third vertical displacements of the waist of the male subject in the third period of 51% to 80% of one walking cycle as explanatory variables. The AUC value of the ROC curve shown in FIG. 32 was 0.852. In the case where the subject is male, the mean value of the first vertical displacements of the waist in the first period of 1% to 10% of one walking cycle, the mean value of the second vertical displacements of the waist in the second period of 31% to 40% of one walking cycle, and the mean value of the third vertical displacements of the waist in the third period of 51% to 80% of one walking cycle are determined as walking parameters. In addition, the prediction model created with the mean value of the first vertical displacements of the waist of the male subject in the first period of 1% to 10% of one walking cycle, the mean value of the second vertical displacements of the waist of the male subject in the second period of 31% to 40% of one walking cycle, and the mean value of the third vertical displacements of the waist of the male subject in the third period of 51% to 80% of one walking cycle as explanatory variables is determined as the prediction model used by the cognitive function determination unit 113.

The processor 11 of the cognitive function evaluation device 1 in the thirteenth modification of the present embodiment further includes the sex recognition unit that recognizes the sex of the subject.

When the sex recognition unit recognizes that the subject is male, the walking parameter detection unit 112 detects time series data of the first vertical displacement of the waist in the first period of one walking cycle, time series data of the second vertical displacement of the waist in the second period of one walking cycle, and time series data of the third vertical displacement of the waist in the third period of one walking cycle. The first period is a period of 1% to 10% of one walking cycle, the second period is a period of 31% to 40% of one walking cycle, and the third period is a period of 51% to 80% of one walking cycle. When the sex recognition unit recognizes that the subject is male, the walking parameter detection unit 112 detects time series data of the first vertical displacement of the waist in the first period of 1% to 10% of one walking cycle, time series data of the second vertical displacement of the waist in the second period of 31% to 40% of one walking cycle, and time series data of the third vertical displacement of the waist in the third period of 51% to 80% of one walking cycle.

The third period may be divided into a period of 51% to 60% of one walking cycle and a period of 61% to 80% of one walking cycle. The period of 51% to 60% of one walking cycle belongs to the stance phase, and the period of 61% to 80% of one walking cycle belongs to the swing phase.

In addition, the walking parameter detection unit 112 calculates the mean value of the time series data of the first vertical displacement of the waist in the first period of 1% to 10% of one walking cycle, the mean value of the time series data of the second vertical displacement of the waist in the second period of 31% to 40% of one walking cycle, and the mean value of the time series data of the third vertical displacement of the waist in the third period of 51% to 80% of one walking cycle.

The cognitive function determination unit 113 determines the cognitive function level of the male subject by using the mean value of the time series data of the first vertical displacement of the waist, the mean value of the time series data of the second vertical displacement of the waist, and the mean value of the time series data of the third vertical displacement of the waist.

The memory 12 stores in advance a prediction model generated with the mean value of the time series data of the first vertical displacement of the waist of the male subject in the first period of one walking cycle, the mean value of the time series data of the second vertical displacement of the waist of the male subject in the second period of one walking cycle, and the mean value of the time series data of the third vertical displacement of the waist of the male subject in the third period of one walking cycle as input values, and with whether or not the subject has mild cognitive impairment as an output value. The memory 12 stores in advance a prediction model generated with the mean value of the first vertical displacements of the waist of the male subject in the first period of 1% to 10% of one walking cycle, the mean value of the second vertical displacements of the waist of the male subject in the second period of 31% to 40% of one walking cycle, and the mean value of the third vertical displacements of the waist of the male subject in the third period of 51% to 80% of one walking cycle as input values, and with whether or not the subject has mild cognitive impairment as an output value.

The cognitive function determination unit 113 determines the cognitive function level of the male subject by using the mean value of the time series data of the first vertical displacement of the waist in the first period of 1% to 10% of one walking cycle, the mean value of the time series data of the second vertical displacement of the waist in the second period of 31% to 40% of one walking cycle, and the mean value of the time series data of the third vertical displacement of the waist in the third period of 51% to 80% of one walking cycle. By inputting the mean value of the time series data of the first vertical displacement of the waist in the first period of 1% to 10% of one walking cycle, the mean value of the time series data of the second vertical displacement of the waist in the second period of 31% to 40% of one walking cycle, and the mean value of the time series data of the third vertical displacement of the waist in the third period of 51% to 80% of one walking cycle into the prediction model, the cognitive function determination unit 113 acquires, from the prediction model, a determination result indicating whether or not the male subject has mild cognitive impairment.

Thus, in the case where the subject is male, it is possible to determine the cognitive function level with higher accuracy by using time series data of the vertical displacement of the waist of the first period of one walking cycle (period of 1% to 10% of one walking cycle), the second period of one walking cycle (period of 31% to 40% of one walking cycle), and the third period of one walking cycle (period of 51% to 80% of one walking cycle).

Subsequently, the walking parameters in the fourteenth modification of the present embodiment will be described.

In the fourteenth modification of the present embodiment, in the case where the subject is female, the walking parameter may be a mean value of the time series data of the angle of the ankle joint in the swing phase of one leg.

Figure 33:
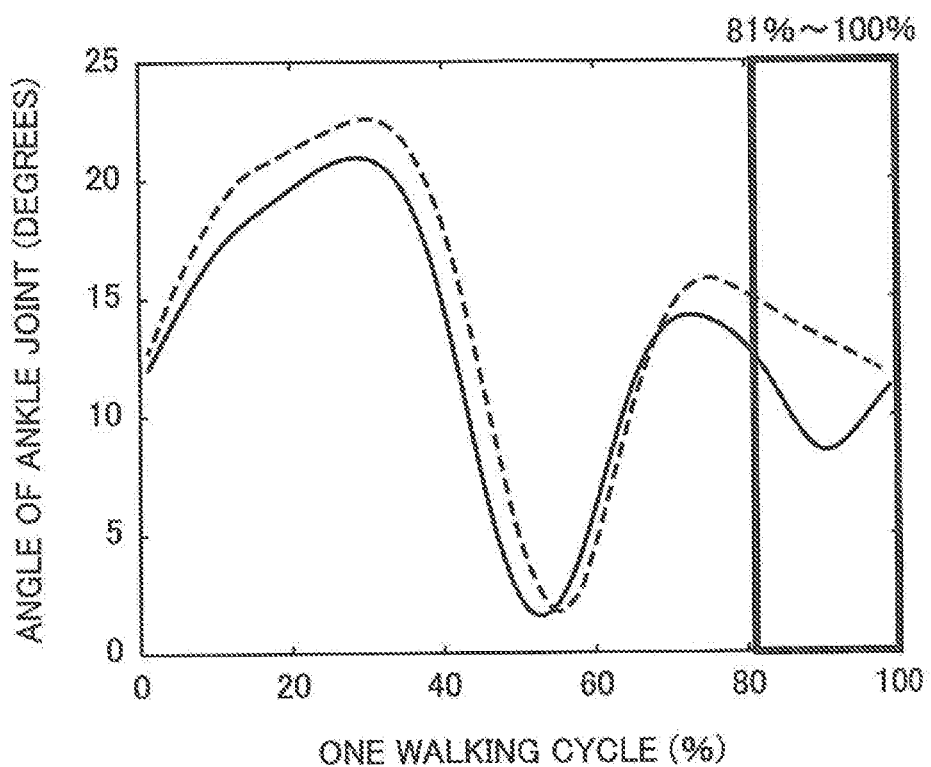
FIG. 33 is a view showing a change in the angle of one ankle joint of a female subject in one walking cycle in a fourteenth modification of the present embodiment.

FIG. 33 is a view showing a change in the angle of one ankle joint of a female subject in one walking cycle in the fourteenth modification of the present embodiment. In FIG. 33, the vertical axis represents the angle of the ankle joint, and the horizontal axis represents one normalized walking cycle. In addition, in FIG. 33, the dashed line represents an average waveform of the angles of one ankle joint of the female healthy subjects, and the solid line represents an average waveform of the angles of one ankle joint of the female mild cognitive impairment patients.

In the fourteenth modification of the present embodiment, unlike the above experiment, time series data of the angle of one ankle joint of each of the female subjects was detected. In addition, a prediction model was created with whether or not the subject has mild cognitive impairment as an objective variable, and with the mean value of the angles of one ankle joint in the period of 81% to 100% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 34:
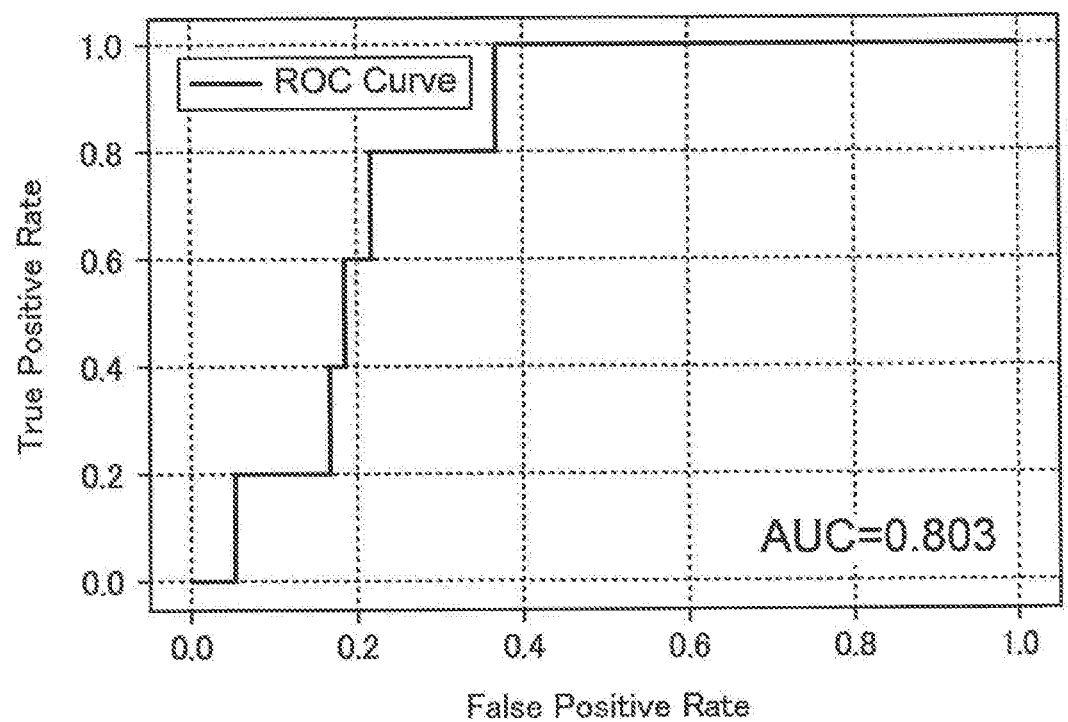
FIG. 34 is a view showing an ROC curve obtained as a result of determining a healthy subject and a mild cognitive impairment subject using a prediction model in the fourteenth modification of the present embodiment.

FIG. 34 is a view showing an ROC curve obtained as a result of determining a healthy subject and a mild cognitive impairment subject using a prediction model in the fourteenth modification of the present embodiment.

The prediction model in the fourteenth modification of the present embodiment was created with whether or not the subject has mild cognitive impairment as an objective variable, and with the mean value of the angles of one ankle joint of the female subject in the period of 81% to 100% of one walking cycle as an explanatory variable. In FIG. 34, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 34 was obtained by plotting the true positive rate and the false positive rate of the prediction model created with the mean value of the angles of one ankle joint of the female subject in the period of 81% to 100% of one walking cycle as an explanatory variable. The AUC value of the ROC curve shown in FIG. 34 was 0.803. When the subject is a female, the mean value of the angles of the ankle joint in the period of 81% to 100% of one walking cycle is determined as a walking parameter. In addition, the prediction model created with the mean value of the angles of one ankle joint of the female subject in the period of 81% to 100% of one walking cycle as the explanatory variable is determined as the prediction model used by the cognitive function determination unit 113.

The processor 11 of the cognitive function evaluation device 1 in the fourteenth modification of the present embodiment further includes the sex recognition unit that recognizes the sex of the subject.

The memory 12 stores in advance a prediction model generated with the mean value of the time series data of the angle of the ankle joint of one foot of the female subject in the period of 81% to 100% of one walking cycle as an input value, and with whether or not the subject has mild cognitive impairment as an output value.

When the sex recognition unit recognizes that the subject is female, the walking parameter detection unit 112 detects time series data of the angle of the ankle joint in the swing phase of one leg. When the sex recognition unit recognizes that the subject is female, the walking parameter detection unit 112 detects time series data of the angle of the ankle joint of one foot in the period of 81% to 100% of one walking cycle. In addition, the walking parameter detection unit 112 calculates the mean value of the time series data of the angle of the ankle joint of one foot in the period of 81% to 100% of one walking cycle.

The cognitive function determination unit 113 determines the cognitive function level of the subject by using the mean value of the time series data of the angle of the ankle joint of one foot of the swing phase. The cognitive function determination unit 113 determines the cognitive function level of the female subject by using the mean value of the time series data of the angle of the ankle joint of one foot in the period of 81% to 100% of one walking cycle. By inputting the mean value of the time series data of the angle of the ankle joint of one foot in the period of 81% to 100% of one walking cycle into the prediction model, the cognitive function determination unit 113 acquires, from the prediction model, a determination result indicating whether or not the female subject has mild cognitive impairment.

In addition, in the case where the subject is female, in the swing phase (period of 81% to 100% of one walking cycle), the average waveform of the angles of the ankle joint of one foot of the mild cognitive impairment patients is smaller than the average waveform of the angles of the ankle joint of one foot of the healthy subjects. Therefore, a value between the average of the mean values of time series data of the angle of the ankle joint of one foot in the period of 81% to 100% of one walking cycle of the female mild cognitive impairment patients and the average of the mean values of time series data of the angle of the ankle joint of one foot in the period of 81% to 100% of one walking cycle of the female healthy subjects, having been experimentally obtained, may be stored in the memory 12 as the threshold value. The cognitive function determination unit 113 may determine the cognitive function level by comparing the mean value of the time series data of the angle of the ankle joint of one foot of the subject in the period of 81% to 100% of one walking cycle with the threshold value stored in advance.

Thus, in the case where the subject is female, it is possible to determine the cognitive function level with higher accuracy by using time series data of the angle of the ankle joint of one foot of the swing phase (period of 81% to 100% of one walking cycle).

Subsequently, the walking parameter in the fifteenth modification of the present embodiment will be described.

In the fifteenth modification of the present embodiment, in the case where the subject is female, the walking parameter may be a mean value of the time series data of the angle of the knee joint in the stance phase of one leg.

Figure 35:
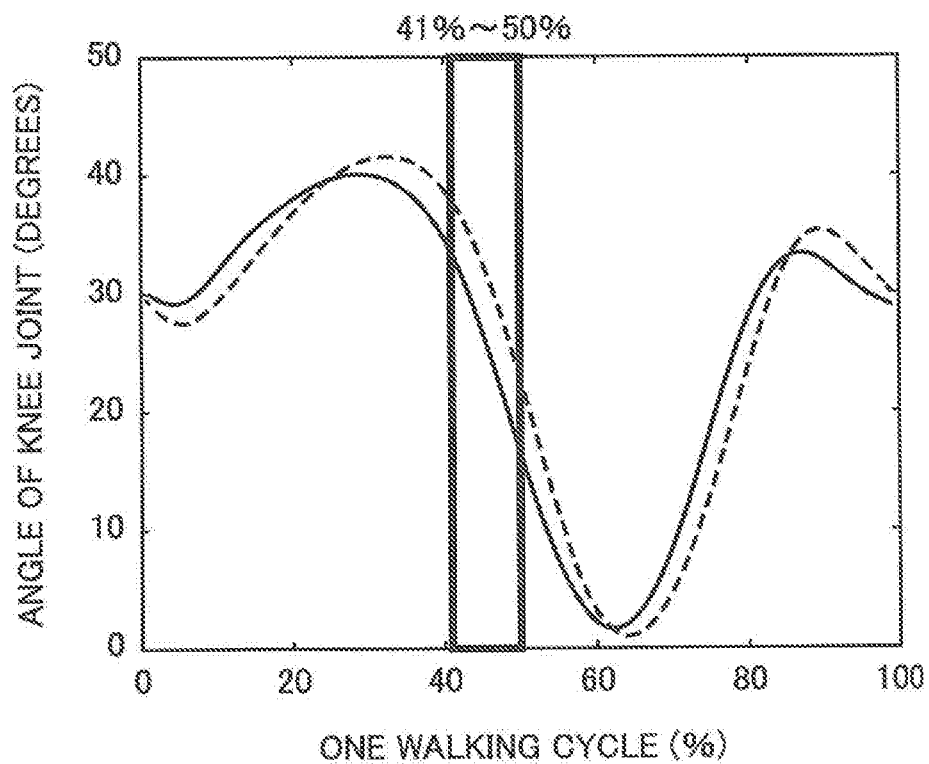
FIG. 35 is a view showing a change in the angle of one knee joint of a female subject in one walking cycle in a fifteenth modification of the present embodiment.

FIG. 35 is a view showing a change in the angle of one knee joint of a female subject in one walking cycle in the fifteenth modification of the present embodiment. In FIG. 35, the vertical axis represents the angle of the knee joint, and the horizontal axis represents one normalized walking cycle. In addition, in FIG. 35, the dashed line represents an average waveform of the angles of one knee joint of the female healthy subjects, and the solid line represents an average waveform of the angles of one knee joint of the female mild cognitive impairment patients.

In the fifteenth modification of the present embodiment, unlike the above experiment, time series data of the angle of one knee joint of each of the female subjects was detected.

In addition, a prediction model was created with whether or not the subject has mild cognitive impairment as an objective variable, and with the mean value of the angles of one knee joint in the period of 41% to 50% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 36:
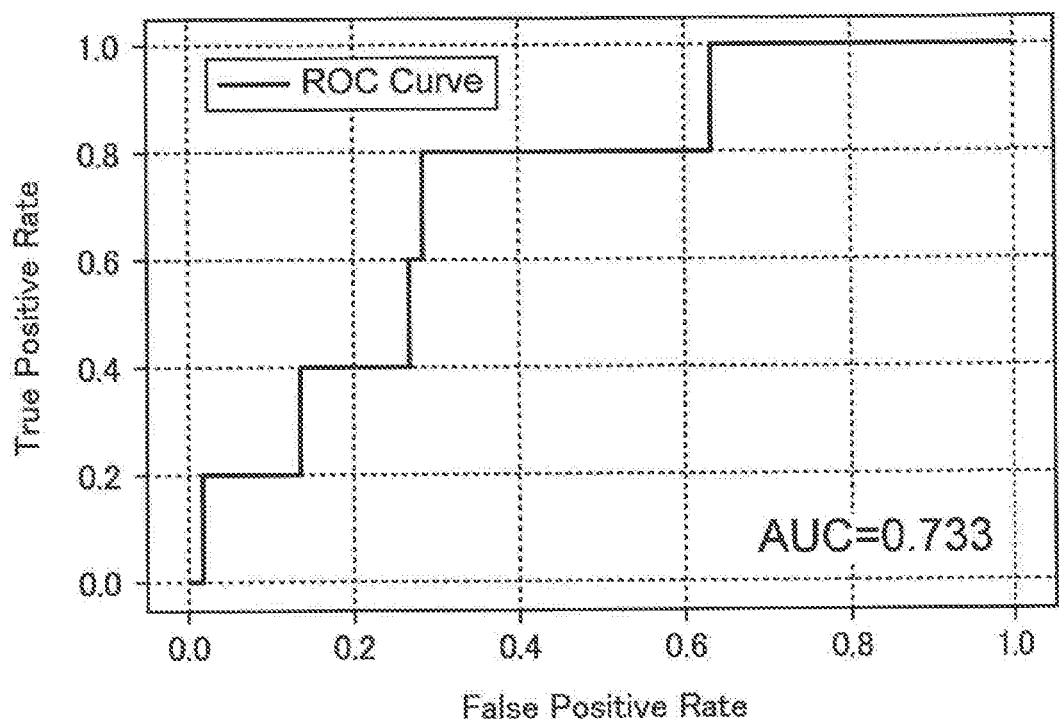
FIG. 36 is a view showing an ROC curve obtained as a result of determining a healthy subject and a mild cognitive impairment subject using a prediction model in the fifteenth modification of the present embodiment.

FIG. 36 is a view showing an ROC curve obtained as a result of determining a healthy subject and a mild cognitive impairment subject using a prediction model in the fifteenth modification of the present embodiment.

The prediction model in the fifteenth modification of the present embodiment was created with whether or not the subject has mild cognitive impairment as an objective variable, and with the mean value of the angles of one knee joint of the female subject in the period of 41% to 50% of one walking cycle as an explanatory variable. In FIG. 36, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 36 was obtained by plotting the true positive rate and the false positive rate of the prediction model created with the mean value of the angles of one knee joint of the female subject in the period of 41% to 50% of one walking cycle as an explanatory variable. The AUC value of the ROC curve shown in FIG. 36 was 0.733. When the subject is a female, the mean value of the angles of the knee joint in the period of 41% to 50% of one walking cycle is determined as a walking parameter. In addition, the prediction model created with the mean value of the angles of one knee joint of the female subject in the period of 41% to 50% of one walking cycle as the explanatory variable is determined as the prediction model used by the cognitive function determination unit 113.

The processor 11 of the cognitive function evaluation device 1 in the fifteenth modification of the present embodiment further includes the sex recognition unit that recognizes the sex of the subject.

The memory 12 stores in advance a prediction model generated with the mean value of the time series data of the angle of the knee joint of one leg of the female subject in the period of 41% to 50% of one walking cycle as an input value, and with whether or not the subject has mild cognitive impairment as an output value.

When the sex recognition unit recognizes that the subject is female, the walking parameter detection unit 112 detects time series data of the angle of the knee joint in the stance phase of one leg. When the sex recognition unit recognizes that the subject is female, the walking parameter detection unit 112 detects time series data of the angle of the knee joint of one leg in the period of 41% to 50% of one walking cycle. In addition, the walking parameter detection unit 112 calculates the mean value of the time series data of the angle of the knee joint of one leg in the period of 41% to 50% of one walking cycle.

The cognitive function determination unit 113 determines the cognitive function level of the subject by using the mean value of the time series data of the angle of the knee joint in the stance phase of one leg. The cognitive function determination unit 113 determines the cognitive function level of the female subject by using the mean value of the time series data of the angle of the knee joint of one leg in the period of 41% to 50% of one walking cycle. By inputting the mean value of the time series data of the angle of the knee joint of one leg in the period of 41% to 50% of one walking cycle into the prediction model, the cognitive function determination unit 113 acquires, from the prediction model, a determination result indicating whether or not the female subject has mild cognitive impairment.

In addition, in the case where the subject is female, in the stance phase (period of 41% to 50% of one walking cycle), the average waveform of the angles of the knee joint of one leg of the mild cognitive impairment patients is smaller than the average waveform of the angles of the knee joint of one leg of the healthy subjects. Therefore, a value between the average of the mean values of time series data of the angle of the knee joint of one leg in the period of 41% to 50% of one walking cycle of the female mild cognitive impairment patients and the average of the mean values of time series data of the angle of the knee joint of one leg in the period of 41% to 50% of one walking cycle of the female healthy subjects, having been experimentally obtained, may be stored in the memory 12 as the threshold value. The cognitive function determination unit 113 may determine the cognitive function level by comparing the mean value of the time series data of the angle of the knee joint of one leg of the subject in the period of 41% to 50% of one walking cycle with the threshold value stored in advance.

Thus, in the case where the subject is female, it is possible to determine the cognitive function level with higher accuracy by using time series data of the angle of the knee joint of one leg of the stance phase (period of 41% to 50% of one walking cycle).

Subsequently, the walking parameters in the sixteenth modification of the present embodiment will be described.

In the sixteenth modification of the present embodiment, in the case where the subject is female, the walking parameter may be a mean value of the time series data of the first vertical displacement of the waist in the first period of the stance phase of one leg and a mean value of the time series data of the second vertical displacement of the waist in the second period of the swing phase of one leg.

Figure 37:
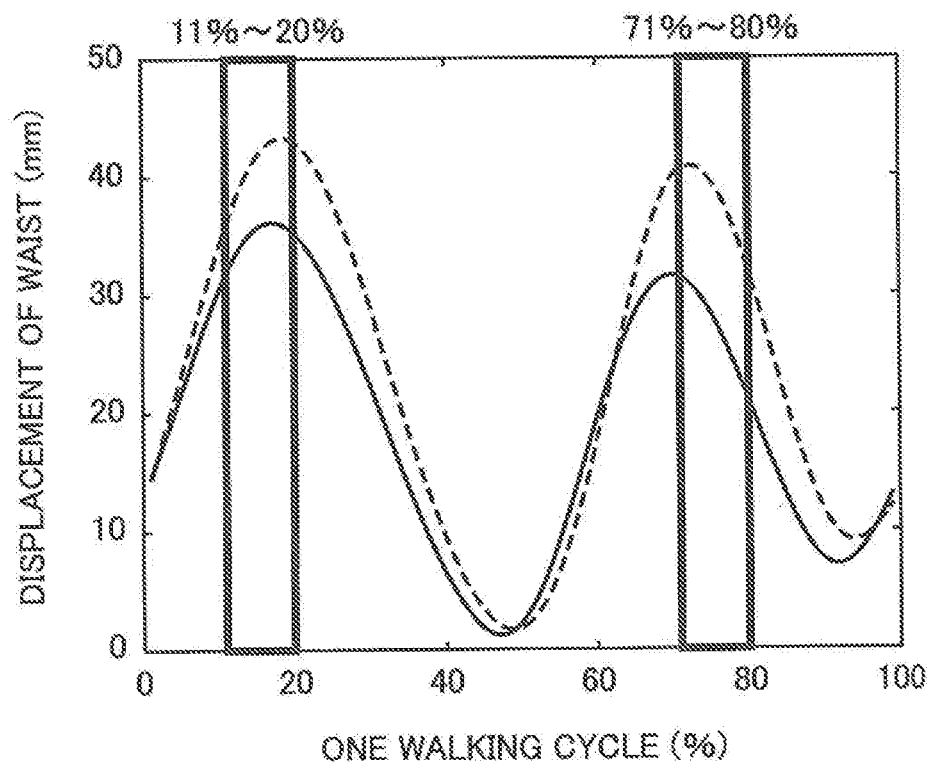
FIG. 37 is a view showing a vertical displacement of a waist of a female subject in one walking cycle in a sixteenth modification of the present embodiment.

FIG. 37 is a view showing a vertical displacement of a waist of a female subject in one walking cycle in the sixteenth modification of the present embodiment. In FIG. 37, the vertical axis represents the vertical displacement of the waist, and the horizontal axis represents one normalized walking cycle. In addition, in FIG. 37, the dashed line represents an average waveform of the vertical displacement of the waist of the female healthy subjects, and the solid line represents an average waveform of the vertical displacement of the waist of the female mild cognitive impairment patients.

In the sixteenth modification of the present embodiment, unlike the above experiment, time series data of the vertical displacement of the waist of each of the female subjects was detected. In addition, a prediction model was created with whether or not the subject has mild cognitive impairment as an objective variable and with the mean value of the vertical displacements of the waist in the period of 11% to 20% of one walking cycle and the mean value of the vertical displacements of the waist in the period of 71% to 80% of one walking cycle as explanatory variables. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 38:
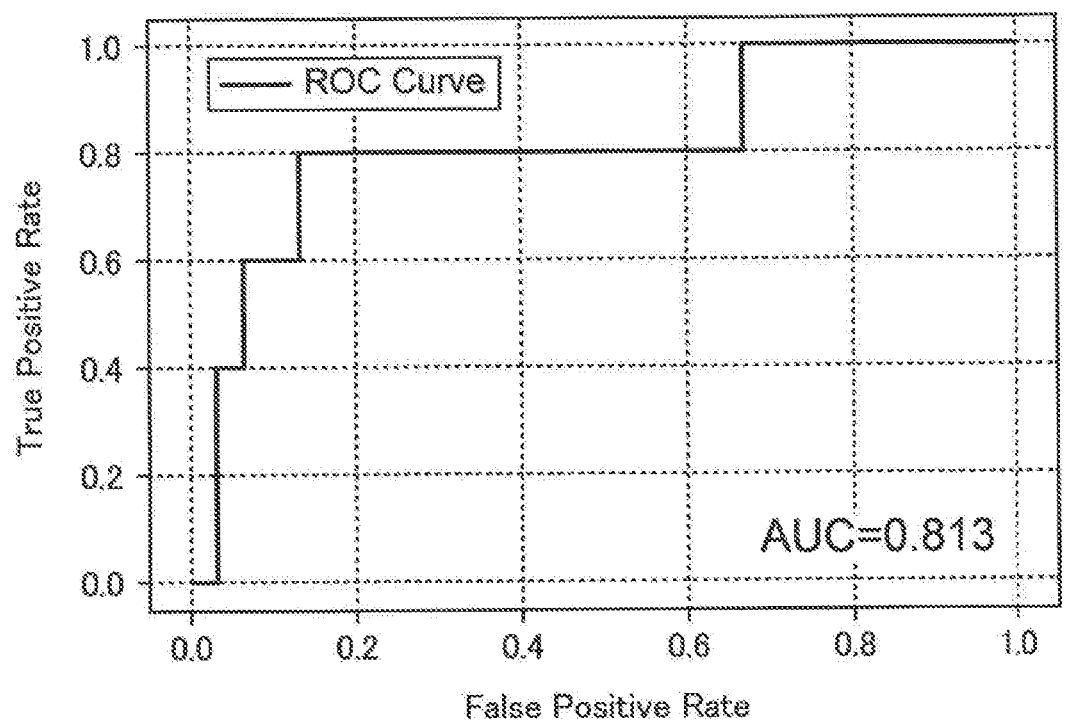
FIG. 38 is a view showing an ROC curve obtained as a result of determining a healthy subject and a mild cognitive impairment subject using a prediction model in the sixteenth modification of the present embodiment.

FIG. 38 is a view showing an ROC curve obtained as a result of determining a healthy subject and a mild cognitive impairment subject using a prediction model in the sixteenth modification of the present embodiment.

The prediction model in the sixteenth modification of the present embodiment was created with whether or not the subject has mild cognitive impairment as an objective variable, and with the mean value of the vertical displacements of the waist of the female subject in the period of 11% to 20% of one walking cycle and the mean value of the vertical displacements of the waist of the female subject in the period of 71% to 80% of one walking cycle as explanatory variables. In FIG. 38, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 38 was obtained by plotting the true positive rate and the false positive rate of the prediction model created with the mean value of the vertical displacements of the waist of the female subject in the period of 11% to 20% of one walking cycle and the mean value of the vertical displacements of the waist of the female subject in the period of 71% to 80% of one walking cycle as explanatory variables. The AUC value of the ROC curve shown in FIG. 38 was 0.813. In the case where the subject is female, the mean value of the vertical displacements of the waist in the period of 11% to 20% of one walking cycle and the mean value of the vertical displacements of the waist in the period of 71% to 80% of one walking cycle are determined as walking parameters. In addition, the prediction model created with the mean value of the vertical displacements of the waist of the female subject in the period of 11% to 20% of one walking cycle and the mean value of the vertical displacements of the waist of the female subject in the period of 71% to 80% of one walking cycle as explanatory variables is determined as the prediction model used by the cognitive function determination unit 113.

The processor 11 of the cognitive function evaluation device 1 in the sixteenth modification of the present embodiment further includes the sex recognition unit that recognizes the sex of the subject.

When the sex recognition unit recognizes that the subject is female, the walking parameter detection unit 112 detects time series data of the first vertical displacement of the waist in the first period of the stance phase of one leg and time series data of the second vertical displacement of the waist in the second period of the swing phase of one leg. The first period is a period of 11% to 20% of one walking cycle, and the second period is a period of 71% to 80% of one walking cycle. When the sex recognition unit recognizes that the subject is female, the walking parameter detection unit 112 detects time series data of the vertical displacement of the waist in the period of 11% to 20% of one walking cycle and time series data of the vertical displacement of the waist in the period of 71% to 80% of one walking cycle. In addition, the walking parameter detection unit 112 calculates the mean value of time series data of the vertical displacement of the waist in the period of 11% to 20% of one walking cycle and the mean value of time series data of the vertical displacement of the waist in the period of 71% to 80% of one walking cycle.

The cognitive function determination unit 113 determines the cognitive function level of the female subject by using the mean value of the time series data of the first vertical displacement of the waist in the first period of the stance phase and the mean value of the time series data of the second vertical displacement of the waist in the second period of the swing phase.

The memory 12 stores in advance a prediction model generated with the mean value of the time series data of the first vertical displacement of the waist of the female subject in the first period of the stance phase of one leg and the mean value of the time series data of the second vertical displacement of the waist of the female subject in the second period of the swing phase of one leg as input values, and with whether or not the subject has mild cognitive impairment as an output value. The memory 12 stores in advance a prediction model generated with the mean value of the vertical displacements of the waist of the female subject in the period of 11% to 20% of one walking cycle and the mean value of the vertical displacements of the waist of the female subject in the period of 71% to 80% of one walking cycle as input values, and with whether or not the subject has mild cognitive impairment as an output value.

The cognitive function determination unit 113 determines the cognitive function level of the female subject by using the mean value of time series data of the vertical displacement of the waist in the period of 11% to 20% of one walking cycle and the mean value of time series data of the vertical displacement of the waist in the period of 71% to 80% of one walking cycle. By inputting the mean value of time series data of the vertical displacement of the waist in the period of 11% to 20% of one walking cycle and the mean value of time series data of the vertical displacement of the waist in the period of 71% to 80% of one walking cycle into the prediction model, the cognitive function determination unit 113 acquires, from the prediction model, a determination result indicating whether or not the female subject has mild cognitive impairment.

Thus, in the case where the subject is female, it is possible to determine the cognitive function level with higher accuracy by using time series data of the vertical displacement of the waist of the stance phase (period of 11% to 20% of one walking cycle) and the swing phase (period of 71% to 80% of one walking cycle).

Subsequently, the walking parameters in the seventeenth modification of the present embodiment will be described.

In the seventeenth modification of the present embodiment, in the case where the subject is female, the walking parameter may be a vertical displacement of the waist at a predetermined time point in the swing phase of one leg.

Figure 39:
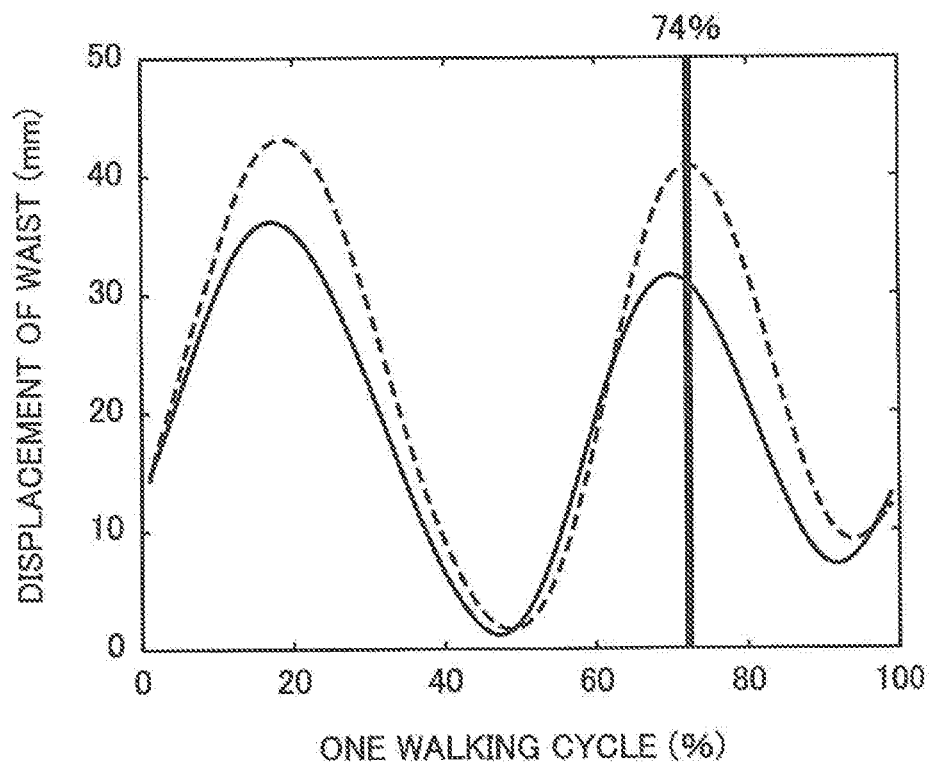
FIG. 39 is a view showing a vertical displacement of a waist of a female subject in one walking cycle in a seventeenth modification of the present embodiment.

FIG. 39 is a view showing a vertical displacement of a waist of a female subject in one walking cycle in the seventeenth modification of the present embodiment. In FIG. 39, the vertical axis represents the vertical displacement of the waist, and the horizontal axis represents one normalized walking cycle. In addition, in FIG. 39, the dashed line represents an average waveform of the vertical displacement of the waist of the female healthy subjects, and the solid line represents an average waveform of the vertical displacement of the waist of the female mild cognitive impairment patients.

In the seventeenth modification of the present embodiment, unlike the above experiment, time series data of the vertical displacement of the waist of each of the female subjects was detected. In addition, a prediction model was created with whether or not the subject has mild cognitive impairment as an objective variable, and with the vertical displacement of the waist at the time point of 74% of one walking cycle as an explanatory variable. The prediction model was evaluated by cross validation. Leave-one-out cross validation was adopted as the cross validation. Then, the ROC curve of the prediction model was calculated. Furthermore, the AUC value of the ROC curve of the prediction model was calculated.

Figure 40:
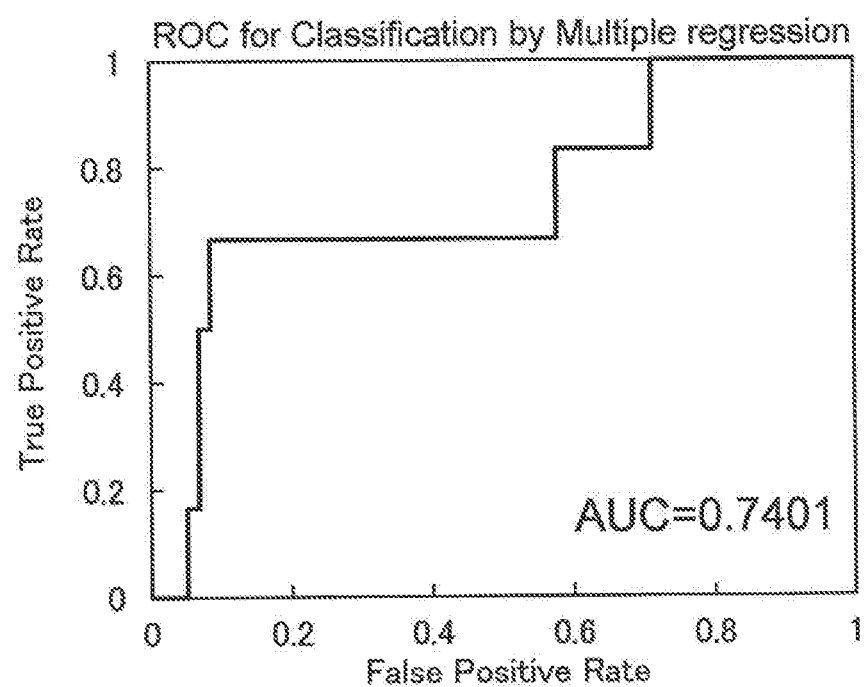
FIG. 40 is a view showing an ROC curve obtained as a result of determining a healthy subject and a mild cognitive impairment subject using a prediction model in the seventeenth modification of the present embodiment.

FIG. 40 is a view showing an ROC curve obtained as a result of determining a healthy subject and a mild cognitive impairment subject using a prediction model in the seventeenth modification of the present embodiment.

The prediction model in the seventeenth modification of the present embodiment was created with whether or not the subject has mild cognitive impairment as an objective variable, and with the vertical displacement of the waist of the female subject at the time point of 74% of one walking cycle as an explanatory variable. In FIG. 40, the vertical axis represents the true positive rate, and the horizontal axis represents the false positive rate. The true positive rate indicates a ratio at which the prediction model has correctly determined the mild cognitive impairment patient as having mild cognitive impairment, and the false positive rate indicates a ratio at which the prediction model has incorrectly determined a healthy subject as having mild cognitive impairment.

The ROC curve shown in FIG. 40 was obtained by plotting the true positive rate and the false positive rate of the prediction model created with the vertical displacement of the waist of the female subject at the time point of 74% of one walking cycle as an explanatory variable. The AUC value of the ROC curve shown in FIG. 40 was 0.7401. In the case where the subject is female, the vertical displacement of the waist at the time point of 74% of one walking cycle is determined as a walking parameter. In addition, the prediction model created with the vertical displacement of the waist of the female subject at the time point of 74% of one walking cycle as the explanatory variable is determined as the prediction model used by the cognitive function determination unit 113.

The processor 11 of the cognitive function evaluation device 1 in the seventeenth modification of the present embodiment further includes the sex recognition unit that recognizes the sex of the subject.

When the sex recognition unit recognizes that the subject is female, the walking parameter detection unit 112 detects the vertical displacement of the waist at a predetermined time point in the swing phase of one leg. The predetermined time point is a time point of 74% of one walking cycle. When the sex recognition unit recognizes that the subject is female, the walking parameter detection unit 112 detects the vertical displacement of the waist at the time point of 74% of one walking cycle.

It is to be noted that the time point of 74% of one walking cycle is in a vicinity of the time point at which the maximum value of the vertical displacement of the waist in the swing phase of one leg is detected. Therefore, when the sex recognition unit recognizes that the subject is female, the walking parameter detection unit 112 may detect the maximum value of the vertical displacement of the waist in the swing phase of the one leg.

The cognitive function determination unit 113 determines the cognitive function level of the female subject by using the vertical displacement of the waist at a predetermined time point in the swing phase.

The memory 12 stores in advance a prediction model generated with the vertical displacement of the waist of the female subject at a predetermined time point in the swing phase of one leg as an input value, and with whether or not the subject has mild cognitive impairment as an output value. The memory 12 stores in advance a prediction model generated with the vertical displacement of the waist of the female subject at the time point of 74% of one walking cycle as an input value, and with whether or not the subject has mild cognitive impairment as an output value.

The cognitive function determination unit 113 determines the cognitive function level of the female subject by using the vertical displacement of the waist at the time point of 74% of one walking cycle. By inputting the vertical displacement of the waist at the time point of 74% of one walking cycle into the prediction model, the cognitive function determination unit 113 acquires, from the prediction model, a determination result indicating whether or not the female subject has mild cognitive impairment.

Thus, in the case where the subject is female, it is possible to determine the cognitive function level with higher accuracy by using the vertical displacement of the waist at the predetermined time point in the swing phase (time point of 74% of one walking cycle).

FIG. 41 is a view showing an example of an evaluation result screen displayed in the present embodiment.

The display unit 3 displays the evaluation result screen shown in FIG. 41. The evaluation result screen includes a cognitive function evaluation presentation region 31 showing a past evaluation value of the cognitive function and a current evaluation value of the cognitive function, and an evaluation message 32. In the cognitive function evaluation presentation region 31 of FIG. 41, evaluation of the cognitive function is performed once a month, and the evaluation values of the cognitive function for the past six months and the evaluation value of the cognitive function for this month are displayed.

The evaluation value of the cognitive function is a value indicating the cognitive function level calculated by the prediction model. The value indicating the cognitive function level is represented by 0.0 to 1.0, for example. The evaluation result presentation unit 114 converts a value indicating the cognitive function level into a percentage and presents it as an evaluation value of the cognitive function.

It is to be noted that in a case where the past evaluation value of the cognitive function is displayed together with the current evaluation value of the cognitive function, the cognitive function determination unit 113 stores the evaluation value of the cognitive function in the memory 12.

In addition, the cognitive function evaluation presentation region 31 may display, as an evaluation result, whether or not the subject has mild cognitive impairment.

In addition, the evaluation message 32 of "The risk of MCI is lower than in the last month, and you are keeping a good condition. Keep yourself in good shape." is displayed. When the evaluation value of the cognitive function of this month is lower than the evaluation value of the cognitive function of the last month and the evaluation value of the cognitive function of this month is lower than 0.5, the evaluation result presentation unit 114 reads the evaluation message 32 shown in FIG. 41 from the memory 12 and outputs it to the display unit 3.

It is to be noted that while in the present embodiment, the past evaluation values of the cognitive function are displayed together with the current evaluation value of the cognitive function, the present disclosure is not particularly limited to this, and only the current evaluation value of the cognitive function may be displayed. In this case, the cognitive function determination unit 113 is not required to store the evaluation value of the cognitive function in the memory 12.

In addition, the camera 2 in the present embodiment may be a security camera provided in front of the entrance, a camera slave machine of a video intercom, or a monitoring camera provided in a room. In addition, the display unit 3 may be a display of a smartphone, a tablet computer, or a video intercom.

It is to be noted that while in the present embodiment, the walking parameter detection unit 112 extracts skeleton data based on the moving image data acquired from the camera 2, the present disclosure is not particularly limited thereto, and skeleton data may be extracted using a motion capture system. The motion capture system may be optical, magnetic, mechanical, or inertial sensor based. For example, in an optical motion capture system, a camera captures an image of a subject with a marker attached to a joint and detects the position of the marker from the captured image. The walking parameter detection unit 112 acquires the skeleton data of the subject from the position data detected by the motion capture system. As the optical motion capture system, for example, a three-dimensional motion analysis device manufactured by Inter Reha Co., Ltd. is available.

In addition, the motion capture system may include a depth sensor and a color camera, and the motion capture system may automatically extract position information of a joint point of the subject from an image and detect the attitude of the subject. In this case, the subject does not need to attach the marker. As such a motion capture system, for example, Kinect manufactured by Microsoft Corporation is available.

In measurement of walking motion using a motion capture system, it is preferable that the angle of the ankle joint, the angle of the knee joint, or the vertical displacement of the waist in the walking motion be extracted from the position coordinates, and the feature amount of the walking motion be detected from the extracted angle or displacement.

It is to be noted that, in each of the above embodiments, each component may be configured by dedicated hardware or may be realized by executing a software program suitable for each component. Each component may be realized by a program execution unit such as a CPU or a processor reading and executing a software program recorded in a recording medium such as a hard disk or a semiconductor memory.

Some or all of the functions of the device according to the embodiment of the present disclosure are realized as a large scale integration (LSI), which is typically an integrated circuit. These may be individually integrated into one chip, or may be integrated into one chip so as to include some or all of them. In addition, the integrated circuit is not limited to LSI, and may be realized by a dedicated circuit or a general-purpose processor. A field programmable gate array (FPGA), which can be programmed after manufacturing the LSI, or a reconfigurable processor, which can reconfigure the connection and setting of the circuit cell inside the LSI, may be used.

In addition, some or all of the functions of the device according to the embodiment of the present disclosure may be realized by a processor such as a CPU executing a program.

In addition, all of the numerals used above are merely examples for specifically describing the present disclosure, and the present disclosure is not limited to the exemplified numerals.

In addition, the order of executing the steps shown in the flowchart is an example for the purpose of specifically describing the present disclosure, and may be any order other than the above as long as a similar effect is obtained. In addition, some of the above steps may be executed simultaneously (parallel) with other steps.

Since the technology according to the present disclosure can simply and highly accurately evaluate the cognitive function, it is useful for the technology of evaluating the cognitive function based on the walking motion of a subject.

This application is based on U.S. Provisional application No. 62/893,297 filed in United States Patent and Trademark Office on Aug. 29, 2019 and Japanese Patent application No. 2020-023432 filed in Japan Patent Office on Feb. 14, 2020, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. A cognitive function evaluation method that evaluates a cognitive function based on a walking motion of a subject, the cognitive function evaluation method comprising:
   acquiring, from a camera, image walking data related to the walking motion of the subject;
   detecting, using a programmed controller and from the image walking data, time series skeletal data of an angle of an ankle joint of one foot in a predetermined period of a swing phase of one leg of the subject
   where the predetermined period is 85% to 88% of one walking cycle, the walking cycle expressed by 1% to 100%, the walking cycle being an interval of when the one foot of the subject touches a ground to when the one foot touches the ground again;
   determining, using the programmed controller, a cognitive function level of the subject by using a mean value of the time series skeletal data of the angle of the ankle joint;
   and outputting, to a display, the cognitive function level and an evaluation message associated with the cognitive function level,
   the display including a line graph depicting a monthly trend of the cognitive function level, a current value of the cognitive function level, and a previous month's value of the cognitive function level,
   the monthly trend and the previous month's value both being based on previous time series of periods, each of the periods equal to the predetermined period;
   wherein the evaluation message is advice based on the monthly trend and the current value of the cognitive function level;
   where the display and the camera are part of a smartphone or tablet computer.

2. A cognitive function evaluation method that evaluates a cognitive function based on a walking motion of a subject, the cognitive function evaluation method comprising:
   acquiring, from a camera, image walking data related to the walking motion of the subject,
   detecting, using a programmed controller and from the image walking data, time series skeletal data of a first angle of an ankle joint of one foot in a first period of a stance phase of one leg of the subject and time series skeletal data of a second angle of the ankle joint in a second period of a swing phase of the one leg,
   where the first period is 45% to 50% of one walking cycle, and where the second period is 85% to 88% of the one walking cycle, the walking cycle expressed by 1% to 100%, the walking cycle being an interval of when the one foot of the subject touches a ground to when the one foot touches the ground again;
   determining, using the programmed controller, a cognitive function level of the subject by using a mean value of the time series skeletal data of the first angle of the ankle joint and a mean value of the time series skeletal data of the second angle of the ankle joint,
   and outputting, to a display, the cognitive function level and an evaluation message associated with the cognitive function level,
   the display including a line graph depicting a monthly trend of the cognitive function level, a current value of the cognitive function level, and a previous month's value of the cognitive function level,
   the monthly trend and the previous month's value both being based on previous time series of first periods and second periods, each of the first periods and the second periods being equal to the first period and the second period, respectively,
   wherein the evaluation message is advice based on the monthly trend and the current value of the cognitive function level;
   where the display and the camera are part of a smartphone or tablet computer.

3. A cognitive function evaluation method that evaluates a cognitive function based on a walking motion of a subject, the cognitive function evaluation method comprising:
   acquiring, from a camera, image walking data related to the walking motion of the subject;
   detecting, using a programmed controller and from the image walking data, time series skeletal data of an angle of a knee joint of one leg of the subject in a first period of a stance phase of the one leg and time series skeletal data of an angle of an ankle joint of one foot in a second period of a swing phase of the one leg,
   where the first period is 45% to 50% of one walking cycle, and where the second period is 85% to 88% of the one walking cycle, the walking cycle expressed by 1% to 100%, the walking cycle being an interval of when the one foot of the subject touches a ground to when the one foot touches the ground again;
   determining a cognitive function level of the subject by using a mean value of the time series skeletal data of the angle of the knee joint and a mean value of the time series skeletal data of the angle of the ankle joint;
   and outputting, to a display, the cognitive function level and an evaluation message associated with the cognitive function level,
   the display including a line graph depicting a monthly trend of the cognitive function level, a current value of the cognitive function level, and a previous month's value of the cognitive function level,
   the monthly trend and the previous month's value both being based on previous time series of first periods and second periods, each of the first periods and the second periods being equal to the first period and the second period, respectively,
   wherein the evaluation message is advice based on the monthly trend and the current value of the cognitive function level;
   where the display and the camera are part of a smartphone or tablet computer.

* * * * *